United States Patent
Hood et al.

(10) Patent No.: US 8,968,274 B2
(45) Date of Patent: Mar. 3, 2015

(54) ACOUSTICALLY CONTROLLED SUBSTANCE DELIVERY DEVICE

(75) Inventors: Leroy E. Hood, Seattle, WA (US);
Muriel Y. Ishikawa, Livermore, CA (US); Edward K. Y. Jung, Bellevue, WA (US); Robert Langer, Newton, MA (US); Clarence T. Tegreene, Bellevue, WA (US); Lowell L. Wood, Jr., Livermore, CA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 641 days.

(21) Appl. No.: 12/217,873

(22) Filed: Jul. 8, 2008

(65) Prior Publication Data

US 2009/0054877 A1 Feb. 26, 2009

Related U.S. Application Data

(60) Division of application No. 11/372,492, filed on Mar. 9, 2006, and a continuation-in-part of application No. 11/271,145, filed on Nov. 9, 2005.

(51) Int. Cl.
*A61K 9/22* (2006.01)
*A61M 5/142* (2006.01)
(Continued)

(52) U.S. Cl.
CPC ... *A61M 5/14276* (2013.01); *A61M 2205/0288* (2013.01); *A61M 2005/14513* (2013.01);
(Continued)

(58) Field of Classification Search
CPC ........... A61M 2005/14513; A61M 2205/0266; A61M 2205/0288; A61M 2205/3507; A61M 2205/3523; A61M 2205/3569; A61M 2205/36; A61M 5/14276; A61M 5/145; A61M 5/172; A61M 5/1723
USPC .................. 604/890.1, 892.1, 891.1; 424/423
See application file for complete search history.

(56) References Cited

U.S. PATENT DOCUMENTS 3,760,806 A 9/1973 Leeper
3,923,426 A 12/1975 Theeuwes
(Continued)

FOREIGN PATENT DOCUMENTS

JP 60118289 A 6/1985
WO WO 02/056790 A2 7/2002
(Continued)

OTHER PUBLICATIONS

U.S. Appl. No. 11/372,226, Hood et al.
(Continued)

*Primary Examiner* — Emily Schmidt
*Assistant Examiner* — Michael J Anderson
(74) *Attorney, Agent, or Firm* — Suiter Swantz pc llo

(57) ABSTRACT

Embodiments of a system including a remotely controlled substance delivery device and associated controller are described. Methods of use and control of the device are also disclosed. According to some embodiments, a delivery device or related device may be placed in an environment in order to pump a material into the environment or into an additional fluid handling structure within the device. Exemplary environments include a body of an organism, a body of water, or an enclosed volume of a fluid. The concentration of a substance in the fluid to be delivered may be modified by a remote control signal. In selected embodiments, an acoustic control signal may be used.

30 Claims, 51 Drawing Sheets

(51) Int. Cl.
*A61M 5/145* (2006.01)
*A61M 5/172* (2006.01)

(52) U.S. Cl.
CPC ...... *A61M5/1723* (2013.01); *A61M 2205/3569* (2013.01); *A61M 2205/36* (2013.01); *A61M 2205/0266* (2013.01); *A61M 2205/3507* (2013.01); *A61M 5/172* (2013.01); *A61M 2205/3523* (2013.01); *A61M 5/145* (2013.01)
USPC .................................................. 604/890.1

(56) References Cited

U.S. PATENT DOCUMENTS

| | | |
|---|---|---|
| 4,053,952 A | 10/1977 | Goldstein |
| 4,263,910 A | 4/1981 | Pardekooper et al. |
| 4,360,019 A | 11/1982 | Portner et al. |
| 4,373,527 A | 2/1983 | Fischell |
| 4,457,752 A | 7/1984 | Vadasz |
| 4,513,034 A | 4/1985 | Sparer et al. |
| 4,579,837 A | 4/1986 | Busch et al. |
| 4,642,230 A | 2/1987 | Whitehead et al. |
| 4,692,147 A | 9/1987 | Duggan |
| 4,714,462 A | 12/1987 | DiDomenico |
| 4,753,636 A | 6/1988 | Free |
| 4,779,806 A | 10/1988 | Langer et al. |
| 4,787,888 A | 11/1988 | Fox |
| 4,834,704 A | 5/1989 | Reinicke |
| 4,861,484 A | 8/1989 | Lichtin et al. |
| 4,883,666 A | 11/1989 | Sabel et al. |
| 4,929,233 A | 5/1990 | Roth et al. |
| 4,944,659 A | 7/1990 | Labbe et al. |
| 4,952,406 A | 8/1990 | Brown et al. |
| 5,019,372 A | 5/1991 | Folkman et al. |
| 5,045,082 A | 9/1991 | Ayer et al. |
| 5,049,141 A | 9/1991 | Olive |
| 5,059,175 A | 10/1991 | Hanover et al. |
| 5,167,625 A | 12/1992 | Jacobsen et al. |
| 5,170,801 A | 12/1992 | Casper et al. |
| 5,207,666 A | 5/1993 | Idriss et al. |
| 5,217,449 A | 6/1993 | Yuda et al. |
| 5,279,607 A | 1/1994 | Schentag et al. |
| 5,368,571 A | 11/1994 | Horres, Jr. |
| 5,370,611 A | 12/1994 | Niezink et al. |
| 5,370,672 A | 12/1994 | Fowler et al. |
| 5,391,164 A | 2/1995 | Giampapa |
| 5,395,366 A | 3/1995 | D'Andrea et al. |
| 5,484,403 A | 1/1996 | Yoakum et al. |
| 5,505,706 A | 4/1996 | Maus et al. |
| 5,523,746 A | 6/1996 | Gallagher |
| 5,643,246 A | 7/1997 | Leeb et al. |
| 5,644,177 A | 7/1997 | Guckel et al. |
| 5,651,979 A | 7/1997 | Ron et al. |
| 5,655,539 A | 8/1997 | Wang et al. |
| 5,666,977 A | 9/1997 | Higgins et al. |
| 5,667,504 A | 9/1997 | Baumann et al. |
| 5,698,220 A | 12/1997 | Cardinal et al. |
| 5,719,296 A | 2/1998 | Acton, III et al. |
| 5,733,313 A | 3/1998 | Barreras, Sr. et al. |
| 5,770,222 A | 6/1998 | Unger et al. |
| 5,797,898 A | 8/1998 | Santini, Jr. et al. |
| 5,800,420 A | 9/1998 | Gross et al. |
| 5,814,599 A | 9/1998 | Mitragotri et al. |
| 5,827,186 A | 10/1998 | Chen et al. |
| 5,830,207 A | 11/1998 | Leeb et al. |
| 5,869,078 A | 2/1999 | Baudino |
| 5,879,329 A | 3/1999 | Ginsburg |
| 5,928,195 A | 7/1999 | Malamud et al. |
| 5,935,593 A | 8/1999 | Ron et al. |
| 5,945,762 A | 8/1999 | Chen et al. |
| 5,993,414 A | 11/1999 | Haller |
| 6,048,328 A | 4/2000 | Haller et al. |
| 6,048,734 A | 4/2000 | Burns et al. |
| 6,077,837 A | 6/2000 | Kozak |
| 6,086,582 A | 7/2000 | Altman et al. |
| 6,116,863 A | 9/2000 | Ahn et al. |
| 6,122,536 A | 9/2000 | Sun et al. |
| 6,146,103 A | 11/2000 | Lee et al. |
| 6,152,181 A | 11/2000 | Wapner et al. |
| 6,198,950 B1 | 3/2001 | Kraus |
| 6,198,963 B1 | 3/2001 | Haim et al. |
| 6,203,523 B1 | 3/2001 | Haller et al. |
| 6,206,914 B1 | 3/2001 | Soykan et al. |
| 6,246,241 B1 | 6/2001 | Newland |
| 6,261,584 B1 | 7/2001 | Peery et al. |
| 6,269,340 B1 | 7/2001 | Ford et al. |
| 6,270,680 B1 | 8/2001 | Silveri et al. |
| 6,272,370 B1 | 8/2001 | Gillies et al. |
| 6,312,393 B1 | 11/2001 | Abreu |
| 6,339,897 B1 | 1/2002 | Hayes et al. |
| 6,358,247 B1 | 3/2002 | Altman et al. |
| 6,395,292 B2 | 5/2002 | Peery et al. |
| 6,408,878 B2 | 6/2002 | Unger et al. |
| 6,416,495 B1 | 7/2002 | Kriesel et al. |
| 6,436,069 B1 | 8/2002 | Jellie |
| 6,454,759 B2 | 9/2002 | Krulevitch et al. |
| 6,458,118 B1 | 10/2002 | Lent et al. |
| 6,464,687 B1 | 10/2002 | Ishikawa et al. |
| 6,475,750 B1 | 11/2002 | Han et al. |
| 6,491,061 B1 | 12/2002 | Lopez et al. |
| 6,491,684 B1 | 12/2002 | Joshi et al. |
| 6,500,165 B1 | 12/2002 | Frank |
| 6,500,168 B1 | 12/2002 | Jellie |
| 6,511,473 B2 | 1/2003 | Bartha et al. |
| 6,537,256 B2 | 3/2003 | Santini, Jr. et al. |
| 6,544,193 B2 | 4/2003 | Abreu |
| 6,554,822 B1 | 4/2003 | Holschneider et al. |
| 6,562,000 B2 | 5/2003 | Thompson et al. |
| 6,565,526 B2 * | 5/2003 | Seward ........ 604/93.01 |
| 6,569,152 B2 | 5/2003 | Brines et al. |
| 6,571,125 B2 | 5/2003 | Thompson |
| 6,585,763 B1 * | 7/2003 | Keilman et al. ........ 623/1.42 |
| 6,589,205 B1 | 7/2003 | Meadows |
| 6,590,267 B1 | 7/2003 | Goodwin-Johansson et al. |
| 6,607,553 B1 | 8/2003 | Healy et al. |
| 6,615,855 B2 | 9/2003 | Lopez et al. |
| 6,628,989 B1 * | 9/2003 | Penner et al. ........ 607/59 |
| 6,632,216 B2 | 10/2003 | Houzego et al. |
| 6,635,837 B2 | 10/2003 | Subramanian et al. |
| 6,653,124 B1 | 11/2003 | Freeman |
| 6,663,821 B2 * | 12/2003 | Seward ........ 264/512 |
| 6,669,683 B2 | 12/2003 | Santini, Jr. et al. |
| 6,682,521 B2 | 1/2004 | Petrakis |
| 6,719,449 B1 | 4/2004 | Laugharn, Jr. et al. |
| 6,720,402 B2 | 4/2004 | Langer et al. |
| 6,723,086 B2 | 4/2004 | Bassuk et al. |
| 6,755,621 B2 | 6/2004 | Lopez et al. |
| 6,761,420 B2 | 7/2004 | Maluf et al. |
| 6,768,425 B2 | 7/2004 | Flaherty et al. |
| 6,768,920 B2 | 7/2004 | Lange et al. |
| 6,773,429 B2 | 8/2004 | Sheppard, Jr. et al. |
| 6,793,753 B2 | 9/2004 | Unger et al. |
| 6,796,956 B2 | 9/2004 | Hartlaub et al. |
| 6,802,489 B2 | 10/2004 | Marr et al. |
| 6,802,811 B1 | 10/2004 | Slepian |
| 6,805,783 B2 | 10/2004 | Ohkawa |
| 6,808,522 B2 | 10/2004 | Richards et al. |
| 6,824,561 B2 | 11/2004 | Soykan et al. |
| 6,830,936 B2 | 12/2004 | Anderson et al. |
| 6,845,267 B2 | 1/2005 | Harrison et al. |
| 6,849,463 B2 | 2/2005 | Santini, Jr. et al. |
| 6,929,636 B1 | 8/2005 | von Alten |
| 6,935,165 B2 | 8/2005 | Bashir et al. |
| 6,948,843 B2 | 9/2005 | Laugharn, Jr. et al. |
| 6,970,741 B1 | 11/2005 | Whitehurst et al. |
| 7,048,730 B2 | 5/2006 | Petrakis |
| 7,083,593 B2 | 8/2006 | Stultz |
| 7,104,988 B2 | 9/2006 | Altman et al. |
| 7,118,531 B2 | 10/2006 | Krill |
| 7,214,190 B1 | 5/2007 | Wilson |
| 7,351,239 B2 | 4/2008 | Gill |
| 7,424,330 B2 | 9/2008 | Duerr et al. |
| 7,474,180 B2 | 1/2009 | Bintoro et al. |
| 7,641,619 B2 * | 1/2010 | Penner ........ 600/561 |
| 7,699,834 B2 | 4/2010 | Hood et al. |

(56) References Cited

U.S. PATENT DOCUMENTS

| | | | |
|---|---|---|---|
| 7,811,279 B2 | 10/2010 | John | |
| 7,817,030 B2* | 10/2010 | Hood et al. | 340/539.12 |
| 7,819,858 B2* | 10/2010 | Goodall et al. | 604/890.1 |
| 7,896,867 B2 | 3/2011 | Gordon et al. | |
| 7,896,868 B2 | 3/2011 | Hood et al. | |
| 7,942,867 B2* | 5/2011 | Hood et al. | 604/890.1 |
| 8,083,710 B2* | 12/2011 | Hood et al. | 604/65 |
| 8,109,923 B2* | 2/2012 | Hood et al. | 604/892.1 |
| 8,114,065 B2* | 2/2012 | Hood et al. | 604/890.1 |
| 8,192,390 B2* | 6/2012 | Hood et al. | 604/19 |
| 8,273,075 B2* | 9/2012 | Hood et al. | 604/892.1 |
| 8,348,930 B2 | 1/2013 | Gordon et al. | |
| 8,349,261 B2* | 1/2013 | Hood et al. | 422/112 |
| 8,367,003 B2* | 2/2013 | Hood et al. | 422/105 |
| 8,512,241 B2* | 8/2013 | Bandy et al. | 600/302 |
| 8,529,551 B2* | 9/2013 | Hood et al. | 604/890.1 |
| 2001/0033796 A1 | 10/2001 | Unger et al. | |
| 2001/0036672 A1 | 11/2001 | Anderson et al. | |
| 2001/0039414 A1 | 11/2001 | Brines et al. | |
| 2001/0044620 A1 | 11/2001 | Krulevitch et al. | |
| 2002/0009015 A1* | 1/2002 | Laugharn et al. | 366/108 |
| 2002/0065509 A1 | 5/2002 | Lebel et al. | |
| 2002/0070116 A1 | 6/2002 | Ohkawa | |
| 2002/0072784 A1 | 6/2002 | Sheppard, Jr. et al. | |
| 2002/0077673 A1 | 6/2002 | Penner et al. | |
| 2002/0107472 A1 | 8/2002 | Thompson et al. | |
| 2002/0111601 A1 | 8/2002 | Thompson | |
| 2002/0127736 A1 | 9/2002 | Chou et al. | |
| 2002/0173772 A1 | 11/2002 | Olsen | |
| 2002/0173773 A1 | 11/2002 | Olsen | |
| 2002/0188323 A1 | 12/2002 | Penner et al. | |
| 2003/0015768 A1 | 1/2003 | Bosco et al. | |
| 2003/0036746 A1 | 2/2003 | Penner et al. | |
| 2003/0069560 A1 | 4/2003 | Adamis et al. | |
| 2003/0070677 A1 | 4/2003 | Handique et al. | |
| 2003/0104590 A1 | 6/2003 | Santini, Jr. et al. | |
| 2003/0142901 A1 | 7/2003 | Lahann et al. | |
| 2003/0147812 A1 | 8/2003 | Ueberle | |
| 2003/0163223 A1 | 8/2003 | Blomquist | |
| 2003/0171257 A1 | 9/2003 | Stirbl et al. | |
| 2003/0171738 A1 | 9/2003 | Konieczynski et al. | |
| 2003/0210997 A1 | 11/2003 | Lopez et al. | |
| 2003/0219470 A1 | 11/2003 | Zhang et al. | |
| 2003/0234220 A1 | 12/2003 | Lee et al. | |
| 2003/0235504 A1 | 12/2003 | Lemoff et al. | |
| 2004/0007051 A1 | 1/2004 | Bashir et al. | |
| 2004/0010219 A1 | 1/2004 | McCusker et al. | |
| 2004/0015154 A1 | 1/2004 | Harper et al. | |
| 2004/0032187 A1* | 2/2004 | Penner et al. | 310/311 |
| 2004/0034332 A1 | 2/2004 | Uhland | |
| 2004/0036455 A1 | 2/2004 | Cho | |
| 2004/0049245 A1 | 3/2004 | Gass et al. | |
| 2004/0055648 A1 | 3/2004 | Erickson | |
| 2004/0058101 A1 | 3/2004 | Klemm | |
| 2004/0076559 A1 | 4/2004 | Brucker et al. | |
| 2004/0079424 A1 | 4/2004 | Takeda et al. | |
| 2004/0082908 A1 | 4/2004 | Whitehurst et al. | |
| 2004/0106914 A1 | 6/2004 | Coppeta et al. | |
| 2004/0115128 A1 | 6/2004 | Schnitzer | |
| 2004/0120827 A1 | 6/2004 | Kim et al. | |
| 2004/0121486 A1 | 6/2004 | Uhland et al. | |
| 2004/0127844 A1 | 7/2004 | Flaherty | |
| 2004/0133188 A1 | 7/2004 | Vardi et al. | |
| 2004/0137300 A1 | 7/2004 | Gemmen et al. | |
| 2004/0147906 A1 | 7/2004 | Voyiazis et al. | |
| 2004/0166140 A1 | 8/2004 | Santini, Jr. et al. | |
| 2004/0186576 A1 | 9/2004 | Biscup et al. | |
| 2004/0193144 A1 | 9/2004 | Krumme | |
| 2004/0193166 A1 | 9/2004 | Biscup | |
| 2004/0204744 A1* | 10/2004 | Penner et al. | 607/23 |
| 2004/0210184 A1 | 10/2004 | Kost et al. | |
| 2004/0219732 A1 | 11/2004 | Burns et al. | |
| 2004/0220553 A1 | 11/2004 | Olsen | |
| 2004/0223985 A1 | 11/2004 | Dunfield et al. | |
| 2004/0230182 A1* | 11/2004 | Heruth et al. | 604/891.1 |
| 2004/0242976 A1 | 12/2004 | Abreu | |
| 2004/0256584 A1 | 12/2004 | Zimmerling et al. | |
| 2004/0264293 A1* | 12/2004 | Laugharn et al. | 366/127 |
| 2005/0016605 A1 | 1/2005 | Sherman et al. | |
| 2005/0037075 A1 | 2/2005 | Farokhzad et al. | |
| 2005/0055014 A1* | 3/2005 | Coppeta et al. | 604/890.1 |
| 2005/0096587 A1 | 5/2005 | Santini, Jr. et al. | |
| 2005/0119733 A1 | 6/2005 | Wiliams et al. | |
| 2005/0123563 A1 | 6/2005 | Doranz et al. | |
| 2005/0143802 A1 | 6/2005 | Soykan et al. | |
| 2005/0181366 A1 | 8/2005 | Ostermeier | |
| 2005/0187515 A1 | 8/2005 | Varrichio et al. | |
| 2005/0187677 A1 | 8/2005 | Walker | |
| 2005/0191194 A1 | 9/2005 | Falk et al. | |
| 2005/0191708 A1 | 9/2005 | Saul et al. | |
| 2005/0192637 A1 | 9/2005 | Girouard et al. | |
| 2005/0234431 A1* | 10/2005 | Williams et al. | 604/890.1 |
| 2005/0267440 A1 | 12/2005 | Herman et al. | |
| 2006/0004417 A1 | 1/2006 | Rossing et al. | |
| 2006/0089751 A1 | 4/2006 | Herbst | |
| 2006/0116641 A1 | 6/2006 | Gordon et al. | |
| 2006/0149321 A1 | 7/2006 | Merry et al. | |
| 2006/0201432 A1 | 9/2006 | Pratt | |
| 2006/0224128 A1 | 10/2006 | Lurvey et al. | |
| 2006/0241747 A1 | 10/2006 | Shaoulian et al. | |
| 2006/0283465 A1 | 12/2006 | Nickel et al. | |
| 2007/0016171 A1 | 1/2007 | Podvin et al. | |
| 2007/0074722 A1 | 4/2007 | Giroux et al. | |
| 2007/0078445 A1 | 4/2007 | Malloy | |
| 2007/0104023 A1 | 5/2007 | Hood et al. | |
| 2007/0106269 A1 | 5/2007 | Hood et al. | |
| 2007/0106270 A1 | 5/2007 | Hood et al. | |
| 2007/0106271 A1 | 5/2007 | Hood et al. | |
| 2007/0106281 A1 | 5/2007 | Hood et al. | |
| 2007/0135797 A1 | 6/2007 | Hood et al. | |
| 2007/0135798 A1 | 6/2007 | Hood et al. | |
| 2007/0135799 A1 | 6/2007 | Hood et al. | |
| 2007/0135800 A1 | 6/2007 | Hood et al. | |
| 2007/0135801 A1 | 6/2007 | Hood et al. | |
| 2007/0147170 A1 | 6/2007 | Hood et al. | |
| 2007/0149954 A1 | 6/2007 | Hood et al. | |
| 2009/0018704 A1 | 1/2009 | Hood et al. | |
| 2009/0024114 A1 | 1/2009 | Hood et al. | |
| 2009/0227988 A1 | 9/2009 | Wood, Jr. et al. | |

FOREIGN PATENT DOCUMENTS

| | | |
|---|---|---|
| WO | WO 03/049592 A2 | 6/2003 |
| WO | WO 2005/084273 A3 | 9/2005 |

OTHER PUBLICATIONS

U.S. Appl. No. 11/335,911, Hood et al.
U.S. Appl. No. 11/335,788, Hood et al.
U.S. Appl. No. 11/335,786, Hood et al.
U.S. Appl. No. 11/335,785, Hood et al.
U.S. Appl. No. 11/302,450, Hood et al.
U.S. Appl. No. 11/302,449, Hood et al.
U.S. Appl. No. 11/302,407, Hood et al.
U.S. Appl. No. 11/302,321, Hood et al.
U.S. Appl. No. 11/272,573, Hood et al.
U.S. Appl. No. 11/272,572, Hood et al.
U.S. Appl. No. 11/272,524, Hood et al.
U.S. Appl. No. 11/271,146, Hood et al.
U.S. Appl. No. 11/270,799, Hood et al.
"Artificial Muscle Research Institute"; University of New Mexico; Bearing dates of May 29, 2000 and Oct. 14, 2005, printed on Oct. 21, 2005; pp. 1-7; located at: http://www.unm.edu/~amri/.
Bagnato, Joshua D.; Eilers, Alanna L.; Horton, Robert A.; Grissom, Charles B.; "Synthesis and Characterization of a Cobalamin-Colchicine Conjugate as a Novel Tumor-Targeted Cytotoxin"; The Journal of Organic Chemistry; Bearing dates of 2004 and Jun. 3, 2004, printed on Oct. 21, 2005; pp. 8987-8996 (pp. 1-1); vol. 69, No. 26; American Chemical Society; located at: http://pubs.acs.org/cgi-bin/abstract.cgi/joceah/2004/69/i26/abs/jo049953w.html.

(56) References Cited

OTHER PUBLICATIONS

Barnett, S.B.; Roti, H.D.; Ter Haar, G.R.; Ziskin, M.C.; Maeda K.; "The sensitivity of biological tissue to ultrasound"; ingentaconnect; Ultrasound in Medicine and Biology; printed on Feb. 9, 2006; pp. 1; vol. 23; No. 6; 1997; pp. 805-812(8); located at http://www.ingentaconnect.com/search/article?title=ultrasound+heat . . . .

U.S. Appl. No. 11/521,076, Hood et al.
U.S. Appl. No. 11/505,259, Hood et al.
U.S. Appl. No. 11/482,097, Hood et al.
U.S. Appl. No. 11/474,068, Hood et al.
U.S. Appl. No. 11/450,159, Hood et al.

Boniface, J. Jay; Lyons, Daniel S.; Wettstein, Daniel A.; Allbritton, Nancy L.; Davis, Mark M.; "Evidence for a Conformational Change in a Class II Major Histocompatibility Complex Molecule Occuring in the Same pH Range Where Antigen Binding is Enhanced"; J. Exp. Med.; Bearing dates of Jan. 1996 and Jun. 26, 2005; pp. 119-126; vol. 183; The Rockefeller University Press; located at: http://www.jem.org.

Davison, Brian H.; Adams, M.W.W.; "Characterization of Chemically Modified Enzymes for Bioremediation Reactions"; Final Report: U.S. Department of Energy; Bearing dates of Sep. 22, 2000, Oct. 1, 1996 to Aug. 31, 2000; pp. 1-14.

Diaz, Gonzalo, Dr.; "Ultrasound physics. Differences with X-rays"; drGdiaz.com; Bearing a date of Jan. 14, 1996; pp. 1-6; located at: http://www.drgdiaz.com/tables.shtml; printed on Feb. 23, 2006.

Edelman, E.R.; Kost, J.; Bobeck, H.; Langer, R.; "Regulation of drug release from polymer matrices by oscillating magnetic fields"; Journal of Biomedical Materials Research; Bearing a date of 1985; pp. 67-83; vol. 19; John Wiley and Sons, Inc.

Edwards, David A.; Ben-Jebria, Abdelaziz; Langer, Robert; "Invited Review: Recent advances in pulmonary drug delivery using large, porous inhaled particles"; Journal of Applied Physiology; Bearing a date of 1998, downloaded on Oct. 12, 2005; pp. 379-385; vol. 84 (sic 85), Issue 2; The American Physiological Society; located at: http://jap.physiology.org.

Erion, Mark D.; Van Poelje, Paul D.; MacKenna, Deidre A.; Colby, Timothy J.; Montag, Annika C.; Fujitaki, James M.; Linemeyer, David L.; Bullough, David A.; "Absorption, Distribution, Metabolism, and Excretion: Liver-Targeted Drug Delivery Using HepDirect Prodrugs"; Journal of Pharmacology and Experimental Therapeutics *Fast Forward*; Bearing dates of Aug. 31, 2004 and 2005, printed on Oct. 21, 2005; pp. 1-2; Metabasis Therapeutics, Inc. and American Society for Pharmacology and Experimental Therapeutics; San Diego; located at: http://jpet.aspetjournals.org/cgi/content/abstract/312/2/554.

"Ferrofluids"; Liquidsresearch.com; Bearing a date of 2000, printed on Oct. 21, 2005; pp. 1-1; Liquids Research Limited; located at: http://www.liquidsresearch.com/products/ferro.asp.

"Ferromagnetic SMA Actuator"; MIDÉ; Bearing a date of 2004, printed on Aug. 11, 2005; pp. 1-2; Mide Technology Corporation; located at: http://www.mide.com/pdf_html/FSMAA.htm.

"Filtration and Ultrafiltration Equipment and Techniques"; Membranes.nist.gov; printed on Aug. 12, 2005; pp. 1-14; located at: http://www.membranes.nist.gov/ACSchapter/pellePAGE.html.

Freitas, Jr., Robert A.; "Nanomedicine, vol. I: Basic Capabilities 6.4.1 Acoustic Power Transmission"; 1999 and Feb. 18, 2003; printed on Feb. 9, 2006; pp. 1-4; Landes Bioscience, Georgetown, TX; located at http://www.nanomedicine.com/NMI/6.4.1.htm.

Freitas, Jr., Robert A.; "Nanomedicine, vol. I: Basic Capabilities 7.2.2.1 Acoustic Radiators"; 1999 and Feb. 19, 2003; printed on Feb. 9, 2006; pp. 1-2; Landes Bioscience, Georgetown, TX; located at http://www.nanomedicine.com/NMI/7.2.2.1.htm.

Freitas, Jr., Robert A.; "Nanomedicine, vol. I: Basic Capabilities 7.2.2.2 Free-Tissue Acoustic Channel Capacity"; 1999 and Feb. 19, 2003; printed on Feb. 9, 2006; pp. 1-2; Landes Bioscience, Georgetown, TX; located at http://www.nanomedicine.com/NMI/7.2.2.2.htm.

Grayson, Amy C. Richards; Shawgo, Rebecca S.; Johnson, Audrey M.; Flynn, Nolan T.; Li, Yawen; Cima, Michael J.; Langer, Robert; "A BioMEMS Review: MEMS Technology for Physiologically Integrated Devices"; Proceedings of the IEEE; Bearing dates of 2004 and Jan. 2004; pp. 6-21; vol. 92, No. 1; IEEE.

Grayson, Amy C. R.; Voskerician, Gabriela; Lynn, Aaron; Anderson, James M.; Cima, Michael J.; Langer, Robert; "Differential degradation rates in vivo and in vitro of biocompatible poly(lactic acid) and poly(glycolic acid) homo- and co-polymers for a polymeric drug-delivery microchip"; Journal of Biomaterials Science, Polymer Edition; Bearing a date of 2004; pp. 1281-1304; vol. 15, No. 10; VSP; located at: http://www.vsppub.com.

Grayson, Amy C. Richards; Choi, Insung S.; Tyler, Betty M.; Wang, Paul P.; Brem, Henry; Cima, Michael J.; Langer, Robert; "Multi-pulse drug delivery from a resorbable polymeric microchip device"; Nature Materials; Bearing dates of 2003 and Nov. 2003; pp. 767-772; vol. 2; Nature Publishing Group; located at: http://www.nature.com/naturematerials.

Gu, H; Ho, PL; Tsang, KW; Wang, L; Xu, B; "Using biofunctional magnetic nanoparticles to capture vancomycin-resistant enterococci and other gram-positive bacteria at ultralow concentration"; Journal of the American Chemical Society; Bearing dates of Dec. 24, 2003 and Oct. 18, 2005, printed on Oct. 21, 2005; pp. 15702-15703 (pp. 1-1); vol. 125, No. 51; PubMed; located at: http://www.ncbi.nlm.nih.gov/entrez/query.fcgi?cmd=Retrieve&db=PubMed&list_uids=14677934&dopt=Abstract.

"Hielscher—Ultrasound Technology"; Hielscher: Ultrasound in Sonochemistry; Bearing a date of 1999-2006; pp. 1-2; hielscher ultrasonics gmbh; located at: http://www.hielscher.com/ultrasonics/sonochem_01.htm; printed on Feb. 27, 2006.

Huang, Jinlan; Holt, R. Glynn; Cleveland, Robin O.; Roy, Ronald A.; "Experimental validation of a tractable numerical model for focused ultrasound heating in flow-through tissue phantoms"; J. Acoust. Soc. Am.; Bearing dates of Feb. 27, 2004, Jul. 6, 2004, Jul. 11, 2004, Oct. 2004 and 2004; pp. 2451-2458; vol. 116, No. 4, Pt.1; Acoustical Society of America.

Jacque, David; "Science and Technology: Magnetic Nanoparticles Eyed as Biohazard Treatment"; Argonne News; Bearing a date of Nov. 10, 2003, printed on Oct. 21, 2005; pp. 1-3; located at: http://www.cmt.anl.gov/science-technology/processchem/magnetic-nanoparticles.shtml.

Johnson, Audrey M.; Sadoway, Donald R.; Cima, Michael J.; Langer, Robert; "Design and Testing of an Impedance-Based Sensor for Monitoring Drug Delivery"; Journal of The Electrochemical Society; Bearing a date of 2005; pp. H6-H11; vol. 152, Issue 1; The Electrochemical Society, Inc.

Jonnalagadda, Sriramakamal; Robinson, Dennis H.; "A Bioresorbable, Polylactide Reservoir for Diffusional and Osmotically Controlled Drug Delivery"; AAPS PharmSciTech; Bearing a date of 2000; pp. 1-9; vol. 1, No. 4, Article 29; located at: http://www.pharmscitech.com/.

Kaminski, Michael D.; Rosengart, Axel J.; "Biohazard Detoxification Using Magnetic Nanoparticles"; Argonne National Laboratory and The University of Chicago; located at http://www.cmt.anl.gov/science-technology/processchem/BiohazardDetoxification.pdf.

Kennedy, J.E.; Ter Haar, G.R.; Cranston, D.; "High intensity focused ultrasound: surgery of the future?" ingentaconnect; British Institute of Radiology; printed on Feb. 9, 2006; pp. 1; vol. 76; No. 909; Sep. 2003; pp. 590-599(10); located at http://www.ingentaconnect.com/search/article?title=ultrasound+heat . . . .

Knapp, Louise; "Ironing Out Blood Impurities"; Wired News; Bearing dates of Dec. 8, 2003 and 2005, printed on Oct. 21, 2005; pp. 1-4; Lycos, Inc.; located at: http://www.wired.com/news/print/0,1294,61505,00.html and http://www.wired.com/news/medtech/0,1286,61505,00.html.

Kohane, Daniel S.; Plesnila, Nikolaus; Thomas, Sunu S.; Le, Dean; Langer, Robert; Moskowitz, Michael A.; "Lipid-sugar particles for intracranial drug delivery: safety and biocompatibility"; Brain Research; Bearing a date of 2002; pp. 206-213; vol. 946; Elsevier Science B.V.; located at: http://www.elsevier.com/locate/bres.

Kost, Joseph; Wolfrum, Jackie; Langer, Robert; "Magnetically enhanced insulin release in diabetic rats"; Journal of Biomedical Materials Research; Bearing a date of 1987; pp. 1367-1373; vol. 21; John Wiley and Sons, Inc.

(56) References Cited

OTHER PUBLICATIONS

Kozhevnikov, Ivan V.; "Catalysts for Fine Chemical Synthesis, vol. 2, Catalysis by Polyoxometalates"; Chipsbooks.com; Bearing dates of 2002 and 1998-2006, printed on Oct. 21, 2005; pp. 1-3 (201 pages); vol. 2; Culinary and Hospitality Industry Publications Services; located at: http://www.chipsbooks.com/catcem2.htm.

Krauβ, Robert; Liu, Mario; Reimann, Bert; Richter, Reinhard; Rehberg, Ingo; "Fluid pumped by magnetic stress"; Bearing a date of Jul. 1, 2004; pp. 1-3.

Krauβ, Robert; Liu, Mario; Reimann, Bert; Richter, Reinhard; Rehberg, Ingo; "Fluid pumped by magnetic stress"; Bearing dates of Oct. 11, 2005 and Apr. 4, 2005; pp. 1-3; located at: http://arxiv.org/PS_cache/physics/pdf/0405/0405025.pdf.

Langer, Robert; Peppas, Nicholas A.; "Bioengineering, Food, and Natural Products: Advances in Biomaterials, Drug Delivery, and Bionanotechnology"; AIChE Journal; Bearing a date of Dec. 2003; pp. 2990-3006; vol. 49, No. 12.

Langer, Robert; "Biomaterials in Drug Delivery and Tissue Engineering: One Laboratory's Experience"; Accounts of Chemical Research; Bearing a date of 2000; pp. 94-101; vol. 33, No. 2; American Chemical Society.

Langer, Robert; "Commentary: Transdermal drug delivery: past progress, current status, and future prospects"; Advanced Drug Delivery Reviews; Bearing a date of 2004; pp. 557-558; vol. 56; Elsevier B.V.; located at: http://www.sciencedirect.com and http://www.elsevier.com/locate/addr.

Langer, Robert; "Perspectives: Drug Delivery: Drugs on Target"; Science; Bearing a date of Jul. 6, 2001; pp. 58-59; vol. 293; located at: http://www.sciencemag.org.

Langer, Robert; "Reviews: Drug Delivery and Targeting"; Nature: Therapeutic Horizons; Bearing a date of Apr. 30, 1998; pp. 4-10; vol. 392 Supplement, No. 6679.

Lavan, David A.; Lynn, David M.; Langer, Robert; "Perspectives: Moving smaller in drug discovery and delivery"; Nature Reviews: Drug Discovery; Bearing dates of 2001 and Jan. 2002; pp. 77-84; vol. 1; Macmillan Magazines Ltd; located at: http://www.nature.com/reviews/drugdisc.

Lavan, David A.; McGuire, Terry; Langer, Robert; "Small-Scale Systems for in vivo drug delivery"; Nature Biotechnology: Review; Bearing dates of 2003 and Oct. 2003; pp. 1184-1191; vol. 21, No. 10; Nature Publishing Group; located at: http://www.nature.com/naturebiotechnology.

"Lecture 9. Biochemistry 3521—Fordham University—1999"; BIFC 3521: Lecture; Bearing dates of Feb. 10, 1999, printed on Oct. 24, 2005; pp. 1-11; located at: http://dwb.unl.edu/Teacher/NSF/C10/C10Links/www.fordham.edu/Biochem_3521/lect9/lect9.html.

Li, Yawen; Shawgo, Rebecca S.; Tyler, Betty; Henderson, Paul T.; Vogel, John S.; Rosenberg, Aron; Storm, Phillip B.; Langer, Robert; Brem, Henry; Cima, Michael J.; "In vivo release from a drug delivery MEMS device"; Journal of Controlled Release; Bearing dates of 2004 and Sep. 28, 2004; pp. 211-219; vol. 100; Elsevier B.V.; located at: http://www.sciencedirect.com and http://www.elsevier.com/locate/jconrel.

Lindsey, Keiran; "DMD00 The 2000 Guide to the Membrane Industry"; Bearing a date of Dec. 2000, printed on Aug. 12, 2005; pp. 1-16; Business Communications Company, Inc.; located at: http://www.bccresearch.com/print/membrane_p/DMD00_print.html.

Lurie, Karen; "Instant Armor"; ScienCentral News; Bearing dates of Dec. 4, 2003, Oct. 21, 2005 and 2000-2005, printed on Oct. 21, 2005; pp. 1-3; ScienCentral, Inc.; Located at: http://www.sciencentral.com/articles/view.php3?article_id=218392121&language=english.

"Magnetorheological Fluids"; Liquidsresearch.com; Bearing a date of 2000, printed on Oct. 21, 2005; pp. 1-2; Liquids Research Limited; located at: http://www.liquidsresearch.com/products/magnet.asp.

Maione, Emiliano; Shung, K. Kirk; Meyer, Jr., Richard J.; Hughes, Jack W.; Newnham, Robert E.; Smith, Nadine Barrie; "Transducer Design for a Portable Ultrasound Enhanced Transdermal Drug-Delivery System"; IEEE Transactions on Ultrasonics, Ferroelectrics, and Frequency Control; Bearing dates Oct. 2002, Jun. 22, 2001, May 30, 2002, and 2002; pp. 1430-1436; vol. 49, No. 10; IEEE.

"Membrane"; pp. 1-11.

Myers, Matthew R.; "Effect of pulse characteristics on temperature rise due to ultrasound absorption at a bone/soft-tissue interface"; J. Acoust. Soc. Am.; Bearing dates of Sep. 3, 2004, Feb. 1, 2005, Feb. 2, 2005, May 2005, and 2005; pp. 3281-3287; vol. 117, No. 5; Acoustical Society of America.

Moses, Marsha A.; Brem, Henry; Langer, Robert; "Review: Advancing the field of drug delivery: Taking aim at cancer"; Cancer Cell; Bearing dates of 2003 and Nov. 2003; pp. 337-341; vol. 4; Cell Press.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"Our Technology"; Dynal Invitrogen Corporation; printed on Oct. 21, 2005; pp. 1-3; Dynal Biotech; located at: http://www.dynalbiotech.com/kunder/dynal/dynalpub401.nsf/($A11)/A24F11400EF33100C1256EA60054D9C1?OpenDocument.

Paschke, R; Paetz, C; Mueller, T; Schmoll, HJ; Mueller H; Sorkau, E; Sinn, E; "Biomolecules linked to transition metal complexes—new chances for chemotherapy"; Current Medicinal Chemistry; Bearing dates of Oct. 2003 and Oct. 18, 2005, printed on Oct. 24, 2005; pp. 2033-2044 (pp. 1-2); vol. 10, No. 19; PubMed; located at: http://www.ncbi.nlm.nih.gov/entrez/query.fcgi?cmd=Retrieve&db=PubMed&list_uids=12871101&dopt=Abstract.

Prausnitz, Mark R.; Mitragotri, Samir; Langer, Robert; "Reviews: Current Status and Future Potential of Transdermal Drug Delivery"; Nature Reviews: Drug Discovery; Bearing a date of Feb. 2004; pp. 115-124; vol. 3; located at: http://www.nature.com/reviews/drugdisc.

Profunser, D.M.; Vollmann, J.; Dual, J.; "Determination of the material properties of microstructures by laser based ultrasound"; Ultrasonics; Bearing a date of 2004; pp. 641-646; vol. 42; Elsevier B.V.; located at: www.elsevier.com/locate/ultras and at: www.sciencedirect.com.

Puccetti, L; Fasolis, G; Vullo, D; Chohan, ZH; Scozzafava, A; Supuran, CT; "Carbonic anhydrase inhibitors. Inhibition of cytosolic/tumor-associated carbonic anhydrase isozymes I, II, IX, and XII with Schiff's bases incorporating chromone and aromatic sulfonamide moieties, and their zinc complexes"; Bioorganic & Medicinal Chemistry Letters; Bearing dates of Jun. 15, 2005 and Oct. 18, 2005, printed on Oct. 24, 2005; pp. 3096-3101 (pp. 1-2); vol. 15, No. 12; PubMed; located at: http://www.ncbi.nlm.nih.gov/entrez/query.fcgi?cmd=Retrieve&db=pub . . . .

"Quantitative Physiology: Cells and Tissues-Lecture 6"; Bearing a date of Sep. 20, 2004; pp. 1-6; vol. 1: 4.1-4.3.2.3; 4.4-4.5.1.2; located at: http://umech.mit.edu/6.021J/2004/lectures/lec06hi.pdf.

Razansky, Daniel; Einziger, Pinchas D.; Adam, Dan R.; "Enhanced Heat Deposition Using Ultrasound Contrast Agent—Modeling and Experimental Observations"; IEEE Transactions on Ultrasonics, Ferroelectrics and Frequency Control; Bearing dates of Jan. 2006 and 2006; pp. 137-147; vol. 53, No. 1; The Institute of Electrical and Electronics, Inc.; located at: http://www.ieee-uffc.org/archive/uffc/trans/Toc/abs/06/t0610137.htm "Research/Team 02: Project 2.4: Chemically-switchable magnetic materials for actuators"; MIT Institute for Soldier Nanotechnologies; printed on Oct. 21, 2005; pp. 1-2; located at: http://web.mit.edu/isn/research/team02/project02_04.html.

Robinson, Mark A.; Charlton, Stuart T.; Garnier, Philippe; Wang, Xiang-Tao; Davis, Stanley S.; Perkins, Alan C.; Frier, Malcolm; Duncan, Ruth; Savage, Tony J.; Wyatt, David A.; Watson, Susan A.; Davis, Benjamin G.; "Pharmacology: LEAPT: Lectin-directed enzyme-activated prodrug therapy"; PNAS; Bearing dates of Sep. 24, 2004, Oct. 5, 2004, and 2004, printed on Oct. 21, 2005; pp. 14527-14532 (pp. 1-16); vol. 101, No. 40; National Academy of Sciences; located http://www.pnas.org/cgi/content/full/101/40/14527.

Ross, Jennifer L.; Santangelo, Christian D.; Makrides, Victoria; Fygenson, D. Kuchnir; "Tau induces cooperative Taxol binding to microtubules"; PNAS; Bearing dates of Aug. 31, 2004 and 2004; pp. 12910-12915; vol. 101, No. 35; The National Academy of Sciences of the USA; located at: http://gabriel.physics.ucsb.edu/~deborah/pub/RossPNASv101p12910y04.pdf.

(56) References Cited

OTHER PUBLICATIONS

Safarik, Ivo; Safarikova, Mirka; "Magnetic techniques for the isolation and purification of proteins and peptides"; BioMagnetic Research and Technology; Bearing dates of 2004, Nov. 26, 2004 and 1999-2005, printed on Oct. 21, 2005; pp. 1-21; vol. 2, No. 7; BioMed Central Ltd.; located at: http://www.biomagres.com/content/2/1/7.

Saleh, Khaldon Y.; Smith, Nadine Barrie; "A 63 element 1.75 dimensional ultrasound phased array for the treatment of benign prostatic hyperplasia"; BioMedical Engineering OnLine; Jun. 17, 2005, pp. 1-14; 4:39; BioMed Central Ltd.; located at http://biomedical-engineering-online.com/content/4/1/39.

Santini, Jr., John T.; Richards, Amy C.; Scheidt, Rebecca; Cima, Michael J.; Langer, Robert; "Reviews: Microchips as Controlled Drug-Delivery Devices"; Angewandte Chemie International Edition; Bearing a date of 2000; pp. 2396-2407; vol. 39; Wiley-VCH.

Shahinpoor, M.; Bar-Cohen, Y.; Simpson, J.O.; Smith, J.; "Artificial Muscle Research Institute: Paper: Ionic Polymer-Metal Composites (IPMC) as Biomimetic Sensors, Actuators and Artificial Muscles—A Review"; University of New Mexico; printed on Oct. 21, 2005; pp. 1-28; located at: http://www.unm.edu/~amri/paper.html.

Shahinpoor, Mohsen; Kim, Kwang J; "Ionic polymer-metal composites: I. Fundamentals"; Smart Materials and Structures; Bearing dates of Aug. 7, 2001 and 2001; pp. 819-833; vol. 10; IOP Publishing Ltd; UK.

Shawgo, Rebecca S.; Voskerician, Gabriela; Linh Ho Duc, Hong; Li, Yawen; Lynn, Aaron; Macewan, Matthew; Langer, Robert; Anderson, James M.; Cima, Michael J.; "Repeated in vivo electrochemical activation and the biological effects of microelectromechanical systems drug delivery device"; Journal of Biomedical Materials Research; Bearing dates of 2004 and Oct. 26, 2004; pp. 559-568; vol. 71A; Wiley Periodicals, Inc; located at: http://www.interscience.wiley.com.

Sokka, S D; King, R; Hynynen, K; "MRI-guided gas bubble enhanced ultrasound heating in in vivo rabbit thigh"; Physics in Medicine and Biology; Bearing a date of 2003; pp. 223-241; vol. 48; Institute of Physics Publishing.

Sridhar, J; Wei, ZL; Nowak, I; Lewin, NE; Ayres, JA; Pearce LV; Blumberg, PM; Kozikowski, AP; "New bivalent PKC ligands linked by a carbon spacer: enhancement in binding affinity"; J Med Chem.; Bearing dates of Sep. 11, 2003 and Oct. 18, 2005, printed on Oct. 24, 2005; pp. 4196-4204 (pp. 1-2); vol. 46, No. 19; PubMed; Located at: http://www.ncbi.nlm.nih.gov/entrez/query.fcgi?cmd=Retrieve &db—PubMed&list_uids=12954072&dopt=Abstract.

Su, Yu-Chuan; Lin, Liwei; "A Water-Powered Micro Drug Delivery System"; Journal of Microelectromechanical Systems; Bearing dates of 2004 Feb. 2004; pp. 75-82; vol. 13, No. 1; IEEE.

Theeuwes, F.; Yum, S.I.; "Principles of the Design and Operation of Generic Osmotic Pumps for the Delivery of Semisolid or Liquid Drug Formulations"; Annals of Biomedical Engineering; Bearing a date of Dec. 1976 and 1976; pp. 343-353; vol. 4, No. 4; Academic Press, Inc.

Tsutsui, Jeane M.; Xie, Feng; Porter, Richard Thomas; "The use of microbubbles to target drug delivery"; Cardiovascular Ultrasound; Nov. 16, 2004; pp. 1-7; 2:23; BioMed Central Ltd.; located at http://www.cardiovascularultrasound.com/content/2/1/23.

"UCL Mechanical Engineering: Microbubble Ultrasound Contrast Agents"; Mechanical Engineering—UCL; pp. 1-2; UCL; located at: www.mecheng.ucl.ac.uk/research/structural-integrity-materials/ultrasonics/?project=microbubble-ultrasound; printed on Mar. 3, 2006.

Vaezy, Shahram; Martin, Roy; Crum, Lawrence; "Acoustic surgery"; Physics World—Physics Web; pp. 1-8; Bearing dates of Aug., 2001, 1996-2006; located at: http://physicsweb.org/articles/world/14/8/10; printed on Feb. 23, 2006.

Vinatoru, M.; Stavrescu, R.; Milcoveanu, A.B.; Toma, M.; Mason, T.J.; "The ultrasonically induced reaction of benzoyl chloride with nitrobenzene: an unexpected sonochemical effect and a possible mechanism"; Science Direct—Ultrasonics Sonochemistry; Bearing dates of Oct. 2002, 2006; pp. 1-2; vol. 9, No. 5; located at: http://www.sciencedirect.com/science?_ob=ArticleURL&_udi=B6TW3-45S9MTV-1&_user=4504108&_handle=V-WA-A-W-E-MsSWYVW-UUA-U-AAVVBZCVZC-AAVAEVZWZC-DUYVEBWCC-E-U&_fmt=summary&_coverDate=10%2F31%F2002&_rdoc=4&_orig=browse&_srch=%23toc%235551%232002%23999909994%23335682!&_cdi=5551&view=c&_acct=C000050221&_version=1&_urlVersion=0&_userid=4504108 &md5=7c90db9a390ae6056d1810ca472e8a0; printed on Mar. 7, 2006.

Voskerician, Gabriela; Shive, Matthew S.; Shawgo, Rebecca S.; Von Recum, Horst; Anderson, James M.; Cima, Michael J.; Langer, Robert; "Biocompatibility and biofouling of MEMS drug delivery devices"; Biomaterials; Bearing date of 2003; pp. 1959-1967; vol. 24; Elsevier Science Ltd.; located at: http://www.sciencedirect.com and http://www.elsevier.com/locate/biomaterials.

Voskerician, Gabriela; Shawgo, Rebecca S.; Hiltner, P. Anne; Anderson, James M.; Cima, Michael J.; Langer, Robert; "In Vivo Inflammatory and Wound Healing Effects of Gold Electrode Voltammetry for MEMS Micro-Reservoir Drug Delivery Device"; IEEE Transactions on Biomedical Engineering; Bearing dates of 2004 and Apr. 2004; pp. 627-635; vol. 51, No. 4; IEEE.

Webb, Andrew G.; Smith, Nadine Barrie; Ellis, D. Scott; O'Brien, Jr., William D.;"'Non-Invasive In-Vivo Temperature Mapping of Ultrasound Heating Using Flourine-Based Magnetic Resonance Imaging Agents"; 1995 IEEE Ultrasonics Symposium; Bearing a date of 1995; pp. 1609-1612; IEEE.

Zrinyi, M.; Barsi, L.; Büki, A.; "Direct Observation of Discrete and Reversible Shape Transition in Magnetic Field Sensitive Polymer Gels"; printed on Oct. 21, 2005; pp. 1-6; located at: http://www.kfki.hu/~cheminfo/hun/olvaso/zrinyi/polymgel.html.

UK Intellectual Property Office Examination Report Under Section 18(3); App. No. GB0809487.2; bearing a date of Oct. 1, 2010; pp. 1-2.

UK Intellectual Property Office Examination Report Under Section 18(3); App. No. GB0809510.1; bearing a date of Oct. 27, 2010; pp. 1-2.

UK Intellectual Property Office Examination Report Under Section 18(3); App. No. GB0809489.8; bearing a date of Oct. 27, 2010; pp. 1-3.

UK Intellectual Property Office Examination Report Under Section 18(3); App. No. GB0809491.4; bearing a date of Oct. 27, 2010; pp. 1-2.

UK Intellectual Property Office Examination Report Under Section 18(3); App. No. GB0809498.9; Jan. 7, 2011 ; 3 pages.

European Patent Office; Extended European Search Report; App. No. EP 06 82 7655; Mar. 11, 2013; pp. 1-10.

UK Intellectual Property Office Examination Report Under Section 18(3); App. No. GB0809489.8; bearing a date of Jul. 25, 2011; pp. 1-2.

Shoji et al.; "Microflow devices and systems"; J. Micromech. Microeng.; bearing a date of 1994; pp. 157-171; vol. 4; IOP Publishing Ltd.

UK Intellectual Property Office Examination Report Under Section 18(3); App. No. GB0809500.2; bearing a date of Jul. 29, 2011; pp. 1.

UK Intellectual Property Office Examination Report Under Section 18(3); App. No. GB0809510.1; bearing a date of Jul. 29, 2011; pp. 1.

UK Intellectual Property Office Examination Report Under Section 18(3); App. No. GB0809491.4; bearing a date of Aug. 4, 2011; pp. 1-2.

UK Intellectual Property Office Examination Report Under Section 18(3); App. No. GB0921925.4; Jun. 9, 2011 ; pp. 1-5.

Japanese Examination Report; App. No. 2008-540179; Oct. 6, 2011; pp. 1-3; no translation provided.

Agarwal, Abhishek K.; Atencia, Javier; Beebe, David J.; Jiang, Hongrui; "Magnetically-driven temperature-controlled microfluidic actuators"; printed on Nov. 9, 2005; pp. 1-5; located at: http://www.unl.im.dendai.ac.jp/INSS2004/INSS2004_papers/OralPresentations/C2.pdf.

Chen, Haitao; Rosengart, Axel J.; Kaminski, Michael D.; Caviness, Patricia L.; Mertz, Carol J.; Balasubramanian, Viji; Ebner, Armin D.; Ritter, James A.; "Achieving and Optimizing Separation of Magnetic Carriers from Pulsatile Blood Flow"; printed on Nov. 9, 2005; pp.

(56) References Cited

OTHER PUBLICATIONS 1-1; Collaborative Investigators for Applied Nanotechnology In Medicine; located at: http://www.cmt.anl.gov/nanomedicine/posters/carrier-separation.pdf.

Chen, Haitao; Kaminski, Michael D.; Rosengart, Axel J.; Ebner, Armin D.; Guy, Sandra G.; Mertz, Carol J.; Caviness, Patricia L.; Ritter, James A.; "Magnetizable Intravascular Stent and Functionalized Magnetic Carriers: A Novel Approach for Noninvasive Yet Targeted Drug Delivery"; printed on Nov. 9, 2005; pp. 1-1; Collaborative Investigators for Applied Nanotechnology In Medicine; located at: http://www.cmt.anl.gov/nanomedicine/posters/stent.pdf.

Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; printed on Nov. 9, 2005; pp. 1-1; Collaborative Investigators for Applied Nanotechnology In Medicine; located at: http://cmtpub.cmt.anl.gov/nanomedicine/posters/sequestration.pdf.

"Deep Heat Ultrasound & Diathermy"; HuP 195; printed on Mar. 9, 2006; pp. 1-42; located at: www.sjsu.edu/depts/hup/gradath/US.ppt.

Kripfgans, Oliver D.; Carson, Paul L.; Fowlkes, J. Brian; "On the Mechanism of Acoustic Droplet Vaporization"; printed on Mar. 9, 2006; pp. 1-4; University of Michigan Health Systems, Ann Arbor, MI.

"Polymer Gel Actuators and Sensors"; web.mit.edu; printed on Nov. 9, 2005; pp. 1-5; located at: http://web.mit.edu/cmse/www/Leeb97.pdf.

Watson, Tim; "Therapeutic Ultrasound"; printed on Mar. 9, 2006; pp. 1-11; located at: http://www.electrotherapy.org/electro/downloads/Therapeutic%20Ultrasound.pdf.

\* cited by examiner

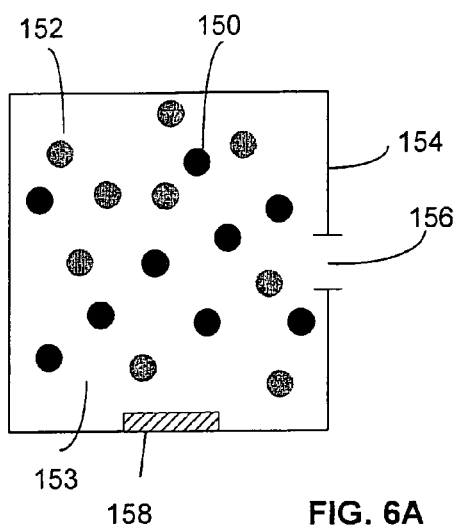
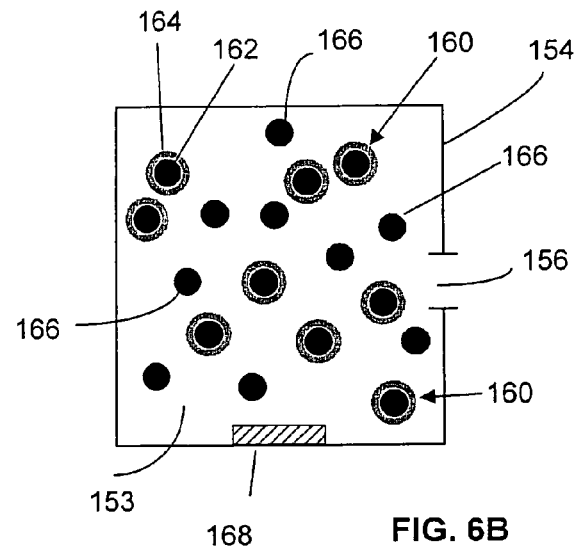
FIG. 6A  FIG. 6B
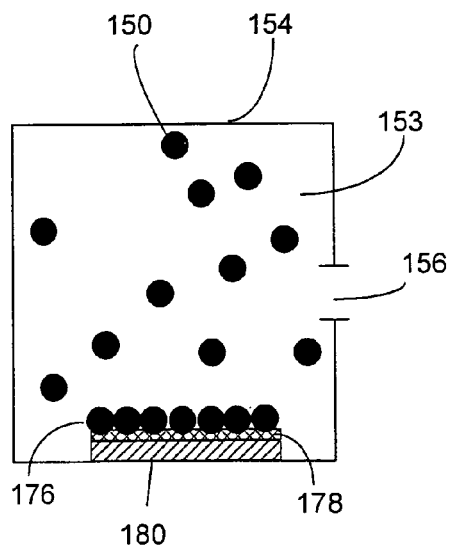
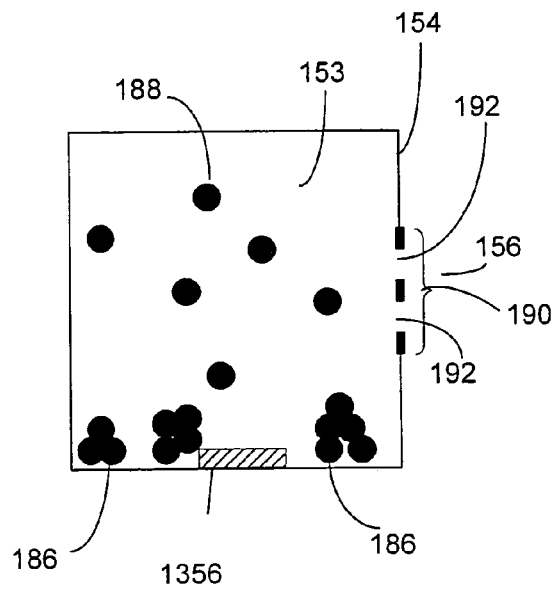
FIG. 6C  FIG. 6D $T_1 > T_2$

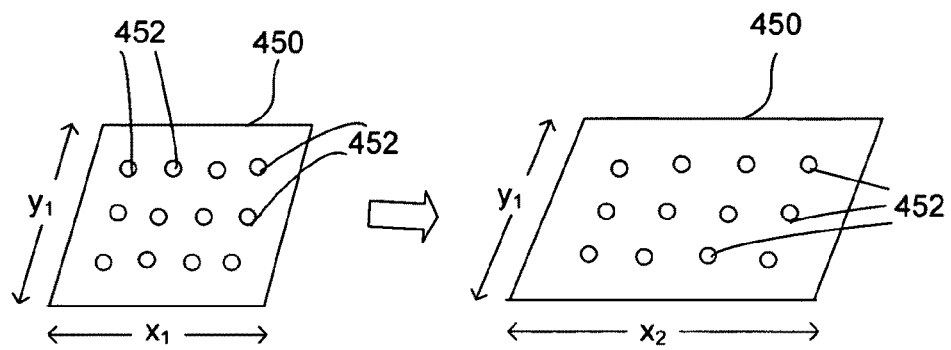
FIG. 12A  FIG. 12B
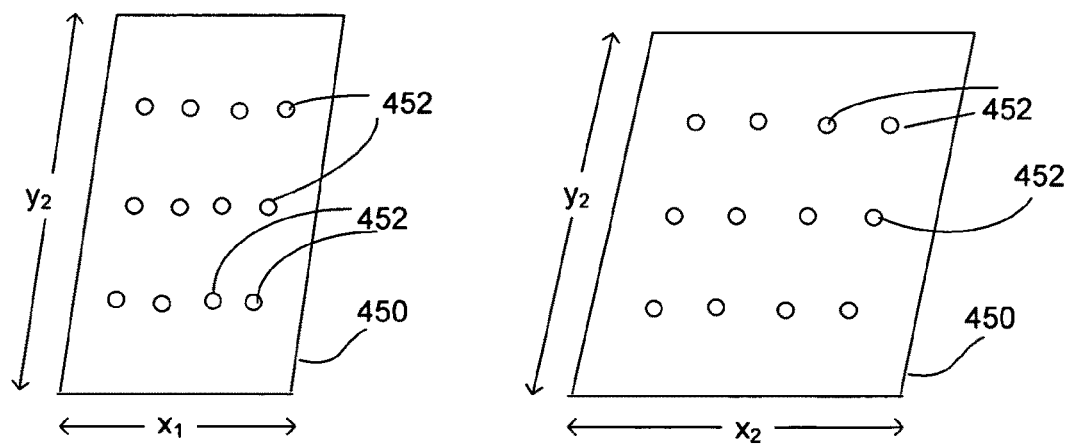
FIG. 12C  FIG. 12D

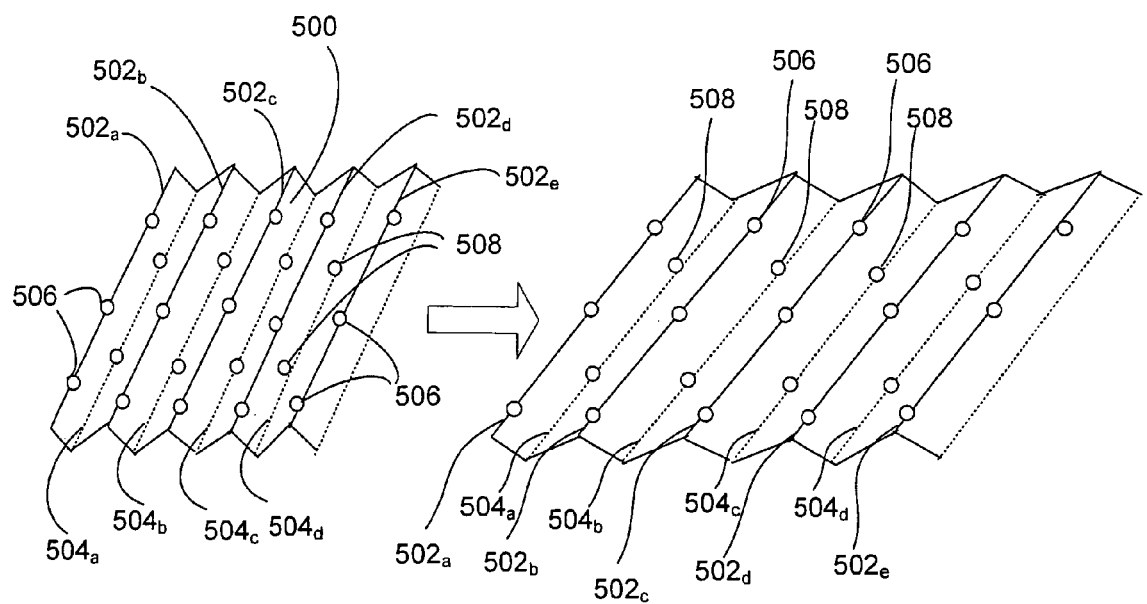
FIG. 13A  FIG. 13B
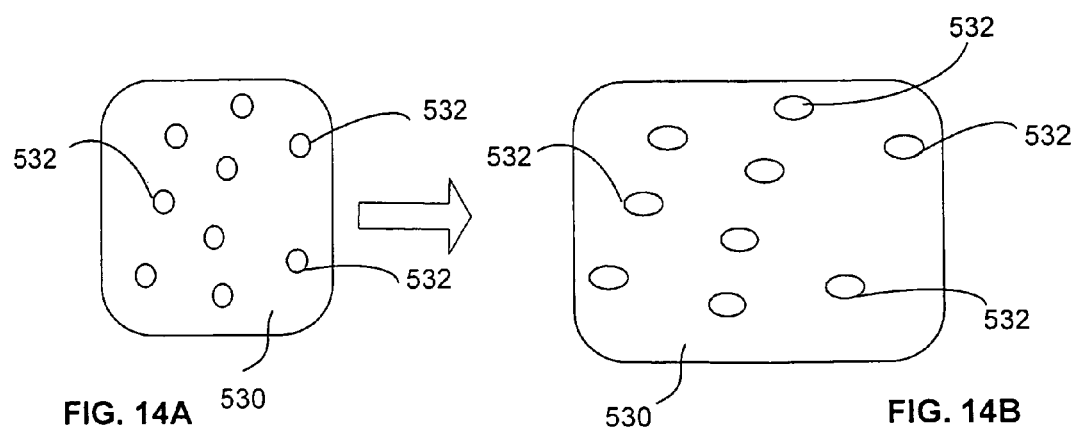
FIG. 14A  FIG. 14B

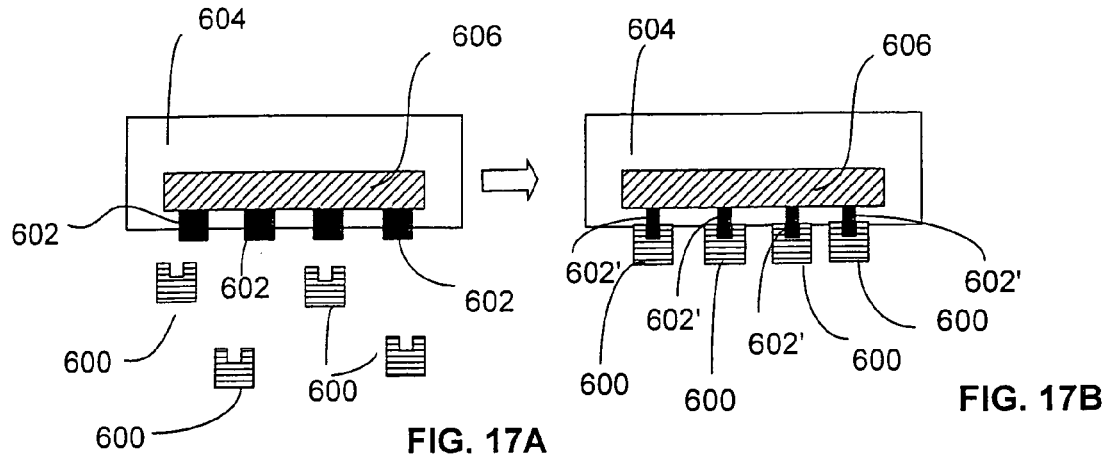
FIG. 17A
FIG. 17B
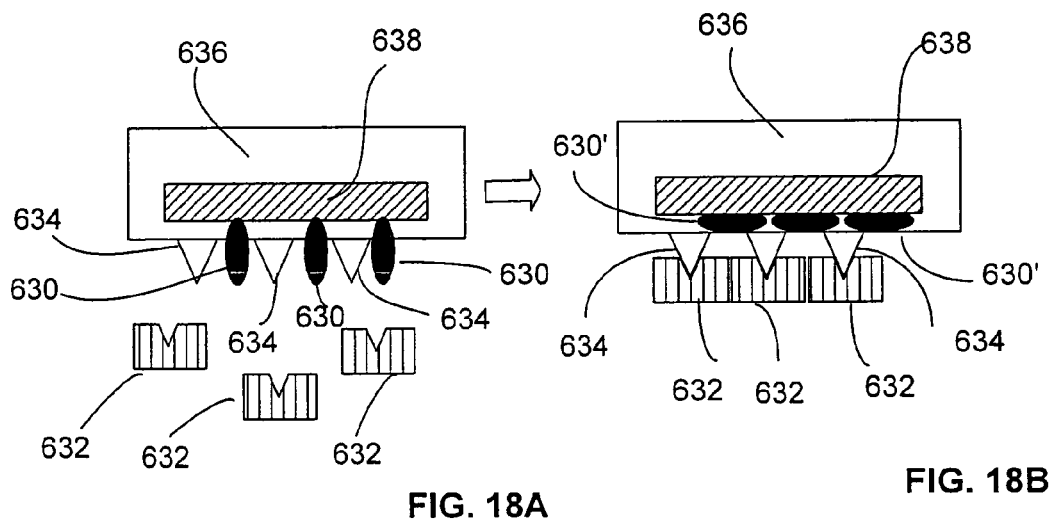
FIG. 18A
FIG. 18B
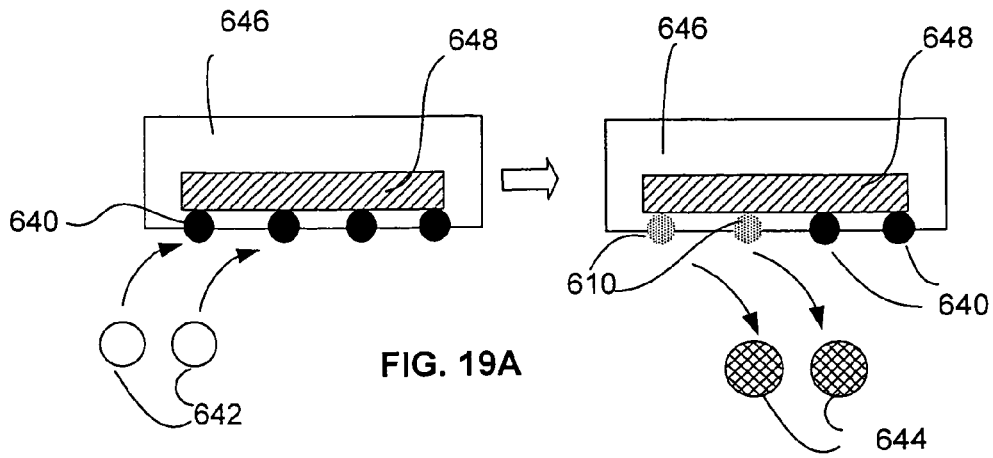
FIG. 19A
FIG. 19B

```
                    ┌─────────┐
                    │  start  │── 1500
                    └────┬────┘
                         ▼
┌────────────────────────────────────────────────────────────────┐
│ Receive an electromagnetic control signal from a remote controller │── 1502
└────────────────────────────┬───────────────────────────────────┘
                             ▼
┌────────────────────────────────────────────────────────────────┐
│ Responsive to the electromagnetic control signal, modify an effective │── 1504
│ concentration of a primary material in a delivery fluid within a delivery reservoir │
└────────────────────────────┬───────────────────────────────────┘
                             ▼
                    ┌─────────┐
                    │   end   │── 1506
                    └─────────┘
```

FIG. 36

```
                    ┌─────────┐
                    │  start  │──── 2350
                    └────┬────┘
                         ▼
┌─────────────────────────────────────────────────────────────────┐
│   Deliver an electromagnetic distribution control signal to an  │
│ environment containing a delivery device, the delivery device   │
│ including an electromagnetically responsive control element and │
│ a fluid-containing structure containing a delivery fluid and a  │
│ quantity of a primary material distributed between a first      │
│ active form carried in the delivery fluid and a second form     │
│ according to a first distribution, the primary material         │
│ distributed according to the first distribution having a first  │
│ effective concentration in the delivery fluid equal             │── 2352
│ to the concentration of the first active form in the delivery   │
│ fluid, the electromagnetic distribution control signal having   │
│ signal characteristics receivable by the electromagnetically    │
│ responsive control element and sufficient to produce a change   │
│ in the distribution of the primary material between the first   │
│ active form and the second form to a second distribution, the   │
│ primary material distributed according to the second            │
│ distribution having a second active concentration in the        │
│ delivery fluid                                                  │
└─────────────────────────────┬───────────────────────────────────┘
                              ▼
┌─────────────────────────────────────────────────────────────────┐
│   Deliver an electromagnetic delivery control signal to the     │
│ environment containing the delivery device, the electromagnetic │
│ delivery control signal sufficient to produce pumping of the    │── 2354
│ delivery fluid out of the fluid-containing structure, the       │
│ delivery fluid containing the primary material at the second    │
│ effective concentration in the delivery fluid.                  │
└─────────────────────────────┬───────────────────────────────────┘
                              ▼
                         ┌─────────┐
                         │   end   │──── 2356
                         └─────────┘
```

FIG. 51

```
                    ┌─────────┐
                    │  start  │── 2500
                    └────┬────┘
                         ▼
┌───────────────────────────────────────────────────────────────────┐
│ Receive a first electromagnetic control signal with a first        │
│ electromagnetically responsive control element in a delivery       │──── 2502
│ device, the delivery device including a fluid-containing structure │
│ containing a delivery fluid and a primary material distributed     │
│ between a first active form carried in the delivery fluid and a    │
│ second form, the primary material having a first effective         │
│ concentration in the delivery fluid equal to the concentration of  │
│ the first active form in the delivery fluid                        │
└──────────────────────────────┬────────────────────────────────────┘
                               ▼                                         2504
┌───────────────────────────────────────────────────────────────────┐
│ Responsive to receipt of the first electromagnetic control signal  │
│ by the first electromagnetically responsive control element,       │
│ modify the distribution of the primary material between the first  │
│ active form and the second form, the primary material having a     │
│ second effective concentration in the delivery fluid following     │
│ the modification of the distribution of the primary material       │
│ between the first active form and the second form                  │
└──────────────────────────────┬────────────────────────────────────┘
                               ▼                                         2506
┌───────────────────────────────────────────────────────────────────┐
│ Pump the delivery fluid containing the primary material at the     │
│ second effective concentration from the fluid-containing structure │
│ of the delivery device to a downstream location.                   │
└──────────────────────────────┬────────────────────────────────────┘
                               ▼
                         ┌─────────┐
                         │   end   │── 2508
                         └─────────┘
```

FIG. 54

```
                    ┌─────────┐
                    │  start  │────── 2600
                    └────┬────┘
                         ↓
┌──────────────────────────────────────────────────────────────────────────────┐
│ Receive a first electromagnetic control signal with a first electromagnetically responsive control │
│ element in a delivery device, the delivery device including a fluid-containing structure containing │
│ a delivery fluid and a primary material distributed between a first active form carried in the │
│ delivery fluid and a second form, the primary material having a first effective concentration in the │
│ delivery fluid equal to the concentration of the first active form in the delivery fluid  2602 │
└──────────────────────────────────────────────────────────────────────────────┘
                         ↓
┌──────────────────────────────────────────────────────────────────────────────┐
│ Responsive to receipt of the first electromagnetic control signal by the first electromagnetically │
│ responsive control element, modify the distribution of the primary material between the first │
│ active form and the second form, the primary material having a second effective concentration in │
│ the delivery fluid following the modification of the distribution of the primary material between │
│ the first active form and the second form  2604 │
│                                                                              │
│  ┌──────────────────┐  ┌──────────────────┐  ┌──────────────────────┐      │
│  │ Modify the distribution of │ │ Modify the distribution of │ │ Modify the distribution of │   │
│  │ primary material in response │ │ primary material in response │ │ primary material in │   │
│  │ to receipt of the first │ │ to receipt of the first │ │ response to receipt of the │   │
│  │ electromagnetic control │ │ electromagnetic control │ │ first electromagnetic │   │
│  │ signal by modifying a │ │ signal by modifying a │ │ control signal by │   │
│  │ pressure within the fluid │ │ temperature within the fluid │ │ modifying a volume of │   │
│  │ containing structure  2608a │ │ containing structure  2608b │ │ the fluid containing │   │
│  │                  │ │                  │ │ structure  2608c │   │
│  └──────────────────┘  └──────────────────┘  └──────────────────────┘      │
│                                                                              │
│  ┌──────────────────┐ ┌──────────────────┐ ┌──────────────────────────┐    │
│  │ Modifying the distribution │ │ Includes modifying the │ │ Modify the distribution of primary │ │
│  │ of primary material in │ │ distribution of primary │ │ material in response to receipt of │ │
│  │ response to receipt of the │ │ material in response to │ │ the first electromagnetic control │ │
│  │ first electromagnetic │ │ receipt of the first │ │ signal by modifying a number of │ │
│  │ control signal by │ │ electromagnetic control │ │ available interaction sites within │ │
│  │ producing vibration within │ │ signal by producing │ │ the fluid containing structure, the │ │
│  │ the fluid containing │ │ fluid mixing within the │ │ available interaction sites capable │ │
│  │ structure  2608d │ │ fluid containing │ │ of interacting with the primary │ │
│  │                  │ │ structure  2608e │ │ material to produce the second │ │
│  │                  │ │                  │ │ form of the primary material  2608f │ │
│  └──────────────────┘ └──────────────────┘ └──────────────────────────┘    │
└──────────────────────────────────────────────────────────────────────────────┘
                         ↓
┌──────────────────────────────────────────────────────────────────────────────┐
│ Pump the delivery fluid containing the primary material at the second effective concentration from │
│ the fluid-containing structure of the delivery device to a downstream location.   2606 │
└──────────────────────────────────────────────────────────────────────────────┘
                         ↓
                    ┌─────────┐
                    │   end   │────── 2610        FIG. 56
                    └─────────┘
```

```
start  2700
  │
  ▼
```

2702 Generate an electromagnetic control signal including frequency components absorbable by an electromagnetically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the electromagnetically responsive control element

2704 Remotely transmit the electromagnetic control signal to the delivery device with signal characteristics sufficient to activate the electromagnetically responsive control element in the delivery device to control the effective concentration of primary material in the delivery fluid in the delivery device.

end  2706

FIG. 58 start 2750

2752

Generate an electromagnetic control signal including frequency components absorbable by an electromagnetically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the electromagnetically responsive control element Generate the electromagnetic control signal and transmitting the electromagnetic control signal to the delivery device with a remote controller 2756a Generate the electromagnetic control signal and transmitting the electromagnetic control signal to the delivery device with two or more remote controllers 2756b Generate the electromagnetic control signal from a model-based calculation 2756c Generate the electromagnetic control signal based on a stored pattern 2756d Generate the electromagnetic control signal based upon a feedback control scheme 2756e

2754

Remotely transmit the electromagnetic control signal to the delivery device with signal characteristics sufficient to activate the electromagnetically responsive control element in the delivery device to control the effective concentration of primary material in the delivery fluid in the delivery device.

end 2758

FIG. 59

```
                    start
                   ┌──────┐─── 2890
                   └──┬───┘        ─── 2892
                      │
                      ▼
┌─────────────────────────────────────────────────────────────────────────┐
│ Receive user input of one or more control parameters                    │
└─────────────────────────────────────────────────────────────────────────┘
                      │
                      │               ─── 2894
                      ▼
┌─────────────────────────────────────────────────────────────────────────┐
│ Based upon the one or more control parameters, generate an electromagnetic control signal │
│ having signal characteristics expected to produce a desired effective concentration of primary │
│ material in the delivery fluid                                          │
└─────────────────────────────────────────────────────────────────────────┘
                      │
                      ▼
                   ┌──────┐
                   │ end  │─── 2896
                   └──────┘
```

FIG. 62

```
                    ┌─────────┐
                    │  start  │────── 2900
                    └─────────┘
                         │
                         ▼
```

| Generate an electromagnetic control signal including frequency components absorbable by an electromagnetically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the electromagnetically responsive control element  2902 |
|---|

| Remotely transmit the electromagnetic control signal to the delivery device with signal characteristics sufficient to activate the electromagnetically responsive control element in the delivery device to control the effective concentration of primary material in the delivery fluid in the delivery device.  2904 |
|---|

Modifying the concentration of the primary material within the delivery fluid in the fluid-containing structure of the delivery device by modifying the area of an interaction region within the fluid containing structure of the delivery device  2906

| Modifying the area of the interaction region includes increasing the area of the interaction region 2906a | | Modifying the area of the interaction region includes decreasing the area of the interaction region 2906b | |
|---|---|---|---|
| The interaction region includes interaction sites, and wherein increasing the area of the interaction region includes increasing the distances between interaction sites in the interaction region 2908a | The interaction region includes interaction sites, and wherein increasing the area of the interaction region includes increasing a number of interaction sites in the reaction 2908b | The interaction region includes interaction sites, and wherein decreasing the area of the interaction region includes decreasing distances between one or more interaction sites in the interaction region 2910a | The interaction region includes interaction sites, and wherein decreasing the area of the interaction region includes decreasing a number of interaction sites in the reaction area 2910b |

```
                    ┌─────────┐
                    │   end   │────── 2912
                    └─────────┘
```

FIG. 63 start 3000

Generate an electromagnetic control signal including frequency components absorbable by an electromagnetically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the electromagnetically responsive control element 3002

Remotely transmit the electromagnetic control signal to the delivery device with signal characteristics sufficient to activate the electromagnetically responsive control element in the delivery device to control the effective concentration of primary material in the delivery fluid in the delivery device. 3004

Modify the concentration of the primary material in the delivery fluid by modifying a condition within the fluid-containing structure. 3006

Modifying a condition within the fluid-containing structure includes modifying the volume of the fluid-containing structure 3008a Modifying a condition within the fluid-containing structure includes heating or cooling at least a portion of the fluid-containing structure 3008b Modifying a condition within the fluid-containing structure includes modifying the osmolality or the pH within at least a portion of the fluid-containing structure 3008c end 3010

FIG. 65 start — 3100

3102

Generate an acoustic control signal including frequency components absorbable by an acoustically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the acoustically responsive control element;

3104

Remotely transmit the acoustic control signal to the delivery device with signal characteristics sufficient to activate the acoustically responsive control element in the delivery device to control the effective concentration of primary material in the delivery fluid in the delivery device.

end — 3106

FIG. 67

```
                    ( start )──── 3150
                         │                      ┌─── 3152
                         ▼
```

Generate an acoustic control signal including frequency components absorbable by an acoustically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the acoustically responsive control element;

| Generate the acoustic control signal from a model-based calculation 3158 | Generate the acoustic control signal based on a stored pattern 3160 | Generate the acoustic control signal based upon a feedback control scheme 3162 |
|---|---|---|

─── 3154

Remotely transmit the acoustic control signal to the delivery device with signal characteristics sufficient to activate the acoustically responsive control element in the delivery device to control the effective concentration of primary material in the delivery fluid in the delivery device.

( end )──── 3156

FIG. 68

```
                    ┌─────────┐
                    │  start  │──── 3200
                    └─────────┘
                         │                              ─── 3202
                         ▼
```

Generate an acoustic control signal including frequency components absorbable by an acoustically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the acoustically responsive control element;

| Receive a feedback signal corresponding to one or more parameters sensed from the environment and, based upon the feedback signal, generate the acoustic control signal with signal characteristics expected to produce a desired feedback signal 3208 | Receive a feedback signal from the delivery device and, based upon the feedback signal, generate the acoustic control signal with signal signal characteristics expected to produce a desired feedback signal 3210 | Receive user input of one or more control parameters, and based upon the one or more control parameters, generate the acoustic control signal with signal characteristics expected to produce a desired effective concentration of primary material in the delivery fluid 3212 |

─── 3204

Remotely transmit the acoustic control signal to the delivery device with signal characteristics sufficient to activate the acoustically responsive control element in the delivery device to control the effective concentration of primary material in the delivery fluid in the delivery device.

end  3206

FIG. 69

ACOUSTICALLY CONTROLLED SUBSTANCE DELIVERY DEVICE

RELATED APPLICATIONS

For purposes of the United States Patent Office (USPTO) extra-statutory requirements, the present application is a DIVISION application of U.S. patent application Ser. No. 11/372,492 titled ACOUSTICALLY CONTROLLED SUBSTANCE DELIVERY DEVICE, naming LEROY E. HOOD, MURIEL Y. ISHIKAWA, EDWARD K. Y. JUNG, ROBERT LANGER, CLARENCE T. TEGREENE, LOWELL L. WOOD, JR. AND VICTORIA Y. H. WOOD as inventors, filed 9 Mar. 2006, which is co-pending, or is an application of which a co-pending application is entitled to the benefit of the filing date. The present application claims the benefit of the earliest available effective filing date(s) (i.e., claims earliest available priority dates for other than provisional patent applications or claims benefits under 35 USC §119(e) for provisional patent applications) for any and all applications to which patent application Ser. No. 11/372,492 claims the benefit of priority, including but not limited to U.S. patent application Ser. No. 11/271,145, titled REACTION DEVICE CONTROLLED BY MAGNETIC CONTROL SIGNAL, naming LEROY E. HOOD, MURIEL Y. ISHIKAWA, EDWARD K. Y. JUNG, ROBERT LANGER, CLARENCE T. TEGREENE, LOWELL L. WOOD, JR. AND VICTORIA Y. H. WOOD as inventors, filed 9 Nov. 2005. U.S. patent application Ser. No. 11/372,492 is a continuation-in-part of U.S. patent application Ser. No. 11/271,145. All subject matter of U.S. patent application Ser. No. 11/372,492 and of any and all applications from which it claims the benefit of the earliest available effective filing date(s) is incorporated herein by reference to the extent such subject matter is not inconsistent herewith. The USPTO has issued new rules regarding claims and Continuations, effective Nov. 1, 2007, 72 Fed. Reg. 46716—21 Aug. 2007, available at: http://www.uspto.gov/web/offices/com/sol/notices/72fr46716.pdf; wherein 37 CFR 1.78(d)(1) states that the USPTO will refuse to enter any specific reference to a prior-filed application that fails to satisfy any of 37 CFR 1.78(d)(1)(i)-(vi). The applicant entity has provided above a specific reference to the application(s) from which priority is being claimed—as required by statute. Applicant entity understands that the statute is unambiguous in its specific reference language and does not require either a serial number or any characterization, such as "continuation" or "continuation-in-part" or "divisional," for claiming priority to U.S. patent applications. Notwithstanding the foregoing, the applicant entity has provided above a specific reference to the application(s) from which priority is being claimed that satisfies at least one of the extra-statutory requirements of 37 CFR 1.78(d)(1)(i)-(vi), but expressly points out that such designations are not to be construed in any way as any type of commentary and/or admission as to whether or not the present application contains any new matter in addition to the matter of its parent application(s). Any designation that the present application is a "division" should not be construed as an admission that the present application claims subject matter that is patentably distinct from claimed subject matter of its parent application.

TECHNICAL FIELD

The present application relates, in general, to the field of devices, systems and/or methods for remotely controlled delivery of materials.

BACKGROUND

Implantable controlled release devices for drug delivery have been developed. Certain devices rely upon the gradual release of a drug from a polymeric carrier over time, due to degradation of the carrier. Polymer-based drug release devices are being developed that include a drug in a ferropolymer that may be heated by an externally applied magnetic field, thus influencing the drug release. MEMS based drug release devices that include integrated electrical circuitry are also under development, as are MEMS based systems for performing chemical reactions. Implantable delivery devices have been developed for drug delivery purposes. Wireless transmission of electromagnetic signals of various frequencies is well known in the areas of communications and data transmission, as well as in selected biomedical applications.

SUMMARY

The present application relates, in general, to the field of fluid delivery devices, systems, and methods. In particular, the present application relates to remotely controlled delivery devices in which the concentration of a material in a fluid to be delivered may be varied. Control signals may be carried between a remote controller and a delivery device in an environment by electrical, magnetic, or electromagnetic fields or radiation. Embodiments of a system including a remotely controlled delivery device and associated controller are described. Methods of use and control of the device are also disclosed. According to various embodiments, a delivery device may be placed in an environment in order to eject or release a material into the environment. Exemplary environments include a body of an organism, a body of water or other fluid, or an enclosed volume of a fluid. According to some embodiments, a delivery device may provide for delivery of a fluid into a downstream fluid-handling structure. The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6A-6D show examples of first active and second forms of primary material in delivery fluid;

FIG. 12A depicts an exemplary interaction region;

FIG. 12B depicts expansion of the interaction region of FIG. 12A in a first direction;

FIG. 12C depicts expansion of the interaction region of FIG. 12A in a second direction;

FIG. 12D depicts expansion of the interaction region of FIG. 12A in first and second directions;

FIGS. 13A and 13B depict unfolding of a pleated interaction region;

FIGS. 14A and 14B depict another embodiment of an interaction region;

FIGS. 17A and 17B depict an exemplary embodiment of an interaction region;

FIGS. 18A and 18B depict another exemplary embodiment of an interaction region;

FIGS. 19A and 19B depict another exemplary embodiment of an interaction region;

FIG. 36 is a flow diagram of a method of delivering a fluid;

FIG. 51 is a flow diagram of a method of delivering a fluid;

FIG. 54 is a flow diagram of another method of delivering a material;

FIG. 56 is a flow diagram of an expansion of the method of FIG. 54;

FIG. 58 is a flow diagram of a method of controlling a delivery device;

FIG. 59 is an expansion of the method of FIG. 58;

FIG. 62 is a flow diagram of further alternative additional steps for controlling a delivery device;

FIG. 63 is a further expansion of the method of FIG. 58;

FIG. 65 is still another expansion of the method of FIG. 58;

FIG. 67 is a flow diagram of a method of controlling a delivery device;

FIG. 68 is a flow diagram showing alternative details of the method shown in FIG. 67; and FIG. 69 is a flow diagram showing further alternative details of the method shown in FIG. 67.

DETAILED DESCRIPTION

Figure 1:
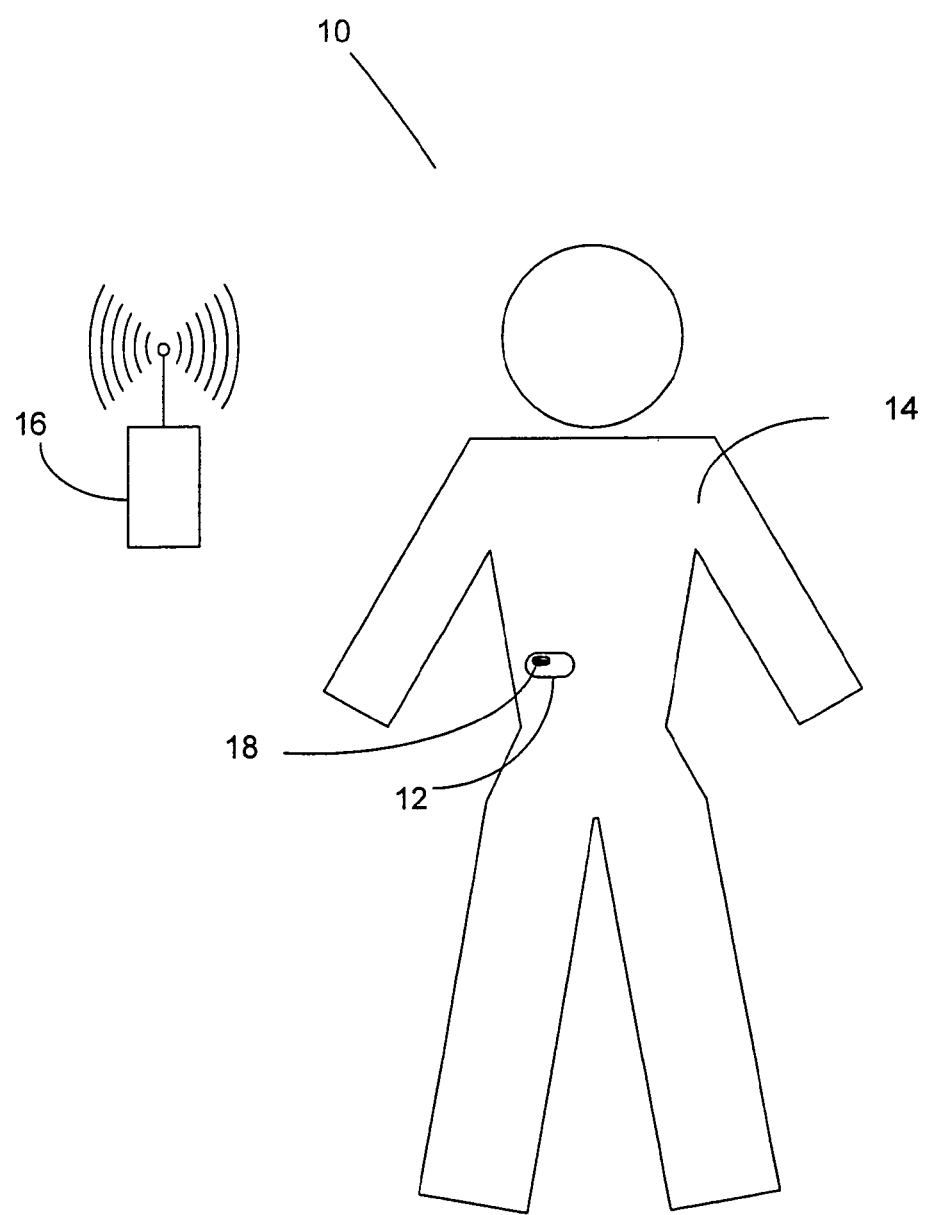
FIG. 1 depicts an embodiment of a delivery system for use in a human subject.

In the following detailed description, reference is made to the accompanying drawings, which form a part hereof. In the drawings, similar symbols typically identify similar components, unless context dictates otherwise. The illustrated embodiments described in the detailed description, drawings, and claims are not meant to be limiting. Other embodiments may be utilized, and other changes may be made, without departing from the spirit or scope of the subject matter presented here.

FIG. 1 depicts a first exemplary embodiment of a delivery system 10. In the embodiment of FIG. 1, delivery system 10 includes delivery device 12 located in an environment 14, (which in this particular example is a human body) and remote controller 16. As used herein, the term "remote" refers to the transmission of information (e.g. data or control signals) or power signals or other interactions between spatially separated devices or apparatuses, such as the remote controller or the delivery system, without a connecting element such as a wire or cable linking the remote controller and the delivery system, and does not imply a particular spatial relationship between the remote controller and the delivery device, which may, in various embodiments, be separated by relatively large distances (e.g. miles or kilometers) or a relatively small distances (e.g. inches or millimeters). Delivery device 12 includes an electromagnetically or acoustically responsive control element 18 that is responsive to an electromagnetic or acoustic control signal generated by remote controller 16.

Figure 2:
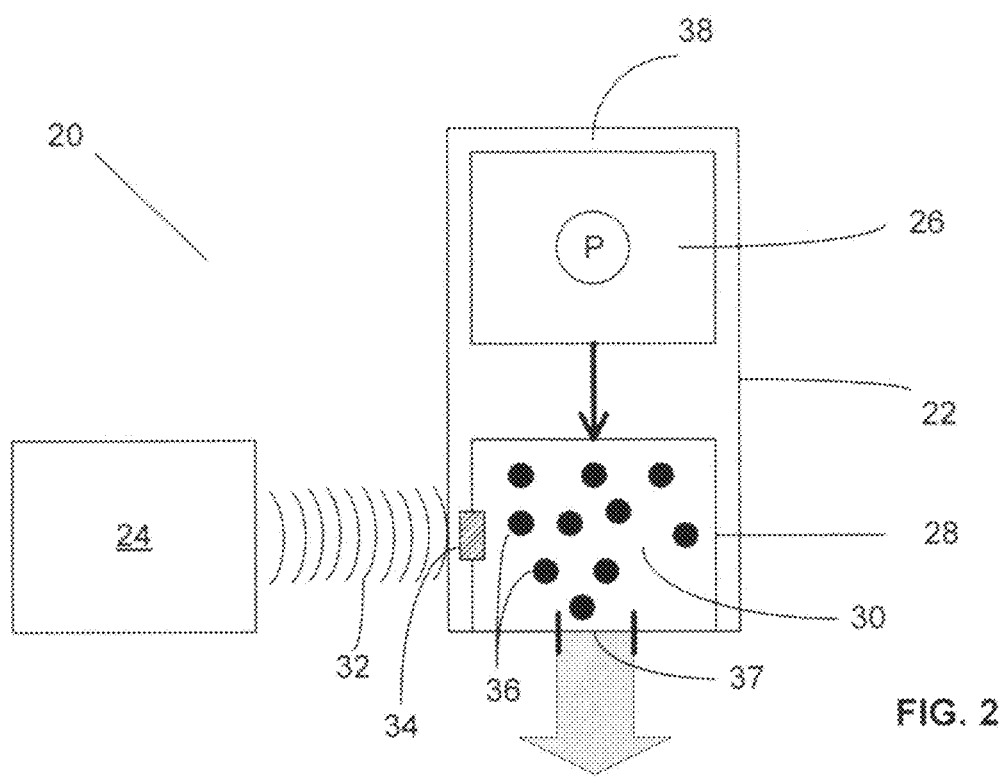
FIG. 2 depicts an embodiment of a delivery system including a remote controller.

FIG. 2 depicts an embodiment of a delivery system 20 including a delivery device 22 controlled by remote controller 24. In the embodiment of FIG. 2, delivery device 22 includes pump 26 and delivery reservoir 28 which contains delivery fluid 30. Remote controller 24 transmits electromagnetic control signal 32 to electromagnetically responsive control element 34 to control the concentration of primary material 36 in delivery fluid 30. Pump 26 pumps delivery fluid 30 containing primary material 36 from delivery reservoir 28 via outlet 37. Delivery device 22 also includes a body structure 38. In this and various other embodiments, as an alternative, the system may utilize an acoustic, rather than electromagnetic, control signal, and an acoustically responsive control element. In this and other embodiments described herein, although a single outlet is depicted, any number of outlets may be used. Moreover, while in some embodiments an outlet may be a simple opening, in others the outlet may include a permeable or semi-permeable membrane, filter or other some structure which permits the exit of delivery fluid (or components of thereof) from the delivery reservoir.

Figure 3:
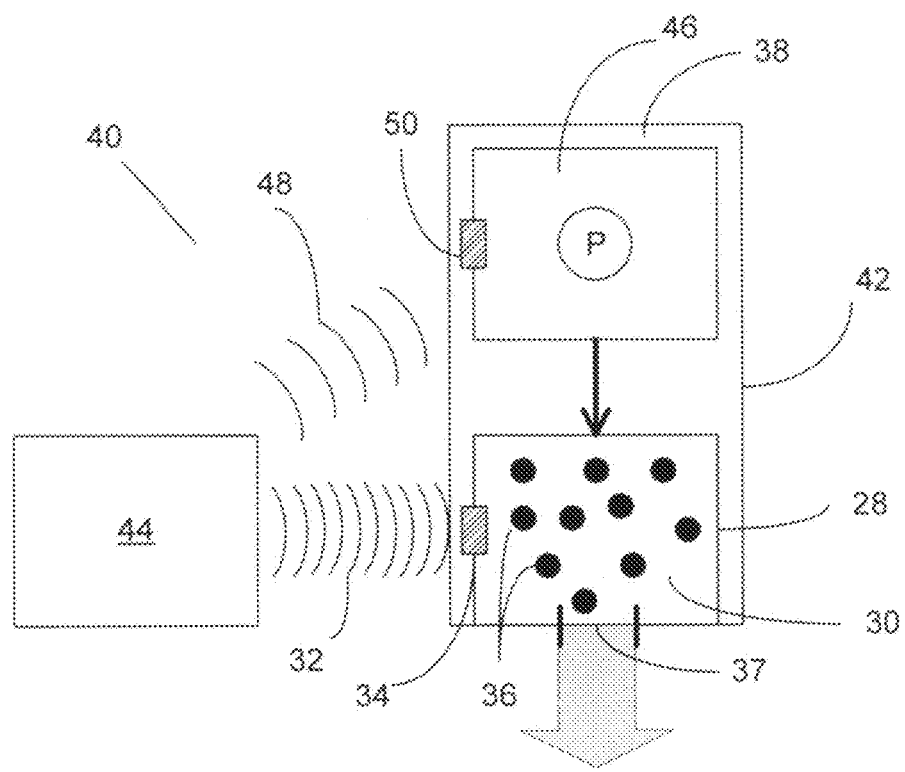
FIG. 3 depicts another embodiment of a delivery system including a remote controller.

FIG. 3 depicts another embodiment of a delivery system 40 including a delivery device 42 controlled by remote controller 44. In the embodiment of FIG. 3, delivery device 42 includes pump 46 and delivery reservoir 28, which contains delivery fluid 30. Remote controller 44 transmits electromagnetic distribution control signal 32 to electromagnetically responsive control element 34 to control the concentration of primary material 36 in delivery fluid 30. Remote controller 44 also transmits electromagnetic delivery control signal 48 to receiving element 50 in pump 46 to control the pumping of delivery fluid 30 from delivery reservoir 28. Outlet 37 and body structure 38 are also included in delivery device 48.

Figure 4A:
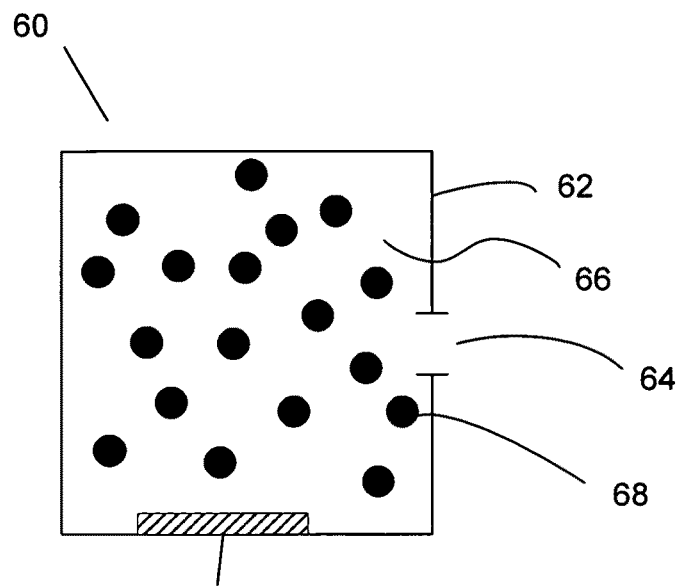
FIGS. 4A and 4B illustrate in schematic form a change in concentration in a fluid to be delivered by an embodiment of a delivery device.
Figure 4B:
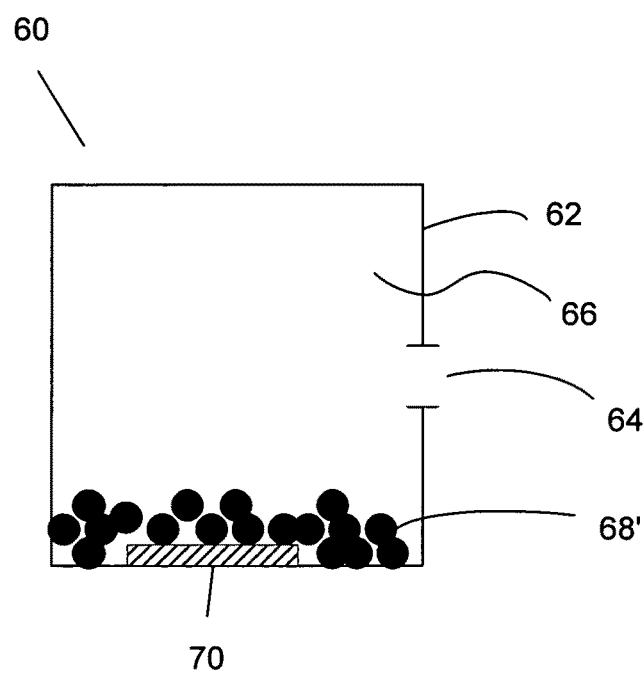

FIGS. 4A and 4B illustrate in schematic form a delivery device 60 comprising a delivery reservoir 62 configured to contain a delivery fluid, the delivery reservoir having at least one outlet 64 through which the delivery fluid may exit the delivery reservoir; a delivery fluid 66 contained within the delivery reservoir 62; a primary material 68 contained within the delivery reservoir 62 and having a controllable effective concentration in the delivery fluid; and at least one electromagnetically responsive control element 70 adapted for modifying the distribution of the primary material between a first active form carried in the delivery fluid and a second form in response to an incident electromagnetic control signal, the effective concentration being the concentration of the first active form in the delivery fluid. Delivery fluid may exit delivery reservoir 66 by diffusion, or by being moved out of delivery reservoir 66 by positive pressure applied to delivery reservoir 62 (e.g. by a pump) or negative pressure generated downstream of delivery reservoir 62. FIG. 4A illustrates a first state of electromagnetically responsive control element 70, which causes primary material 68 to be in a first active form in delivery fluid 66. FIG. 4B illustrates a second state of electromagnetic control element 70, which causes the primary material to be in a second form 68', which is not an active form carried in delivery fluid 66, but may be, for example, insoluble in delivery fluid 66 as depicted in FIG. 4B.

In order to modify the distribution of primary material between the first active form and the second form, the electromagnetically responsive control element used in this and other embodiments (e.g., 34 in FIGS. 2 and 3 or 70 in FIGS. 4A and 4B) may have various functional characteristics. In some embodiments, the electromagnetically responsive control element may include or form a heating element (e.g., a resistive element) or a cooling element (which may be, for example, a thermoelectric device). In some embodiments, the electromagnetically responsive control element may be an expanding element. In some embodiments, an electromagnetically responsive control element may include a receiving element such as an antenna or other geometric gain structure to enhance the receiving of an electromagnetic control signal transmitted from a remote control signal generator. The response of the electromagnetically responsive control element to an electromagnetic field may be due to absorption of energy from the electromagnetic signal or due to torque or traction on all or a portion of the electromagnetically responsive control element due to the electromagnetic field. The response will depend upon the intensity, the relative orientation and the frequency of the electromagnetic field and upon the geometry, composition and preparation of the material of the electromagnetically responsive control element. A response may occur on the macro level, on a microscopic level, or on a nanoscopic or molecular level. In some embodiments, the electromagnetically responsive control element may respond to the control signal by changing shape. In some embodiments, the electromagnetically responsive control element may respond to the control signal by changing in at least one dimension. The response of the electromagnetically responsive control element may include one or more of heating, cooling, vibrating, expanding, stretching, unfolding, contracting, deforming, softening, or folding globally or locally. In some embodiments, the electromagnetically responsive control element may be configured to selectively respond to an electromagnetic field having a specific frequency and orientation. Frequency selectivity may be conferred by appropriate selection of electromagnetically responsive control element size relative to the wavelength of the electromagnetic signal, while directional selectivity may be conferred by the configuration and orientation of the electromagnetically responsive control element.

Electromagnetically responsive control elements used in various embodiments of delivery devices and systems may include one or more electromagnetically active materials. The electromagnetically responsive control element may include a magnetically or electrically active material. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials; examples of electrically active materials include ferroelectrics, piezoelectrics, dielectric materials, including permanently 'poled' dielectrics and dielectrics having both positive and negative real permittivities, and metallic materials.

In some embodiments, the electromagnetically responsive control element may include a hydrogel, ferrogel, or ferroelectric. The electromagnetically responsive control element may include a polymer, ceramic, dielectric, or metal. The electromagnetically responsive control element may include various materials, such as polymers, ceramics, plastics, dielectrics or metals, or combinations thereof. In some embodiments, the electromagnetically responsive control element may include a polymer and a magnetically or electrically active component. In some embodiments, the electromagnetically responsive control element may include a shape memory material such as a shape memory polymer or a shape memory metal, or a composite structure such as a bimetallic structure.

In some embodiments, the remotely activatable control element may be responsive to an acoustic control signal. The remotely activatable control element may respond to the control signal by changing shape. In some embodiments, the remotely activatable control element may respond to the control signal by changing in at least one dimension. The response of the remotely activatable control element may include one or more of heating, cooling, vibrating, expanding, stretching, unfolding, contracting, deforming, softening, or folding globally or locally. The remotely activatable control element may include various materials, such as polymers, ceramics, crystalline materials, or combinations thereof. Effects of acoustic energy applied to a material may include heating or cavitation (formation of gas bubbles due to local reduction in pressure), acoustic torque or streaming, and, at the molecular level, rotation, translation, or vibration. Heating may be produced when acoustic energy is absorbed by a material, rather than being reflected from or transmitted through the material. In body tissues, absorption is relatively lower in tissues having high water content, and relatively higher in tissues having high protein content. Higher heating may be obtained the interface of materials having different acoustic impedances, for example, at soft tissue-bone interface. Reflection of acoustic energy at interfaces may lead to standing waves or hot spots; and the larger the difference in acoustic impedance at an interface between two materials or tissues, the more energy will be reflected at the interface. Higher levels of heating may be obtained at gas bubbles than in surrounding fluid/tissue. Materials that may respond to an acoustic signal by producing an electrical signal include piezoelectric materials, including natural crystals such as quartz, as well as synthetic ceramics such a lead zirconate titanate (e.g., PZT-4, PZT-8), lead zirconate, lead titanate, barium titanate, nickel cobalt, and ceramic/polymer composites. Moreover, response to acoustic signals may be indirect, as well. For example, a MEMS structure may respond by physically deforming responsive to an acoustic signal. Known structures can convert deformation in MEMS structures to electrical or other signals. For example, piezoresistive structures may be integral to or coupled to a deforming region of a MEMS structure. In still another approach, capacitive or inductive coupling between a deforming region and additional electrical circuitry or movement of a magnetic material relative to a conductor can produce electrical signals responsive to an acoustic signal, in some cases similarly to a microphone transducer. Papers describing heating effects of ultrasound include "Experimental validation of a tractable numerical model for focused ultrasound heating in flow through tissue phantom," Huang et al., J. Acoust. Soc. Am. 116(4), Pt. 1, October 2004, "Effect of pulse characteristics on temperature rise due to ultrasound absorption at a bone/soft tissue interface," Myers, J. Acoust. Soc. Am. 117(5), May 2005, and "MRI guided gas bubble enhanced ultrasound heating in the in vivo rabbit thigh," Sokka et al., Phys. Med. Biol. 48 (2003): 223-241, all of which are incorporated herein by reference. An example of a paper in which increased chemical reactivity of chemical compounds caused by exposure to ultrasound is reported is "The ultrasonically induced reaction of benzoyl chloride with nitro benzene: an unexpected sonochemical effect and a possible mechanism," Vinatoru et al., Ultrasonics Sonochemistry Vo. 9, No. 5, October 2002, pp. 245-249, which is also incorporated herein by reference.

In some embodiments, the electromagnetically responsive control element may include a polymer and an electrically active component (including highly polarizable dielectrics) or a magnetically active component (including ferropolymers and the like). In embodiments in which the electromagnetically responsive control element includes one or more electrically or magnetically active components, the electrically or magnetically active component may respond to an electromagnetic control signal in a first manner (e.g., by heating) and the response of the electromagnetically responsive control element may be produced in response to the electrically or magnetically active component (e.g. expansion or change in shape in response to heating of the electrically or magnetically active component). Electromagnetically responsive control elements may, in some embodiments, be composite structures. Heating may be produced in response to acoustic (e.g. ultrasound) signals rather than electromagnetic signals in selected embodiments.

Figure 5:
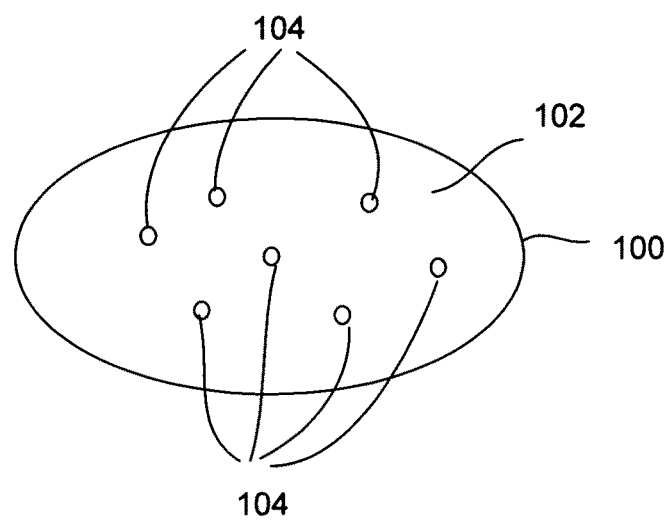
FIG. 5 depicts an electromagnetically responsive control element including a polymer and magnetically or electrically active components.

FIG. 5 depicts an example of an electromagnetically responsive control element 100 including a composite structure formed from a polymer 102 and multiple electrically or magnetically active components in the form of multiple particles 104 distributed through polymer 102. In some embodiments, the electrically or magnetically active components may be heatable by the electromagnetic control signal, and heating of the electrically or magnetically active components may cause the polymer to undergo a change in configuration. An example of a magnetically responsive polymer is described, for example, in Neto, et al, "Optical, Magnetic and Dielectric Properties of Non-Liquid Crystalline Elastomers Doped with Magnetic Colloids"; Brazilian Journal of Physics; bearing a date of March 2005; pp. 184-189; Volume 35, Number 1, which is incorporated herein by reference. Other exemplary materials and structures are described in Agarwal et al., "Magnetically-driven temperature-controlled microfluidic actuators"; pp. 1-5; located at: http://www.unl.im.dendai.ac.jp/INSS2004/INSS2004_papers/OralPresentations/C2.pdf or U.S. Pat. No. 6,607,553, both of which are incorporated herein by reference. Similar composite structures may be formed with an acoustically responsive material and a polymer.

As mentioned in connection with FIGS. 2-4B, the delivery device may contain a primary material (the material that is intended to be delivered to an environment or other downstream location) in a delivery fluid. The primary material may be distributed between a first active form (in which it is usable or active) and a second form in which it is inactive, inaccessible, or otherwise unavailable or unusable). The first active form of the primary material may be carried in solution, in suspension, in emulsion, or in colloidal suspension in the delivery fluid, so that it may be delivered from the delivery device along with the delivery fluid. In some embodiments, the second form may be an inactive form of the primary material, which may be carried in the delivery fluid along with the first active form. The second form may be carried in the delivery fluid in solution, in suspension, in emulsion, or in colloidal dispersion, for example.

In some such embodiments, the second form may be a chemically inactive form. This case is depicted in FIG. 6A, in which the first active form is indicated by reference number 150, and the second (chemically inactive) form is indicated by reference number 152. Delivery reservoir 154, including outlet 156 and electromagnetically responsive control element 158 are also indicated. Both first active form 150 and second form 152 are carried in delivery fluid 153.

In other embodiments, as illustrated in FIG. 6B, the second form 160 may include a chemically active form of the primary material 162 contained in a carrier structure 164, while the first active form 166 is not contained in a carrier structure. The carrier structure may be, for example, a capsule, microcapsule, micelle, or fullerene, or other carrier structure known to those of skill in the relevant art. Delivery reservoir 154 includes outlet 156 and electromagnetically responsive control element 168.

In still other embodiments, as illustrated in FIG. 6C, the second form 176 may be bound or associated with an interaction region 178 in the delivery reservoir 154, while the first active form 150 is carrier in delivery fluid 153. Interaction of second form 176 with interaction region 178 may be controlled by electromagnetically responsive control element 180.

As shown in FIG. 6D, in some embodiments, the second form 186 may be insoluble in the delivery fluid 153; for example, the second form 186 may be precipitated out of the delivery fluid while first active form 188 is carried in delivery fluid 153. As illustrated in FIG. 6D, the delivery reservoir 154 may include filter 190 located between the delivery reservoir 154 and the outlet 156 and configured for removing the second form 186 from the delivery fluid 153. For example, openings 192 in filter 190 may be large enough to allow first form 188 to pass through, but too small to allow precipitated second form 186 to pass through the filter. In other embodiments, the filter may operate based upon increased affinity for the second form over the first active form, or other filtering principle, as is well known in the field of filtration. The term 'filter' is intended to encompass various types of materials-separating device.

The primary material may have a different immunogenicity, reactivity, stability, or activity when it is in the first active form than when it is in the second form. The primary material may be any of a wide variety of materials, including single materials or mixtures of materials. For example, the primary material may be a pharmaceutical material or a neutraceutical material. The primary material may be a biologically active material. In some embodiments, the primary material may include at least one nutrient, hormone, growth factor, medication, therapeutic compound, enzyme, genetic material, vaccine, vitamin, neurotransmitter, cytokine, cell-signaling material, pro- or anti-apoptotic agent, imaging agent, labeling agent, diagnostic compound, nanomaterial, inhibitor, or blocker. In some embodiments, the primary material may be a component or precursor of a biologically active material; for example, the primary material may include at least one precursor or component of a nutrient, hormone, growth factor, medication, therapeutic compound, enzyme, genetic material, vaccine, vitamin, neurotransmitter, cytokine, cell-signaling material, pro- or anti-apoptotic agent, imaging agent, labeling agent, diagnostic compound, nanomaterial, inhibitor, or blocker. Such precursors, may include, for example, prodrugs (see, e.g., "Liver-Targeted Drug Delivery Using HepDirect1 Prodrugs," Erion et al., Journal of Pharmacology and Experimental Therapeutics Fast Forward, JPET 312:554-560, 2005 (first pub Aug. 31, 2004) and "LEAPT: Lectin-directed enzyme-activated prodrug therapy", Robinson et al., PNAS Oct. 5, 2004 vol. 101, No. 40, 14527-14532, published online before print Sep. 24, 2004 (http://www.pnas.org/cgi/content/full/101/40/14527), both of which are incorporated herein by reference. Beneficial materials may be produced, for example, by conversion of pro-drug to drug, enzymatic reaction of material in bloodstream (CYP450, cholesterol metabolism, e.g., with cholesterol monooxygenase, cholesterol reductase, cholesterol oxidase). Depending on the intended application or use environment for the delivery device, the primary material may include at least one fertilizer, nutrient, remediation agent, antibiotic, microbicide, herbicide, fungicide, transfection agent, nanomaterial, disinfectant, metal salt, a material for adjusting a chemical composition or pH, such as buffer, acid, base, chelating agent, emulsifying agent, or surfactant. In some embodiments, the primary material may include a tissue-specific marker or targeting molecule, which may be, for example, a tissue-specific endothelial protein. A tissue-specific marker or targeting molecule may assist in targeting of the primary material to a specific location or tissue within a body of an organism.

The term "delivery fluid" as used herein, is intended to cover materials having any form that exhibits fluid or fluid-like behavior, including liquids, gases, powders or other solid particles in a liquid or gas carrier. The delivery fluid may be a solution, suspension, or emulsion.

Typically, the effective concentration of the primary material will be the concentration of the first active form of the primary material in the delivery fluid, which may differ from the total concentration of primary material in the delivery fluid, which is the combined concentration of both the first active and second forms of the primary material. The effective rate of delivery of primary material from the delivery device will generally equal the rate at which delivery fluid is pumped (or otherwise moves or is moved) out of the delivery reservoir multiplied by the effective concentration of primary material in the delivery fluid. A delivery device may include a pump for pumping delivery fluid from the delivery reservoir. Alternatively, in some cases the primary material may simply diffuse out of the delivery device. Various types of pumps may be used, without limitation. Suitable pumps may include, for example, osmotic, mechanical, displacement, centrifugal, and peristaltic pumps.

Figure 7A:
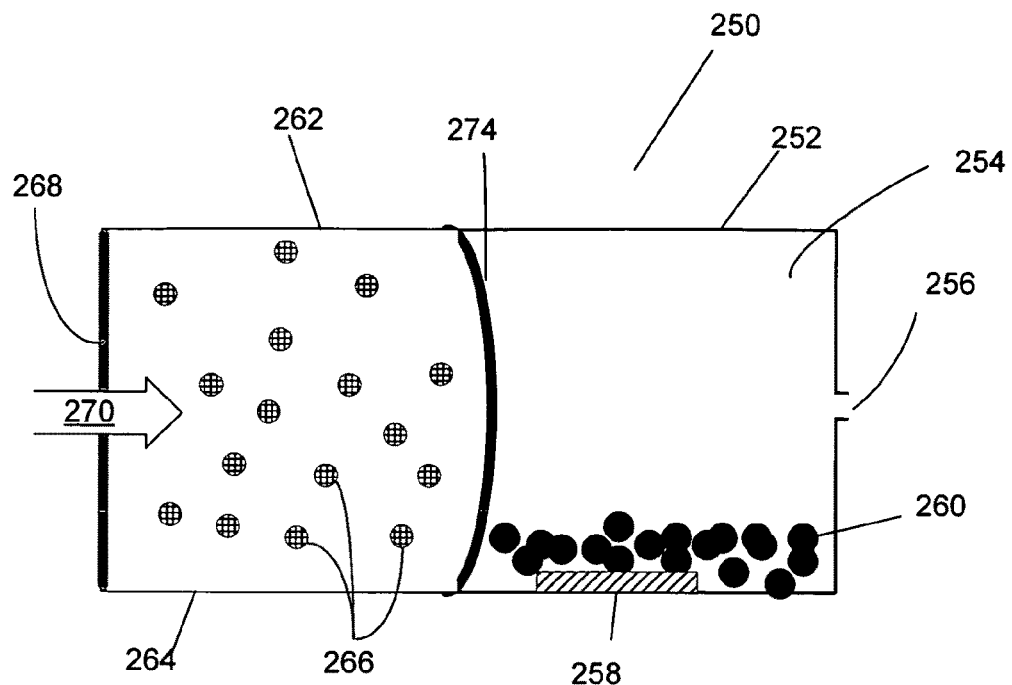
FIGS. 7A and 7B illustrate a change in concentration in delivery fluid in exemplary delivery device including an osmotic pump.
Figure 7B:
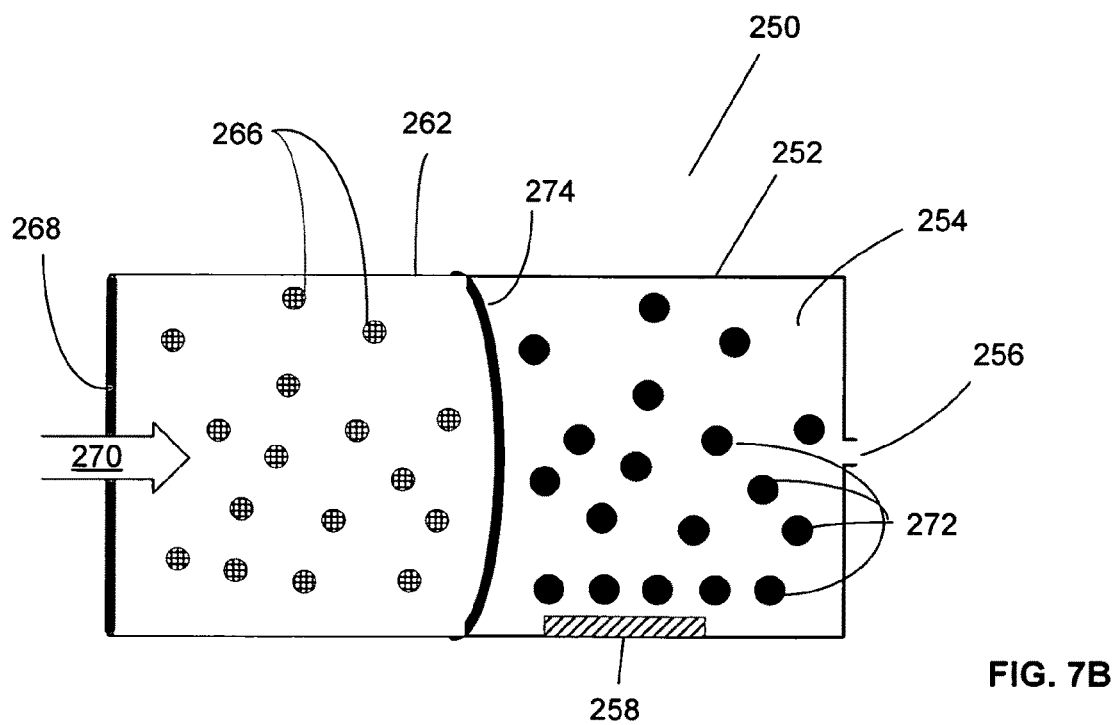

FIGS. 7A and 7B illustrate an embodiment of a delivery device that includes an osmotic pump. Delivery device 250 includes delivery reservoir 252, which contains delivery fluid 254 and may have an outlet 256. Electromagnetically (or acoustically) responsive control element 258 is located in delivery reservoir 252 to control the distribution of primary material, which in FIG. 7A is shown in the second (inactive, inaccessible or unusable) form 260. Osmotic pump 262 includes osmotic chamber 264 containing osmotic pressure generating material 266. Semi-permeable membrane 268 is permeable to osmotic fluid 270 but not to osmotic pressure generating material 266. Osmotic fluid 270 thus flows into osmotic chamber 264. This causes movable barrier 274 (which may be a rigid movable barrier or a flexible membrane) to move into delivery reservoir 252, thus pumping delivery fluid 254 out of outlet 256. As shown in FIG. 7B, activation of electromagnetically responsive control element 258 may cause primary material to be converted to first active form 272.

Various different osmotic pressure-generating materials may be used in delivery systems as described herein. For example, the osmotic pressure-generating material may include ionic and non-ionic water-attracting or water absorbing materials, non-volatile water-soluble species, salts, sugars, polysaccharides, polymers, hydrogels, osmopolymers, hydrophilic polymers, and absorbent polymers, among others. Water-attracting materials may include non-volatile, water-soluble species such as magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, various monosaccharides, oligosaccharides and polysaccharides, such as sucrose, glucose, lactose, fructose, dextran, and mixtures thereof. Water absorbing materials include osmopolymers, for example hydrophilic polymers that swell upon contact with water. Examples of water-absorbing materials include poly(hydroxyl alkyl methacrylates) MW 30,000-5,000,000, polyvinylpyrrolidone MW 10,000-360,000, anionic and cationic hydrogels, polyelectrolyte complexes, poly(vinyl alcohol) having low acetate residual, optionally cross linked with glyoxal, formaldehyde, or glutaraldehyde and having a degree of polymerization of 200 to 30,000, mixtures of e.g., methylcellulose, cross linked agar and carboxymethylcellulose; or hydroxypropyl methycellulose and sodium carboxymethylcellulose; polymers of N-vinyllactams, polyoxyethylene polyoxypropylene gels, polyoxybutylene-polyoxethylene block copolymer gels, carob gum, polyacrylic gels, polyester gels, polyuria gels, polyether gels, polyamide gels, polypeptide gels, polyamino acid gels, polycellulosic gels, carbopol acidic carboxy polymers MW 250,000-4,000,000, cyanamer polyacrylamides, cross-linked indene-maleic anhydride polymers, starch graft copolymers, acrylate polymer polysaccharides. Other water attracting and/or water absorbing materials include absorbent polymers such as poly(acrylic acid) potassium salt, poly (acrylic acid) sodium salt, poly(acrylic acid-co-acrylamide) potassium salt, poly(acrylic acid) sodium salt-graft-poly(ethylene oxide), poly(2-hydroxethyl methacrylate) and/or poly (2-hydropropyl methacrylate) and poly(isobutylene-co-maleic acid). A variety of osmotic pressure-generating materials and/or water-absorbing materials are described in US 2004/0106914 and US 2004/0015154, both of which are incorporated herein by reference in their entirety.

The osmotic pressure-generating ability of the osmotic pressure-generating material may depend on the solubility of the osmotic pressure-generating material in the osmotic fluid, and/or upon the concentration of the osmotic pressure-generating material in the osmotic fluid, and varying either concentration or solubility may modify the osmotic-pressure generating ability of the osmotic pressure-generating material. Concentration of the osmotic pressure-generating material in the osmotic fluid may be modifiable by a change in solubility of the osmotic pressure-generating material in response to an electromagnetic field (or acoustic) control signal or by a change in the osmotic fluid in response to an electromagnetic field (or acoustic) control signal.

Figure 8A:
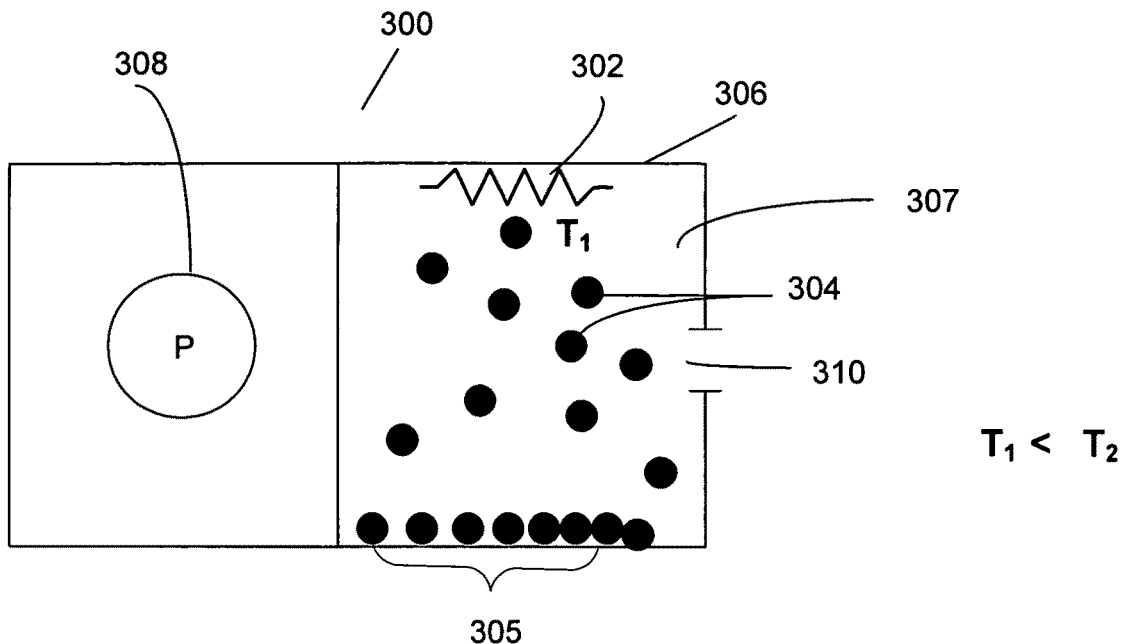
FIGS. 8A and 8B illustrate a change in concentration in a delivery fluid produced by a heating element.
Figure 8B:
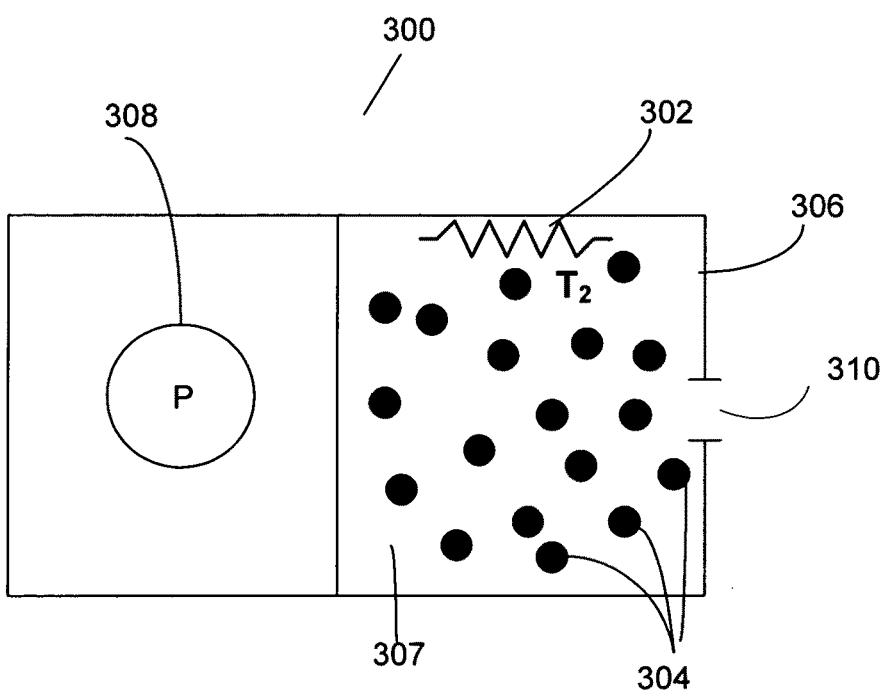

FIGS. 8A and 8B depict an embodiment of a delivery device 300 in which the electromagnetically responsive control element 302 includes an electromagnetic field responsive heating element that may respond to the control signal by producing heat. Primary material 304 is contained within delivery reservoir 306 in delivery fluid 307. Electromagnetically responsive control element 302 may be located in the wall of delivery reservoir 306. Electromagnetically responsive control element 302 has an initial temperature $T_1$. Following heating of electromagnetically responsive control element 302 in response to an electromagnetic control signal, electromagnetically responsive control element 302 has a subsequent temperature $T_2$, as shown in FIG. 8B. The change in temperature of electromagnetically responsive control element 302 may modify the concentration of primary material 304 within delivery reservoir 306. In FIG. 8A, portion 305 of primary material 304 is insoluble, while in FIG. 8B, all of primary material 304 has gone into solution, due to the change in temperature of delivery fluid 307. The electromagnetic field responsive control element 302 may include a ferrous, ferric, or ferromagnetic material, or other material with a significant electromagnetic "loss tangent" or resistivity. In the present example, the solubility of the primary material 304 in the delivery fluid 307 is depicted as increasing with increasing temperature, but in some embodiments, the solubility may decrease with increasing temperature. As in previously described embodiment, delivery device 300 may also include pump 308 and outlet 310. A similar device may be made with an acoustically responsive control element that responds to an acoustic control signal by producing heat.

Figure 9A:
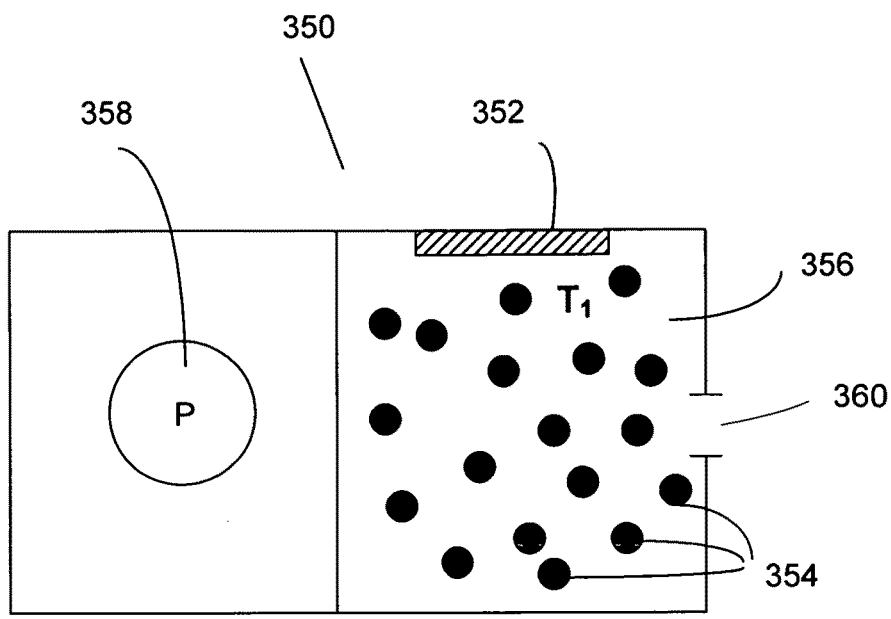
FIGS. 9A and 9B illustrate a change in concentration in a delivery fluid produced by a cooling element.
Figure 9B:
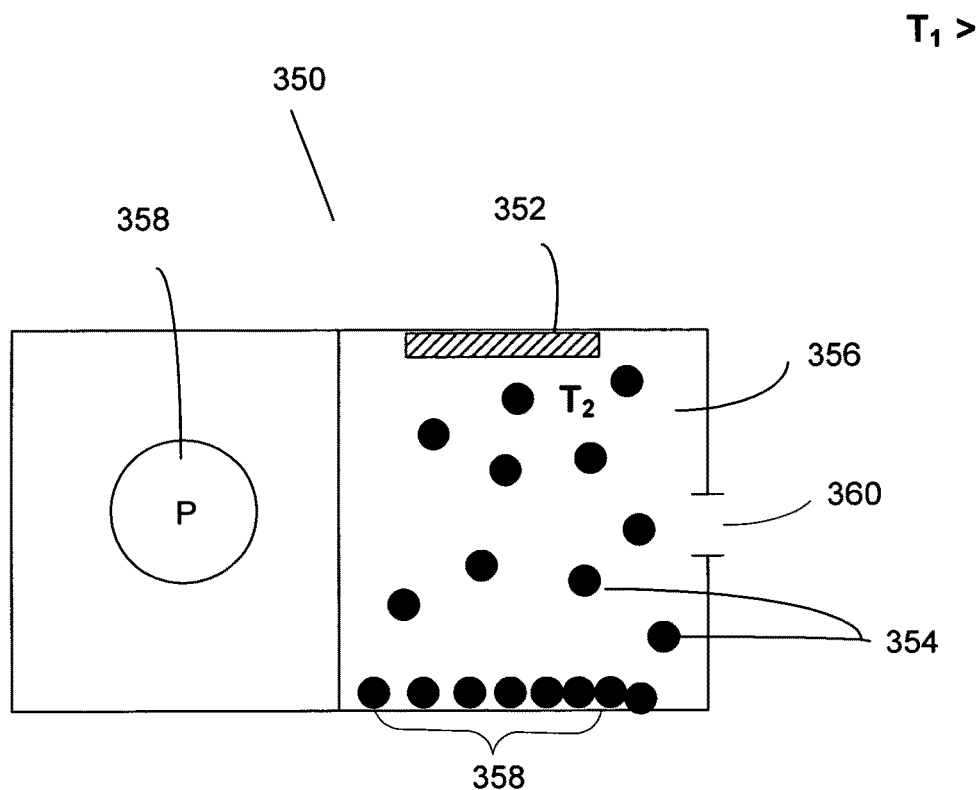

FIGS. 9A and 9B depict another embodiment of a delivery device 350, in which the at least one electromagnetically responsive control element 352 may include an electromagnetic field responsive cooling element. The electromagnetic field responsive cooling element may be capable of producing a decrease in temperature in the delivery fluid, wherein the primary material 354 has a solubility in the delivery fluid 356 that changes in response to a decrease in temperature of the delivery fluid. The electromagnetic field responsive cooling element 352 may include a thermoelectric element, for example. Methods and/or mechanisms of producing cooling may include, but are not limited to, thermoelectric (Peltier Effect) and liquid-gas-vaporization (Joule-Thomson) devices, or devices which employ "phase-changing" materials or systems involving significant enthalpies of transition. The solubility of the primary material 354 may increase with decreasing temperature, or it may decrease with decreasing temperature, as depicted in FIGS. 9A and 9B. In FIG. 9A, for example, cooling element 352 is not producing cooling, and the temperature is at a higher temperature $T_1$ and primary material 354 is substantially all in solution in delivery fluid 356. In FIG. 9B, cooling element 352 may be activated to produce cooling, so that the temperature of delivery fluid 356 decreases to temperature $T_2$. At temperature $T_2$ a portion 358 or primary material goes out of solution, resulting in a lower effective concentration of primary material in delivery fluid 356.

Figure 10A:
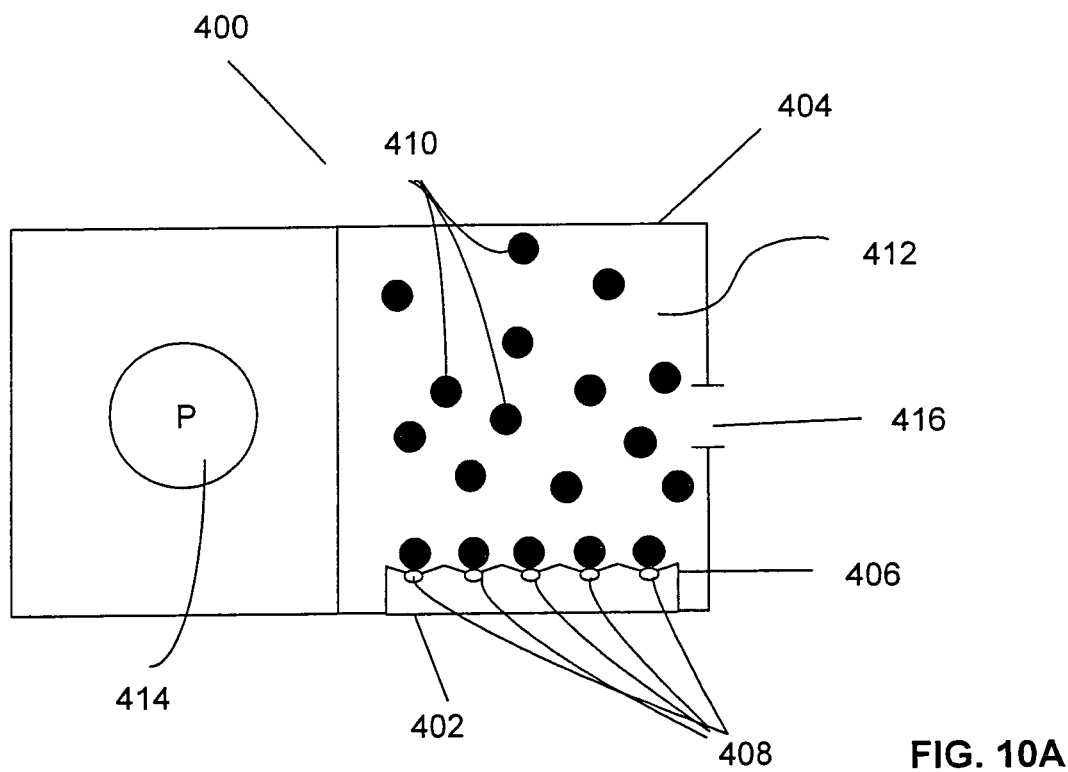
FIGS. 10A and 10B illustrate a change in concentration in a delivery fluid produced by interaction of a primary material with an interaction region.
Figure 10B:
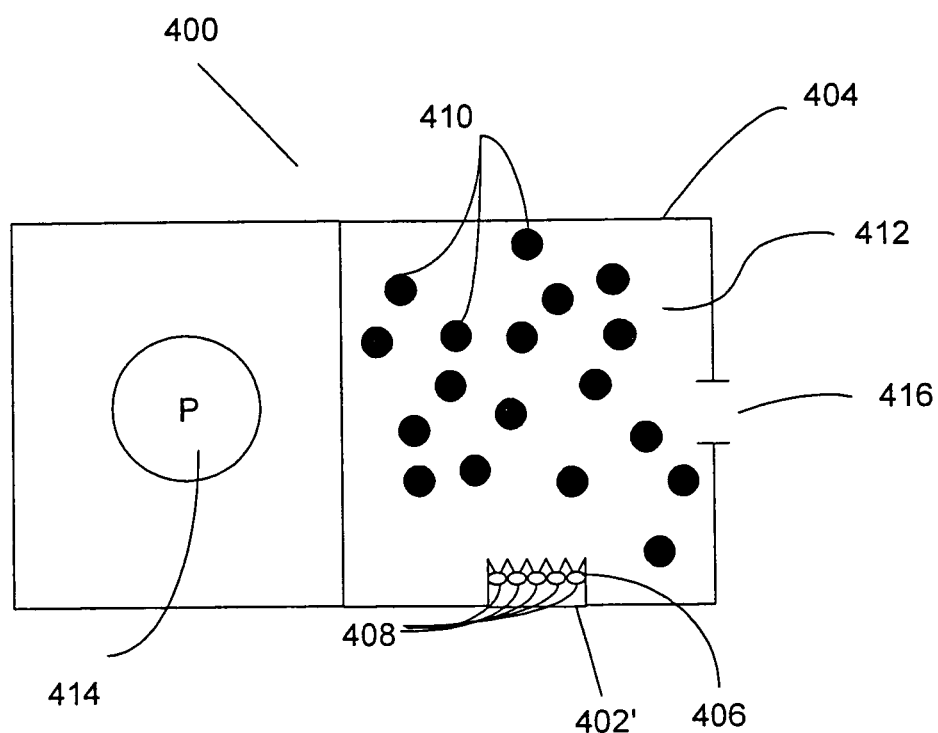
Figure 11A:
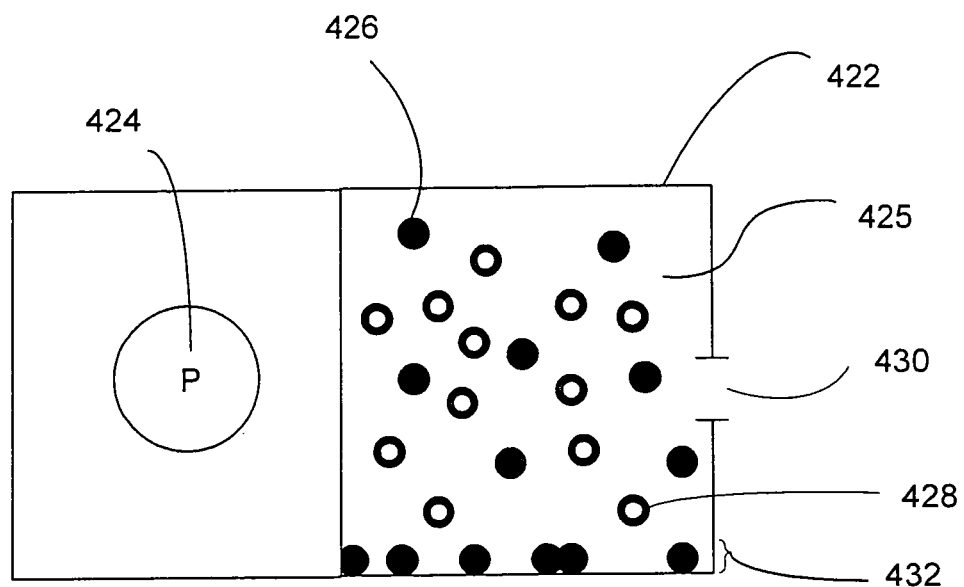
FIGS. 11A and 11B illustrate a change in concentration of primary material influenced by secondary material in a delivery fluid.
Figure 11B:
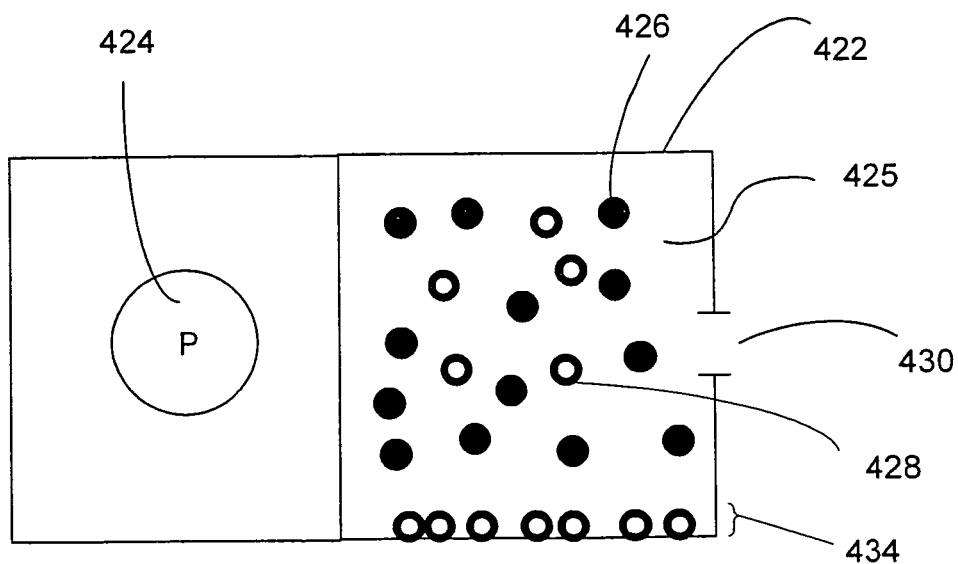

In some embodiments of the delivery device, the at least one electromagnetically (or acoustically) responsive control element may be a shape-changing structure that changes in at least one dimension in response to an electromagnetic (or acoustic) control signal. FIGS. 10A and 10B depict delivery device 400 that includes an electromagnetically responsive control element 402 that is a shape-changing structure located in the wall of delivery reservoir 404. An interaction region 406 including interaction sites 408 may be located on or adjacent to electromagnetically responsive control element 402, so that the dimension of interaction region 406 is modified with the change in dimension of electromagnetically responsive control element 402. Interaction sites 408 may bind primary material 410, thus keeping it out of solution, and maintaining a lower effective concentration in delivery reservoir 404; a change in spacing or exposure of interaction sites 408 may modify the interaction of primary material 410 with interaction sites 408, and thus modifies the effective concentration in delivery reservoir 404. For example, in FIG. 10B, the electromagnetically responsive control element 402' has contracted in at least one dimension to produce a corresponding decrease in size of interaction region 406, and reduction in spacing between interaction sites 408. In the example depicted in FIG. 10B, the reduction in interaction site spacing reduces interactions with primary material 410, causing it to go into solution in delivery fluid 412 in higher concentration.

Interaction sites may be localized to an interaction region, as depicted in FIGS. 10A and 10B, or, in alternative embodiments, the interaction sites may be distributed to various locations within the delivery reservoir. The delivery device may include a plurality of interaction sites for the primary material within the delivery reservoir, the likelihood of interaction of the primary material with the interaction sites controllable by the electromagnetic field control signal, wherein interaction of the primary material with the interaction sites causes a change in effective concentration within the delivery reservoir. The interaction sites may be capable of interacting with the primary material by one or more of binding, reacting, interacting, or forming a complex with the primary material. The interaction sites may be responsive to an electromagnetic field control signal by a change in at least one characteristic, the change in the at least one characteristic modifying the interaction between the interaction sites and the primary material. The at least one characteristic may include, but is not limited to, at least one of a solubility, a reactivity, a distribution within the delivery reservoir, a density, a temperature, a conformation, an orientation, an alignment, or chemical potential, for example.

In some embodiments, the at least one electromagnetically responsive control element may be an electromagnetic field responsive molecule in the delivery fluid, and wherein the electromagnetic field responsive molecule undergoes a change in conformation from a first conformation state to a second conformation state in response to the electromagnetic control signal, and wherein the first conformation state has a first solubility in the delivery fluid and wherein the second conformation state has a second solubility in the delivery fluid. Such an electromagnetic field responsive molecule may form at least a portion of the primary material in the delivery fluid, or alternatively, the electromagnetic field responsive molecule may form at least a portion of a secondary material that influences the solubility of the primary material in the delivery fluid, as illustrated in FIGS. 11A and 11B.

FIG. 11A depicts a delivery device 420 including delivery reservoir 422 and pump 424. Delivery reservoir 422 contains delivery fluid 425, primary material 426, and secondary material 428. Delivery fluid 424 may exit delivery reservoir 422 via outlet 430. In FIG. 11A, secondary material 428 is all in solution, and a portion 432 of primary material has been forced out of solution. In FIG. 11B, in response to a change in the electromagnetic field control signal, a portion 434 of secondary material 428 has gone out of solution, with the effect that a larger amount of primary material 426 goes into solution, thus increasing the concentration of primary material 426 in delivery fluid 242. Secondary material 428 may influence the concentration of primary material 426 by modifying the pH, polarity or other characteristic of delivery fluid 244, or by interacting or reacting with primary material 426 directly to modify its solubility in delivery fluid 424.

FIGS. 10A and 10B depict one method of using a shape changing material to vary the effective concentration of a primary material in a delivery device. Other embodiments that utilize shape-changing materials are also contemplated. A shape-changing structure may include a polymeric material, a ferropolymer, a hydrogel, a bimetallic structure, or a shape memory material. In some embodiments, the shape-changing structure may be an expanding or contracting structure, wherein the change in at least one dimension includes an expansion or contraction in at least one dimension. Expansion or contraction of the expanding or contracting structure may modify the volume of a delivery reservoir, or expose molecular structures to the delivery fluid that modify the solubility of the primary material in the delivery fluid, as will be discussed in the following example.

A change in surface area may be produced by stretching a portion of the delivery reservoir, as depicted in FIGS. 12A-12D, or a change in surface area may be produced by unfolding a portion of the delivery reservoir, as depicted in FIGS. 13A and 13B, or by some of change in conformation of at least a portion of the delivery reservoir.

FIGS. 12A-12D depict the effect of changes in one or two dimensions on an interaction region 450. Such an interaction region may be formed, for example, on an electromagnetically responsive control element that expands in response to a control signal. Interaction region 450 may include a plurality of reaction sites 452, and having initial length of $x_1$ in a first dimension and $y_1$ in a second dimension. FIG. 12B depicts interaction region 450 following a change in the first dimension, to a length $x_2$. FIG. 12C depicts interaction region 450 following a change in the second dimension, to a length $y_2$, and FIG. 12D depicts interaction region 450 following a change in both the first and second dimensions, to a size of $x_2$ by $y_2$. In each case, a change in dimension results in a change in distance between reaction sites 452. The dimension change depicted in FIGS. 12A-12D may be viewed as a 'stretching' or 'expansion' of the interaction region. Increasing the surface area of the interaction region may increase the rate of the reaction. Increasing the surface area of the interaction region (e.g., by stretching the surface) may increase the distance between reaction sites on the interaction region. An increased distance between reaction sites may lead to an increase in reaction rate (for example, in cases where smaller spacing between reaction sites leads to steric hindrance that blocks access of reactants to reaction sites).

In addition to increasing surface areas or reaction volumes, expansion of an electromagnetically (or acoustically) responsive control element may also have the effect of exposing additional portions of an interaction region or exposing additional functional group to influence a reaction condition. Increasing the surface area of the interaction region by unfolding or other forms of 'opening' of the interaction region structure of at least a portion of the reaction area may increase the number of reaction sites on the interaction region (e.g. by exposing additional reaction sites that were fully or partially hidden or obstructed when the interaction region was in a folded configuration). For example, the area of an interaction region may be increased by the unfolding of at least a portion of the reaction area to expose additional portions of the reaction area, as depicted in FIGS. 13A and 13B. In FIG. 13A, an interaction region 500, which includes or is made up of an electromagnetically responsive control element, can be expanded by unfolding to the form depicted in FIG. 13B. Interaction region 500 has a pleated structure that includes ridges 502*a*-502*e* and valleys 504*a*-504*d*. Reaction sites 506 may be located in or on ridges 502*a*-502*e* and valleys 504*a*-504*d*. In the folded form illustrated in FIG. 13A, reaction sites 506 located in valleys 504*a*-504*d* are 'hidden' in the sense that reactants may not fit into the narrow valleys to approach those reaction sites, while reaction sites on ridges 502*a*-502*e* remain exposed. When interaction region 500 is unfolded to the form shown in FIG. 13B, reaction sites 506 in valleys 504*a*-506*d* are exposed, because the open valleys permit access of reactants to the reaction sites in the valleys. Examples of materials that unfold in response to electromagnetic fields include ionic polymer-metal composites (IPMC) as described in Shahinpoor et al., "Artificial Muscle Research Institute: Paper: Ionic Polymer-Metal Composites (IPMC) As Biomimetic Sensors, Actuators and Artificial Muscles-A Review"; University of New Mexico; printed on Oct. 21, 2005; pp. 1-28; located at: http://www.unm.edu/~amri/paper.html, which is incorporated herein by reference.

Increasing the surface area of the interaction region may decrease the rate of the interaction in some circumstances and increase the rate of interaction in others. Exposure of additional portions of the interaction region may expose additional functional groups that are not reaction sites, but that may produce some local modification to a surface property of the interaction region that in turn modifies the rate or kinetics of the reaction. For example, exposed functional groups may produce at least a local change in pH, surface energy, or surface charge. See, for example, U.S. patent publication 2003/0142901 A1, which is incorporated herein by reference. A related modification of the interaction region may include an increase in porosity or decrease in density of an electromagnetically responsive control element. An increase in porosity may have a similar effect to unfolding with respect to modifying the spacing or exposure of reaction sites, functional groups, etc. See, for example U.S. Pat. Nos. 5,643,246, 5,830,207, and 6,755,621, all of which are incorporated herein by reference. FIGS. 14A and 14B depict an electromagnetically responsive control element 530 that expands in response to an electromagnetic control signal, with a corresponding increase in size of pores 532 in FIG. 14B relative to the size of pores 532 in FIG. 14A.

A change in the spacing of interaction sites may increase or decrease the rate of interaction, or modify another parameter of an interaction, in a manner that depends on the specific reaction and reactants. Heating or cooling of a reaction volume may also modify a chemical reaction by modifying the pressure or the pH or the osmolality or other reaction-pertinent chemical variables within the reaction space. In some embodiments, a delivery device may include at least one interaction region capable of interacting with the primary material by one or more of binding, reacting, interacting, or forming a complex with the primary material. The at least one interaction region may be responsive to the electromagnetic control signal by a change in at least one characteristic, the change in the at least one characteristic modifying the interaction between the at least one interaction region and the primary material. For example, the at least one characteristic may include at least one solubility, reactivity, temperature, conformation, orientation, alignment, binding affinity, chemical potential, surface energy, porosity, osmolality, pH, distribution within the delivery reservoir, or density. In some embodiments, at least a portion of the delivery reservoir containing, the at least one interaction region may be responsive to an electromagnetic control signal by a change in the surface area of the portion of the delivery reservoir, the change in surface area modifying the likelihood of interaction of the primary material with the at least one interaction region. For example, the change of surface area may be produced by stretching or expansion of the portion of the delivery reservoir, or by unfolding of the portion of the delivery reservoir.

Figures 15A, 15B:
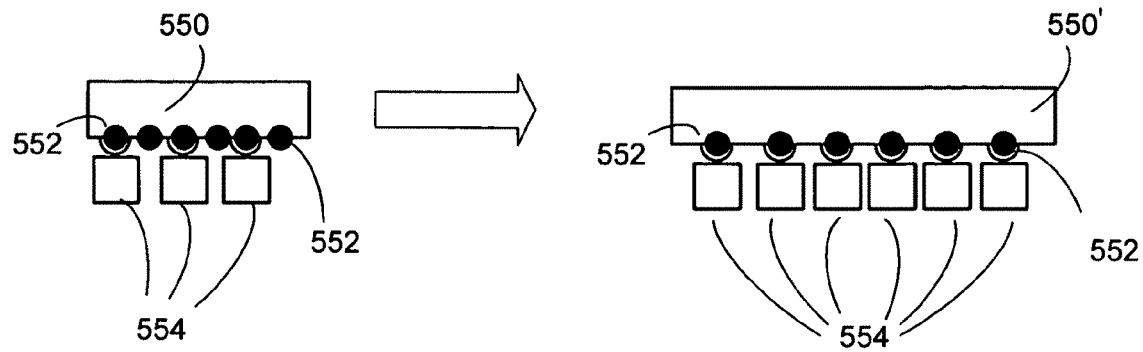
FIGS. 15A and 15B depict an example of an effect of stretching an interaction region.

The influence of modifying the surface area of an interaction region is described further in connection with FIGS. 15A and 15B and 16A and 16B. FIGS. 15A and 15B illustrate how an increase of the surface area of an interaction region by stretching or expansion may increase the rate of the interaction occurring at the interaction region. Multiple interaction sites 552 are located in interaction region 550. As shown in FIG. 15A, prior to stretch or expansion, interaction sites 552 are close together, and primary material 554, which binds to the interaction sites 552, is sufficiently large that it is not possible for primary material 554 to bind to each interaction site 552. When interaction region 550 has been stretched or expanded to expanded form 550' as depicted in FIG. 15B, so that the interaction sites 552 are further apart, it is possible for primary material 554 to bind to a larger percentage of the interaction sites, thus increasing the rate of interaction.

Figures 16A, 16B:
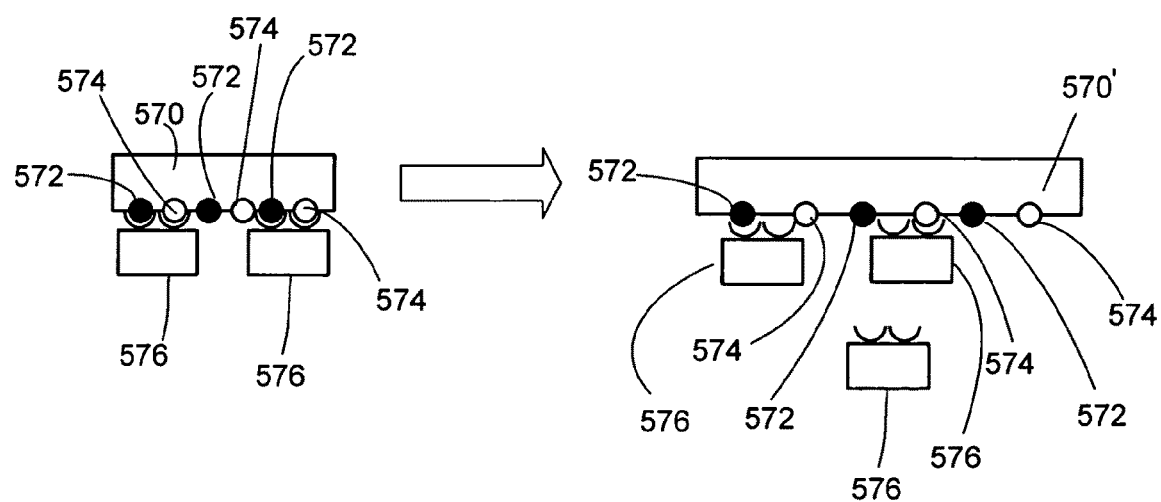
FIGS. 16A and 16B depict another example of an effect of stretching an interaction region.

In some embodiments, an increase in the surface area of the interaction region by stretching or expansion may decrease the interaction rate (for example, in cases where a particular spacing is needed to permit binding or association of primary material with several interaction sites simultaneously). FIGS. 16A and 16B illustrate how an increase in the surface area of an interaction region 570 by stretching or expansion may decrease the rate of the interaction occurring at the interaction region. Again, multiple interaction sites 572 and 574 are located in the interaction region 570, as depicted in FIG. 16A. In the present example binding of a primary material 576 to interaction region 570 requires binding of a primary material 576 to two interaction sites 572 and 574. When interaction region 570 is stretched or expanded to expanded form 570' as depicted in FIG. 16B, the spacing of the two interaction sites 572 and 574 is changed so that primary material 576 does not readily bind to interaction region in the expanded form 570', thus reducing the rate of interaction.

Many materials expand when thermal energy is applied. By combining materials as in polymer gels one can use the differing properties of individual components to affect the whole. Thermally-responsive materials include thermally responsive gels (hydrogels) such as thermosensitive N-alkyl acrylamide polymers, Poly(N-isopropylacrylamide) (PNIPAAm), biopolymers, crosslinked elastin-based networks, materials that undergo thermally triggered hydrogelation, memory foam, resin composites, thermochromic materials, proteins, memory shape alloys, plastics, and thermoplastics. Materials that contract or fold in response to heating may include thermally-responsive gels (hydrogels) that undergo thermally triggered hydrogelation (e.g. Polaxamers, uncross-linked PNIPAAm derivatives, chitosan/glycerol formulations, elastin-based polymers), thermosetting resins (e.g. phenolic, melamine, urea and polyester resins), dental composites (e.g. monomethylacrylates), and thermoplastics.

Some examples of reactions that may be sped up by change in distance between reaction sites include those involving drugs designed with spacers, such as dual function molecules, biomolecules linked to transition metal complexes as described in Paschke et al, "Biomolecules linked to transition metal complexes-new chances for chemotherapy"; Current Medicinal Chemistry; bearing dates of October 2003 and Oct. 18, 2005, printed on Oct. 24, 2005; pp. 2033-44 (pp. 1-2); Volume 10, Number 19; PubMed; located at: http://www.ncbi.nlm.nih.gov/entrez/query.fcgi?cmd=Retrieve&db=PubMed&list_uids=12871101&dopt=Abstract, and Schiff bases as described in Puccetti et al., "Carbonic anhydrase inhibitors", Bioorg. Med. Chem. Lett. 2005 Jun. 15; 15(12): 3096-101 (Abstract only), both of which are incorporated herein by reference. Other reactions include reactions responding to conformational (allosteric) changes including regulation by allosteric modulators, and reactions involving substrate or ligand cooperativity in multiple-site proteins, where binding affects the affinity of subsequent binding, e.g., binding of a first $O_2$ molecule to Heme increases the binding affinity of the next such molecule, or influence of Tau on Taxol, as described in Ross et al., "Tau induces cooperative Taxol binding to microtubules"; PNAS; Bearing dates of Aug. 31, 2004 and 2004; pp. 12910-12915; Volume 101, Number 35; The National Academy of Sciences of the USA; located at: http://gabriel.physics.ucsb.edu/~deborah/pub/RossPNASv101p12910y04.pdf, which is incorporated herein by reference. Reactions or interactions that may be slowed down by increased reaction site spacing include reactions responsive to conformational (allosteric) changes, influence or pH, or crosslinking. See for example Boniface et al., "Evidence for a Conformational Change in a Class II Major Histocompatibility Complex Molecule Occurring in the Same pH Range Where Antigen Binding Is Enhanced"; J. Exp. Med.; Bearing dates of January 1996 and Jun. 26, 2005; pp. 119-126; Volume 183; The Rockefeller University Press; located at: http://www.jem.org also incorporated herein by reference or Sridhar et al., "New bivalent PKC ligands linked by a carbon spacer: enhancement in binding affinity"; J Med. Chem.; Bearing dates of Sep. 11, 2003 and Oct. 18, 2005, printed on Oct. 24, 2005; pp. 4196-204 (pp. 1-2); Volume 46, Number 19; PubMed (Abstract); Located at: http://www.ncbi.nlm.nih.gov/entrez/query.fcgi?cmd=Retrieve&db=PubMed&list_uids=12954072&dopt=Abstract, also incorporated herein by reference.

In some embodiments, the interaction region may include interaction sites that include a secondary material capable of interacting with or influencing the solubility of the primary material. The electromagnetically responsive control element may modify the influence of the secondary material. In some embodiments the secondary material may not be localized to an interaction region, but may be distributed within the delivery reservoir, but responsive to an electromagnetic control signal. The secondary material may interact with or influence primary material in a variety of ways. As a first example, the secondary material may be a receptor or other binding location that binds or sequesters the primary material, either specifically or non-specifically, to take it out of solution. FIGS. 17A and 17B depict an interaction between primary material 600 and secondary material 602 in interaction region 604. In FIG. 17A, prior to activation of electromagnetically responsive control element 606, primary material 600 does not bind to secondary material 602 in interaction region 604. Following activation of electromagnetically responsive control element 606, secondary material 602 undergoes a change to modified form 602' as depicted in FIG. 17B, which allows primary material 600 to bind to it and go out of solution, thus reducing the effective concentration of the primary material in the delivery fluid.

In the example shown in FIGS. 18A and 18B, secondary material 630 is not itself a receptor or binding site for the primary material 632, but modifies interaction between the primary material 632 and an interaction site 634 (which may be, for example, a binding or receptor site) in interaction region 636. In FIG. 18A, the secondary material 630 is in a first configuration which blocks access of primary material 632 to interaction site 634. In FIG. 18B, under the influence of electromagnetically responsive control element 638, secondary material 630 has assumed a second configuration 630' which permits access of primary material 632 to interaction site 634. Secondary material 630 may be a material that modifies the rate or nature of the interaction between primary material 632 and interaction site 634 in response to an electromagnetic control signal by steric effects, by modifying the polarity of at least a portion of an interaction region, such as e.g., hydrophobic or hydrophilic groups; by modifying the pH of at least a portion of the interaction region, with acids or acidifiers (e.g., ammonium chloride), bases or alkalizers (sodium bicarbonate, sodium acetate) or buffering agents (e.g., mono- or di-hydrogen phosphates); or it may be a material that modifies the charge of at least a portion of the interaction region, such as including various enzyme, neuraminidase, transferase, antioxidants, and charge donors.

In the example of FIGS. 19A and 19B, secondary material 640 is a reactant that reacts with primary material 642 to produce reaction product 644. Primary material 642 approaches secondary material 640 in interaction region 646 in FIG. 19A, and reaction product 644 leaves interaction region 646 in FIG. 19B. The reaction between secondary material 640 and primary material 642 is caused, produced, facilitated, or otherwise increased or enhanced by activation of electromagnetically responsive control element 648, (e.g., to produce heating, cooling, a change in surface charge, conformation, etc.) Reaction product 646 may have a different effective concentration in the delivery fluid than primary material 642 due to different solubility, or chemical activity, for example, or because the reaction results in an increase or decrease in the number of chemically active molecules in the reaction chamber. A reaction by-product 610 may remain at interaction region 646, as depicted in FIG. 19B, or secondary material 640 may be completely consumed by the reaction.

The influence of the electromagnetically responsive control element in the examples depicted in FIGS. 17A-19B may be any of various influences, including but not limited to those described herein; e.g., modifying the temperature of the interaction region or exposing reaction sites or functional groups. As noted elsewhere herein, in related embodiments, an acoustically responsive control element may be used in place of an electromagnetically responsive control element. The interaction that takes place at the interaction region may change the effective concentration of primary material within the delivery reservoir by producing reaction products in different quantities or with different solubility or chemical activity than the reactants. In some embodiments, the interaction region may include a catalyst that facilitates a chemical reaction but is not modified by the chemical reaction, for example, metals such as platinum, acid-base catalysts, catalytic nucleic acids such as ribozymes or DNAzymes. The interaction region may include an enzyme, such as an oxidoreductase (e.g. glucose oxidase), transferase (including glycosyltransferase, kinase/phosphorylase), hydrolase, lyase, isomerase, ligase, and enzymatic complexes and/or cofactors. Various examples of catalysts are provided in Kozhevnikov, "Catalysts for Fine Chemical Synthesis, Volume 2, Catalysis by Polyoxometalates"; Chipsbooks.com; Bearing dates of 2002 and 1998-2006, printed on Oct. 21, 2005; pp 1-3 (201 pages); Volume 2; Culinary and Hospitality Industry Publications Services; located at: http://www.chipsbooks.com/catcem2.htm, which is incorporated herein by reference.

Modifying a reaction condition at the interaction region may also be accomplished by heating or cooling at least a portion of the interaction region, or by modifying the osmolality or pH, surface charge, or surface energy of at least a portion of the interaction region. Similarly, modifying a reaction condition at the interaction region may include modifying a parameter of a reaction space within the delivery device, the reaction space containing the interaction region, e.g. by modifying the volume of the reaction space, heating or cooling at least a portion of the reaction space, or modifying the osmolality, pH, pressure, temperature, chemical composition, or chemical activity of at least a portion of the reaction space.

Figure 20A:
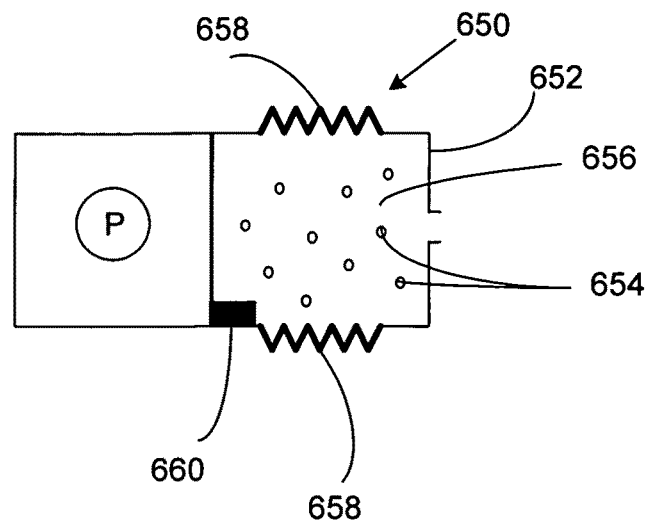
FIGS. 20A and 20B illustrate expansion of a delivery reservoir of a delivery device.
Figure 20B:
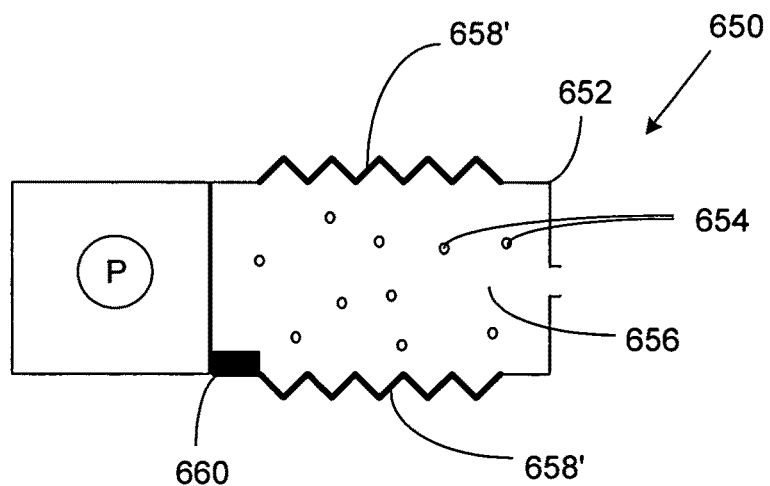

In some embodiments, expansion or other conformation change of an electromagnetically responsive control element may produce other modifications to a condition in the delivery reservoir. For example, a volume of a delivery reservoir containing the interaction region may be increased by expansion of an electromagnetically responsive control element, as depicted in FIGS. 20A and 20B. Delivery device 650 includes delivery reservoir 652 containing primary material 654 and delivery fluid 656 and having a first volume as shown in FIG. 20A. An electromagnetically responsive control element 658 that changes dimension in response to an electromagnetic control signal forms an expandable portion of the wall of delivery reservoir 652. Upon expansion of electromagnetically responsive control element to expanded form 658' shown in FIG. 20B, the volume of delivery reservoir 652 is increased, and the concentration of primary material 654 within delivery reservoir 652 is thus decreased. In this and other embodiments, the delivery device may include at least one sensor 660 for detecting at least one parameter from the delivery reservoir. For example, the sensor may detect a quantity or concentration of primary material in the delivery reservoir. In other embodiments, the delivery device may include at least one sensor for detecting a concentration or activity of a chemical within at least a portion of an environment surrounding the delivery device. Examples of sensors are described in, U.S. Pat. No. 6,935,165, and U.S. Patent Publication 2004/0007051, both of which are incorporated herein by reference.

Figure 21:
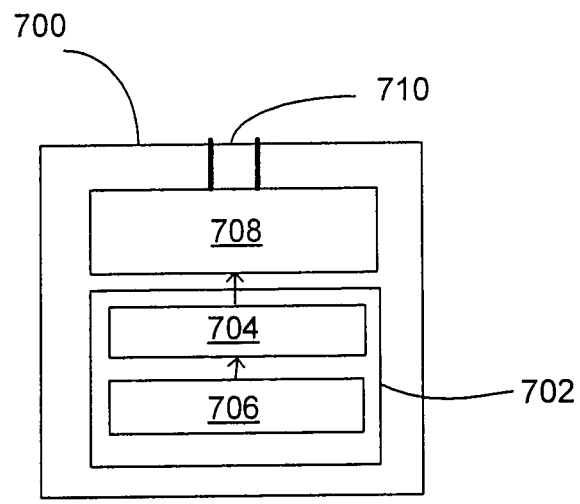
FIG. 21 is a schematic diagram of an embodiment of a delivery device.

FIG. 21 depicts in schematic form an embodiment of a delivery device 700 including an electromagnetically responsive control element 702 that includes an active portion 704 and a power receiving structure 706. Delivery device also includes delivery reservoir 708 and outlet 710. Power receiving structure 706 may be any structure that has a size, shape, and material that is suitable for receiving and transducing electromagnetic energy of a particular frequency or frequency band. The power receiving structure may include an antenna. The power receiving structure may include a resonant structure. The resonant structure may be a resonant circuit, a molecular bond, or a mechanically resonant structure. In some embodiments, power receiving structure 706 may be highly frequency-selective, while in other embodiments it may react usefully over a wide frequency band, or over multiple frequency bands. Power receiving structure 706 may be formed of various metallic or electrically or magnetically active materials. Active portion 704 may include various materials that respond mechanically, thermally or chemically to electromagnetic energy received and transduced by power receiving structure 706 to influence the effective concentration of primary material in delivery reservoir.

Figure 22:
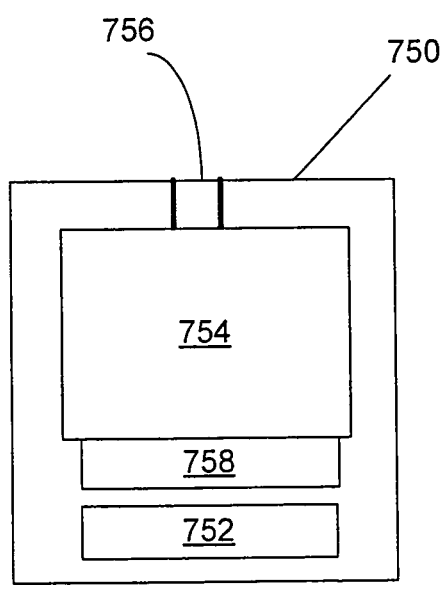
FIG. 22 is a schematic diagram of another embodiment of a delivery device.

FIG. 22 depicts an embodiment of a delivery device 750 including an RFID 752. Delivery device 750 includes delivery reservoir 754, outlet 756 and electromagnetically responsive control element 758. RFID 752 may store a unique identification code that allows delivery device 750 to be identified by a remote controller (not shown) that includes RFID detection circuitry. This provides for selective control of particular delivery devices, for example.

Delivery devices as described herein may be configured for use in a variety of environments. A delivery device of the type disclosed herein may include a body structure (e.g., body structure 38 in FIGS. 2 and 3) adapted for positioning in an environment selected from a body of an organism, as depicted in FIG. 1, or a body of water, or a contained fluid volume. The delivery reservoir may be located within the body structure. The body structure adapted for positioning in a contained fluid volume selected from an industrial fluid volume, an agricultural fluid volume, a swimming pool, an aquarium, a drinking water supply, a portable water supply, and an HVAC system cooling water supply.

Various embodiments may be used in connection with selected biomedical applications (e.g., with delivery devices adapted for placement in the body of a human or other animal). It is also contemplated that delivery systems as described herein may be used in a variety of environments, not limited to the bodies of humans or other animals. Delivery devices may be placed in other types of living organisms (e.g., plants). The environments for use of embodiments described herein are merely exemplary, and the delivery systems as disclosed herein are not limited to use in the applications presented in the examples.

Figure 23:
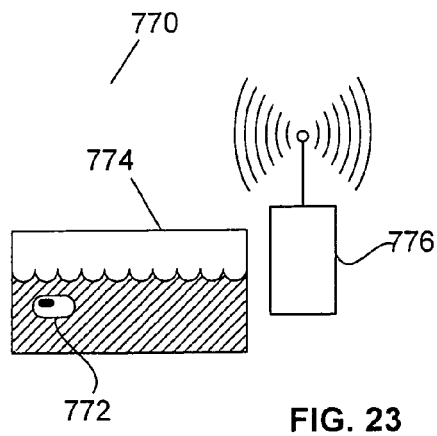
FIG. 23 depicts an embodiment of a system including a remotely controlled delivery device.

FIG. 23 illustrates an exemplary embodiment of a delivery system 770 in which a delivery device 772 is located in a small enclosed fluid volume 774 (e.g., an aquarium). A remote controller 776 is located outside enclosed fluid volume 774.

Figure 24:
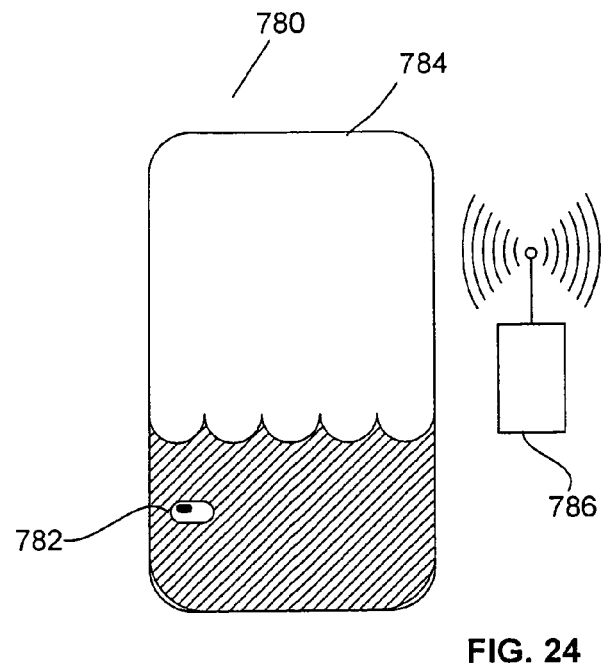
FIG. 24 depicts another embodiment of a system including a remotely controlled delivery device.

FIG. 24 illustrates a further exemplary embodiment of a delivery system 780 in which a delivery device 782 is located in a larger enclosed fluid volume 784 (which may be, for example, a water storage tank, an HVAC system cooling water tank, a tank containing an industrial fluid or an agricultural fluid). A remote controller 786 is located outside enclosed fluid volume 784.

Figure 25:
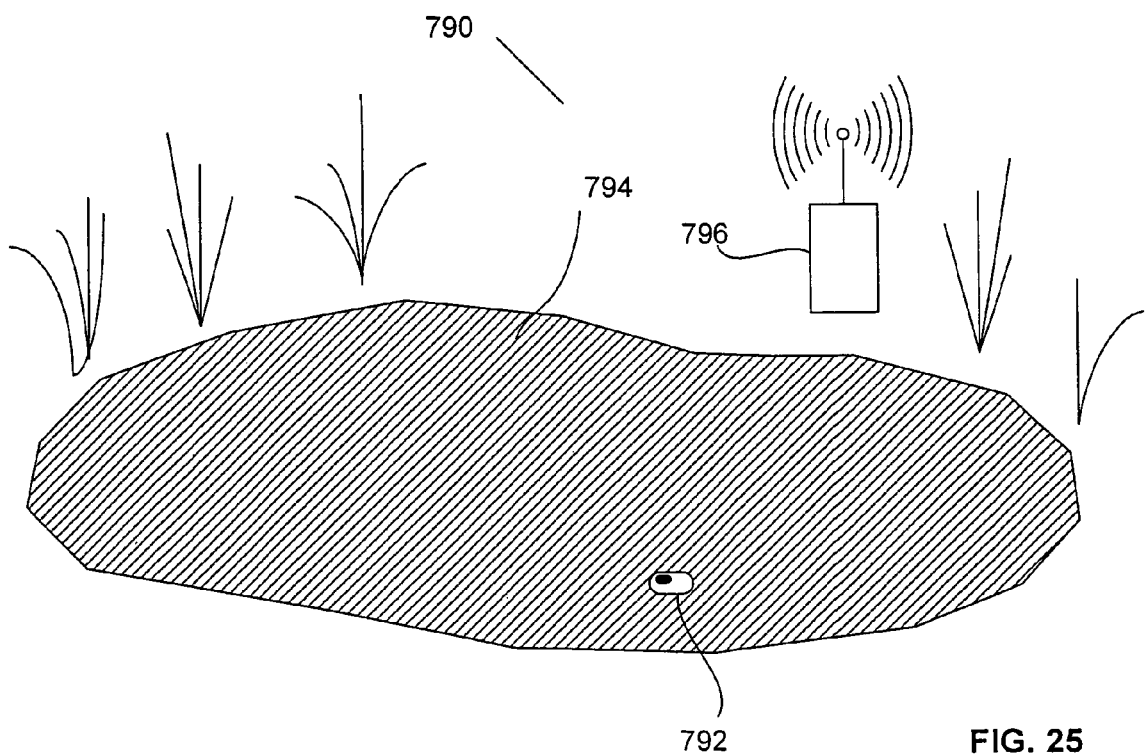
FIG. 25 depicts another embodiment of a system including a remotely controlled delivery device.

FIG. 25 illustrates a further exemplary embodiment of a delivery system 790 in which a delivery device 792 is located in a body of water 794 (a lake or pond is depicted here, but such delivery systems may also be designed for use in rivers, streams, or oceans). A remote controller 796 is shown located outside of body of water 794, though in some embodiments it may be advantageous to place remote controller 796 at a location within body of water 794.

The body structure of the delivery device may be adapted for a specific environment. The size, shape, and materials of the body structure influence suitability for a particular environment. For example, a device intended for use in a body of a human or other organism would typically have suitable biocompatibility characteristics. For use in any environment, the body structure (and device as a whole) may be designed to withstand environmental conditions such as temperature, chemical exposure, and mechanical stresses. Moreover, the body structure may include features that allow it to be placed or positioned in a desired location in the environment, or targeted to a desired location in the environment. Such features may include size and shape features, tethers or gripping structures to prevent movement of the body structure in the environment (in the case that the device is placed in the desired location) or targeting features (surface chemistry, shape, etc.) that may direct the device toward or cause it to be localized in a desired location. The body structure may include a tissue-specific marker or targeting molecule. For example, the tissue specific marker or targeting molecule may be a tissue specific endothelial protein. Small devices (e.g. as may be used for placement in the body of an organism) may be constructed using methods known to those in skill of the art of microfabrication. In applications where size is not a constraint, a wide variety of fabrication methods may be employed. The body structure of the delivery device may be formed from various materials or combinations of materials, including but not limited to plastics and other polymers, ceramics, metals, and glasses, and by a variety of manufacturing techniques.

In some embodiments, the delivery device may be a MEMS device or other microfabricated device. The delivery device may be constructed from at least one polymer, ceramic, glass, or semiconductor material. In some embodiments, the delivery device may be a battery-free device, powered by power beaming, inductive coupling, or an environmental power source. In still other embodiments, the device may include a battery or other on-board power source. In some embodiments, the delivery device may include an electromagnetic control signal generator, which may be located substantially in, on or adjacent to the delivery reservoir. In other embodiments, the electromagnetic control signal generator may be located at a location remote from the delivery reservoir.

As discussed herein, a remote controller for a delivery device may include an electromagnetic signal generator capable of producing an electromagnetic signal sufficient to activate an electromagnetically responsive control element of a delivery device located in an environment to change a concentration of a primary material within a delivery reservoir of the delivery device; and an electromagnetic signal transmitter capable of wirelessly transmitting the electromagnetic signal to the electromagnetically responsive control element. Various types and frequencies of electromagnetic control signals may be used in delivery systems as described herein. For example, in some embodiments, the delivery system may include a remote controller configured to generate a static or quasi-static electrical field control signal or static or quasi-static magnetic field control sufficient to activate the electromagnetically responsive control element to control the effective concentration of primary material in a desired manner. In other embodiments, the remote controller may be configured to generate a radio-frequency, microwave, infrared, millimeter wave, optical, or ultraviolet electromagnetic field control signal sufficient to activate the electromagnetically responsive control element to control the effective concentration of primary material in a desired manner.

Figure 26:
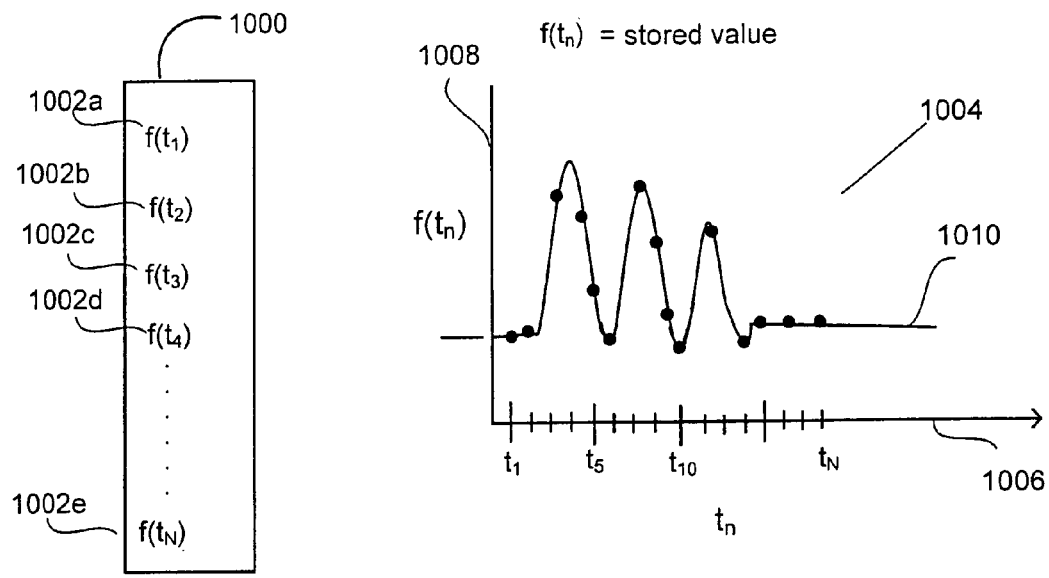
FIG. 26 illustrates a control signal generated from stored pattern data.

The electromagnetic control signal may be produced based at least in part upon a predetermined activation pattern. As shown in FIG. 26, a predetermined activation pattern may include a set of stored data $1002a$, $1002b$, $1002c$, $1002d$, ... $1002e$, having values $f(t1)$, $f(t2)$, $f(t3)$, $f(t4)$, ... $f(t_N)$, stored in a memory location 1000. The activation pattern upon which the electromagnetic signal is based is depicted in plot 1004 in FIG. 26. In plot 1004, time $t_n$ is indicated on axis 1006 and signal amplitude $f(t_n)$, which is a function of $t_n$, is indicated on axis 1008. The value of the electromagnetic signal over time is represented by trace 1010. The predetermined activation pattern represented by data $1002a$, $1002b$, $1002c$, $1002d$, ... $1002e$ may be based upon calculation, measurements, or any other method that may be used for producing an activation pattern suitable for activating an electromagnetically responsive control element. Memory 1000 may be a memory location in a remote controller. As an example, a simple remote controller may include a stored activation pattern in memory and include electrical circuitry configured to generate an electromagnetic control signal according to the pattern for a preset duration or at preset intervals, without further input of either feedback information or user data. In a more complex embodiment, a predetermined activation pattern may be generated in response to certain feedback or user input conditions.

Figure 27:
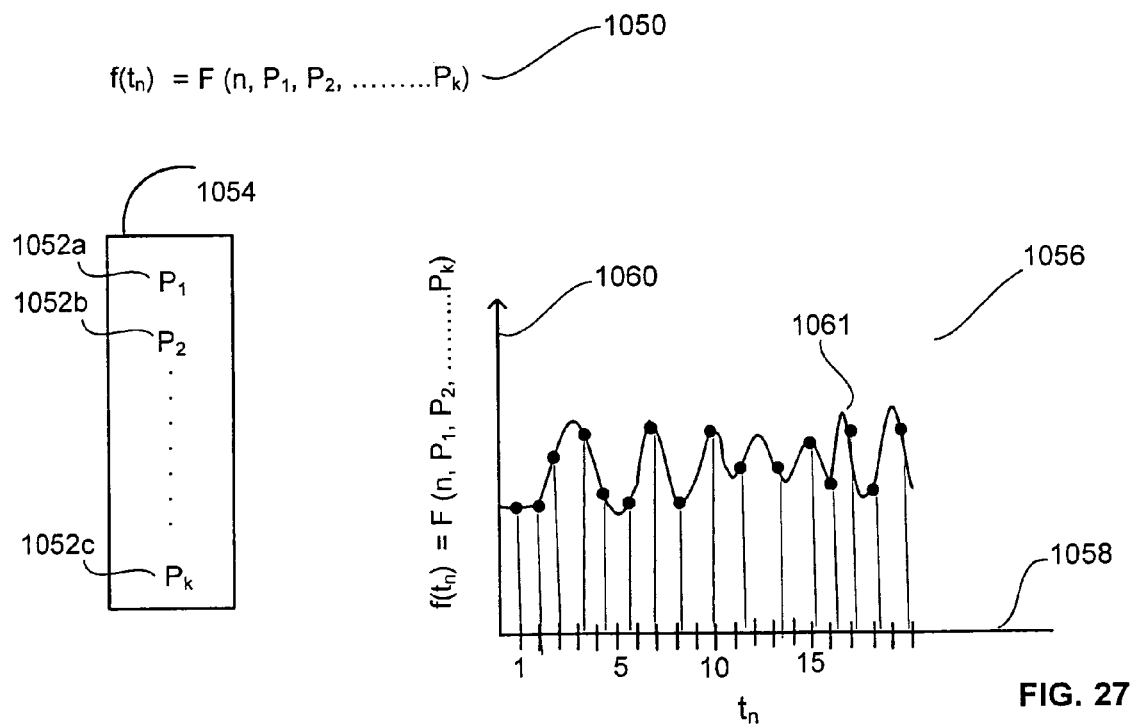
FIG. 27 illustrates a control signal calculated from a model based on stored parameters.

In some embodiments, an electromagnetic signal may be produced based upon a model-based calculation. As shown in FIG. 27, an activation pattern $f(t_n)$ may be a function not only of time $(t_n)$ but also of model parameters $P_1$, $P_2$, ... $P_k$, as indicated by equation 1050. Data $1052a$, $1052b$, ... $1052c$ having values $P_1$, $P_2$, ... $P_k$ may be stored in memory 1054. An electromagnetic control signal may be computed from the stored model parameters and time information. For example, as indicated in plot 1056, time is indicated on axis 1058 and the strength or amplitude of the electromagnetic control signal is indicated on axis 1060, so that trace 1061 represents $f(t_n)$. Memory 1054 may be a memory location in a remote controller. The remote controller may generate an electromagnetic control signal based upon the stored function and corresponding parameters. In some embodiments, the electromagnetic control signal may also be a function of one or more feedback signals (from the delivery device or the environment, for example) or of some user input of data or instructions. An acoustic control signal may be produced from a predetermined pattern or calculated from a model in an analogous fashion.

Figure 28:
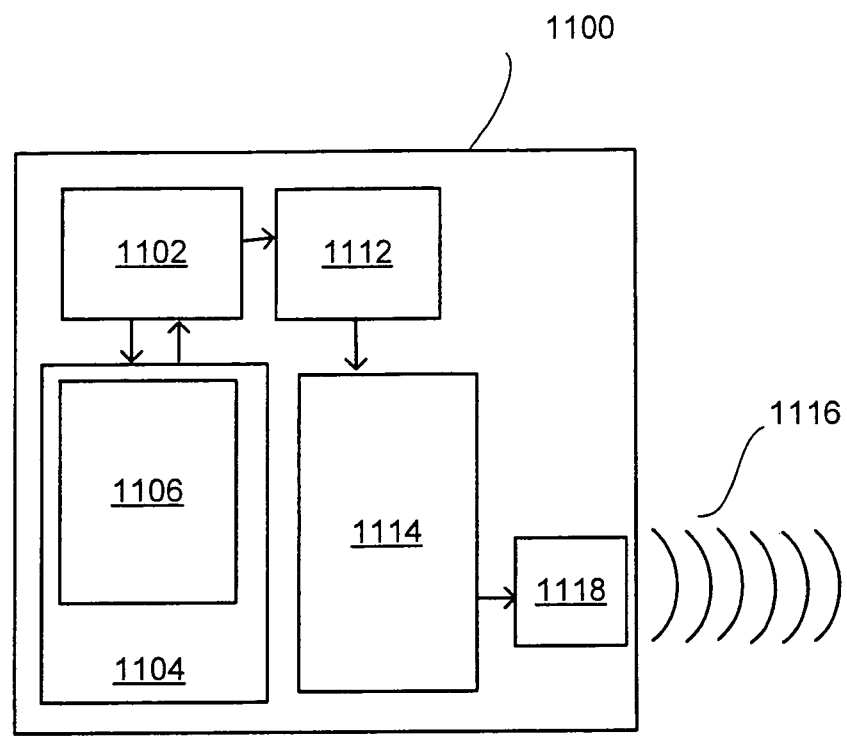
FIG. 28 is a schematic diagram of a remote controller.

FIG. 28 depicts a remote controller 1100 having a memory 1104 capable of storing pre-determined data values or parameters used in model-based calculation, as described in connection with FIGS. 29 and 30. Remote controller 1100 may also include electrical circuitry 1102, signal generator 1112, and signal transmitter 1114 for transmitting electromagnetic control signal 1116. Memory 1104 may include memory location 1106 for containing a stored activation pattern or model parameters; portions of memory 1104 may also be used for storing operating system, program code, etc. for use by processor 1102. The controller 1100 may also include a beam director 1118, such as an antenna, optical element, mirror, transducer, or other structure that may impact control of electromagnetic signaling. The electrical circuitry may include any or all of analog circuitry, digital circuitry, one or more microprocessors, computing devices, memory devices, and so forth. Remote controller may include at least one of hardware, firmware, or software configured to control generation of the electromagnetic control field signal. Software may include, for example, instructions for controlling the generation of the electromagnetic control signal and instructions for controlling the transmission of the electromagnetic control signal to the electromagnetically responsive control element.

Remote controller 1100 may be configured to produce an electromagnetic control signal having various characteristics, depending upon the intended application of the system. Design specifics of electrical circuitry, signal generator, and signal transmitter will depend upon the type of electromagnetic control signal. The design of circuitry and related structures for generation and transmission of electromagnetic signals can be implemented using tools and techniques known to those of skill in the electronic arts. See, for example, Electrodynamics of Continuous Media, 2nd Edition, by L. D. Landau, E. M. Lifshitz and L. P. Pitaevskii, Elsevier Butterworth-Heinemann, Oxford, especially but not exclusively pp. 1-13—and 199-222, which is incorporated herein by reference, for discussion of theory underlying the generation and propagation of electrical, magnetic, and electromagnetic signals.

Figure 66:
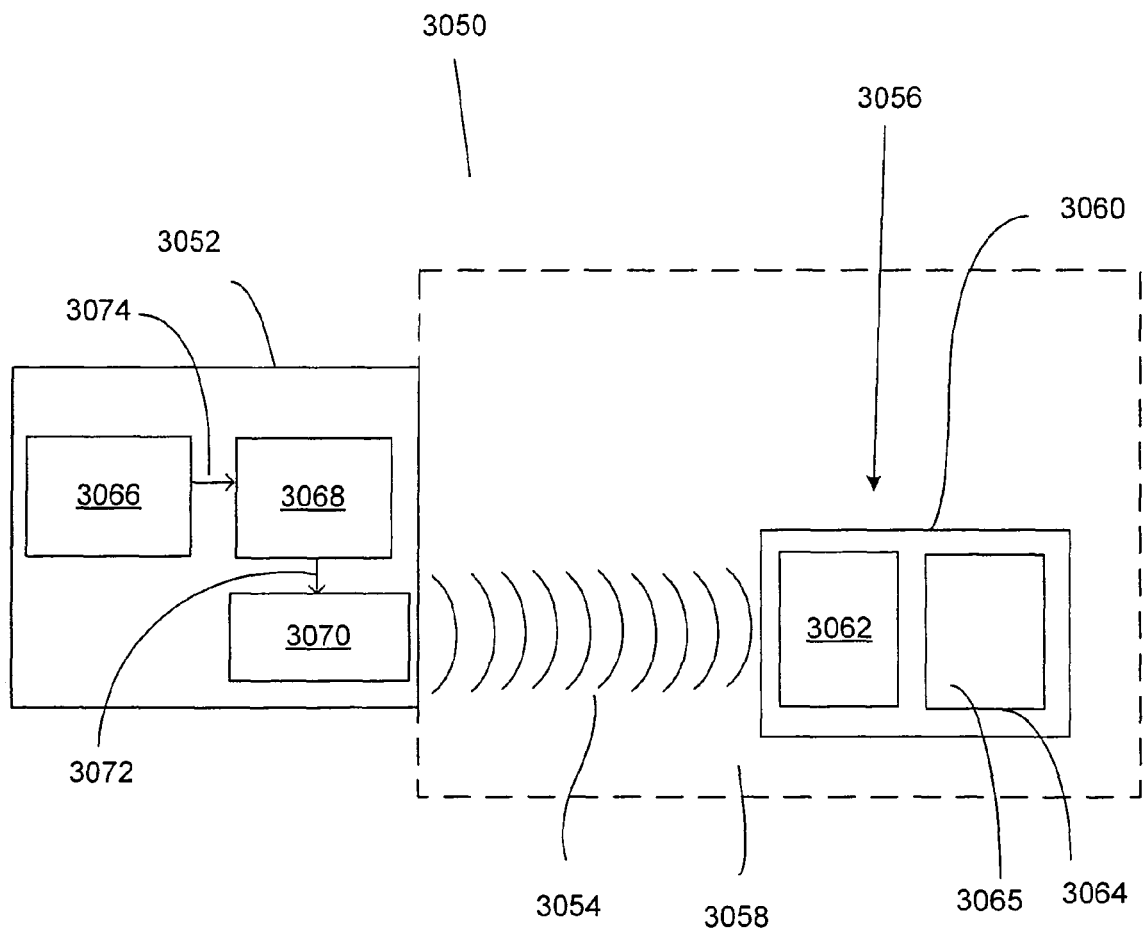
FIG. 66 is a schematic diagram of another embodiment of a delivery system.

FIG. 66 depicts a system 3050 including remote controller 3052 that transmits an acoustic control signal 3054 to delivery device 3056. Delivery device 3056 is positioned in environment 3058 and includes body structure 3060, remotely activatable control element 3062, and delivery reservoir 3064 containing delivery fluid 3065. The concentration of a primary material in delivery fluid 3065 may be controlled by remotely activatable control element 3062 in response to acoustic control signal 3054 from remote controller 3052. Remote controller 3052 includes electrical circuitry 3066, electrical driving signal generator 3068, and acoustic signal generator 3070. Electrical driving signal generator 3068 produces electrical driving signal 3072, which causes acoustic signal generator 3070 to produce acoustic control signal 3054. Electrical circuitry 3066 may include various types of electrical circuitry and may communicate with electrical driving signal generator 3068 via data line 3074. The manufacture of acoustic signal generators or transducers of various types is well known to those of skill in the art, and the underlying theory as well as the design of devices for producing acoustic signals having various signal properties is well established. www.electrotherapy.org/electro/downloads/therapeutric%20ultrasound.pdf, and "Transducer design for a portable ultrasound enhanced transdermal drug-delivery system", IEEE Trans. On Ultrasonics, Ferroelectrics and Frequency Control, Vo. 49, No. 10, October 2002, which are incorporated herein by reference, are just a few of the many references describing the theory and construction of ultrasound transducers. Acoustic signal generator 3070 may include, for example, one or more piezoelectric crystals that will vibrate in response to an applied electrical field. The acoustic signal generator may include a phased array of piezoelectric crystals in order to generate a focused acoustic signal, as is known by those of skill in the art (see, for example, "A 63 element 1.75 dimensional ultrasound phased array for the treatment of benign prostatic hyperplasia," Saleh et al., BioMed. Engr. OnLine 2005, 4:49, 17 Jun. 2005, http://www.biomedical-engineering-online.com/content/4/1/39, which is incorporated herein by reference). Phase conjugation may be used in order to compensate for inhomogeneities in the medium through which the acoustic signal is to be transmitted.

Remote controller 1100 may be configured to produce an electromagnetic control signal having various characteristics, depending upon the intended application of the system. In some embodiments, a specific remote controller may be configured to produce only a specific type of signal (e.g., of a specific frequency or frequency band) while in other embodiments, a specific remote controller may be adjustable to produce a signal having variable frequency content. Signals may include components which contribute a DC bias or offset in some cases, as well as AC frequency components. Generation of radio frequency electromagnetic signals is described, for example, in The ARRL Handbook for Radio Communications 2006, R. Dean Straw, Editor, published by ARRL, Newington, Conn., which is incorporated herein by reference. Electromagnetic signal generator 1112 may be capable of producing an electromagnetic control signal sufficient to activate an electromagnetically responsive control element of a delivery device located in an environment to change an effective concentration of a primary material in a delivery fluid within a fluid-containing structure of the delivery device; and an electromagnetic signal transmitter capable of wirelessly transmitting the electromagnetic control signal to the electromagnetically responsive control element of a delivery device in an environment. Signal transmitter 1114 may include a sending device which may be, for example, an antenna or waveguide suitable for use with an electromagnetic signal. Static and quasistatic electrical fields may be produced, for example, by charged metallic surfaces, while static and quasistatic magnetic fields may be produced, for example, by passing current through one or more wires or coils, or through the use of one or more permanent magnets, as known to those of skill in the art. As used herein, the terms transmit, transmitter, and transmission are not limited to only transmitting in the sense of radiowave transmission and reception of electromagnetic signals, but are also applied to wireless coupling and/or conveyance of magnetic signals from one or more initial locations to one or more remote locations.

The remote controller may be modified as appropriate for its intended use. For example, it may be configured to be wearable on the body of a human (or other organism) in which a delivery device has been deployed, for example on a belt, bracelet or pendant, or taped or otherwise adhered to the body of the human. Alternatively, it may be configured to be placed in the surroundings of the organism, e.g., as a table-top device for use in a home or clinical setting.

In various embodiments, the delivery device may include a remote controller configured to generate a static or quasi-static electrical field control signal, a static or quasi-static magnetic field control signal, a radio-frequency electromagnetic control signal, a microwave electromagnetic control signal, an infrared electromagnetic control signal, a millimeter wave electromagnetic control signal, an optical electromagnetic control signal, or an ultraviolet electromagnetic control signal sufficient to activate the electromagnetically responsive control element to control the effective concentration of the primary material in the delivery fluid.

Various types of electromagnetic field control signals may be used to activate the electromagnetically responsive control element. The electromagnetically responsive control element may be responsive to a static or quasi-static electrical field or a static or quasi-static magnetic field. It may be responsive to various types of non-ionizing electromagnetic radiation, or in some cases, ionizing electromagnetic radiation. Electromagnetic field control signals that may be used in various embodiments include radio-frequency electromagnetic radiation, microwave electromagnetic radiation, infrared electromagnetic radiation, millimeter wave electromagnetic radiation, optical electromagnetic radiation, or ultraviolet electromagnetic radiation.

The electromagnetic (or alternatively, acoustic) signal generator may include electrical circuitry and/or a microprocessor. In some embodiments, the electromagnetic signal may be produced at least in part according to a pre-determined activation pattern. The remote controller may include a memory capable of storing the pre-determined activation pattern. In some embodiments, the electromagnetic (or acoustic) signal may be produced based on a model-based calculation; the remote controller may include a memory capable of storing model parameters used in the model-based calculation.

In some embodiments, the remote controller may produce an electromagnetic signal having one or both of a defined magnetic field strength or defined electric field strength. In general, the term field strength, as applied to either magnetic or electric fields, may refer to field amplitude, squared-amplitude, or time-averaged squared-amplitude. The electromagnetic signal may have signal characteristics sufficient to produce a change in dimension of the electromagnetically responsive control element, a change in temperature of the electromagnetically responsive control element, a change in conformation of the electromagnetically responsive control element, or a change in orientation or position of the electromagnetically responsive control element. In some embodiments, the electromagnetic signal generator may include an electromagnet or electrically-polarizable element, or at least one permanent magnet or electret. The electromagnetic signal may be produced at least in part according to a pre-programmed pattern. The electromagnetic signal may have signal characteristics sufficient to produce a change in dimension in the electromagnetically responsive control element, the change in dimension causing a change in the concentration of the primary material within the delivery reservoir of the delivery device. It may have signal characteristics sufficient to produce a change in temperature of the electromagnetically responsive control element, the change in temperature causing a change in the concentration of the primary material within the delivery reservoir of the delivery device. In some embodiments, it may have signal characteristics sufficient to produce a change in one or more of shape, volume, surface area or configuration of the electromagnetically responsive control element, the change in dimension in one or more of shape, volume, surface area or configuration of the electromagnetically responsive control element causing a change in the concentration of the primary material within the delivery reservoir of the delivery device. The electromagnetic signal may have signal characteristics sufficient to produce a change in shape in an electromagnetically responsive control element including a shape memory material, a bimetallic structure, or a polymeric material. The electromagnetic signal may have a defined magnetic field strength or spatial orientation, or a defined electric field strength or spatial orientation.

In some embodiments, the remote controller may be configured to generate and transmit an electromagnetic control signal having at least one of frequency and orientation that are selectively receivable by the at least one magnetically responsive control element. In some embodiments, the remote controller may include at least one of hardware, software, or firmware configured to perform encryption of electromagnetic control signal to produce an encrypted electromagnetic control signal.

Figure 29:
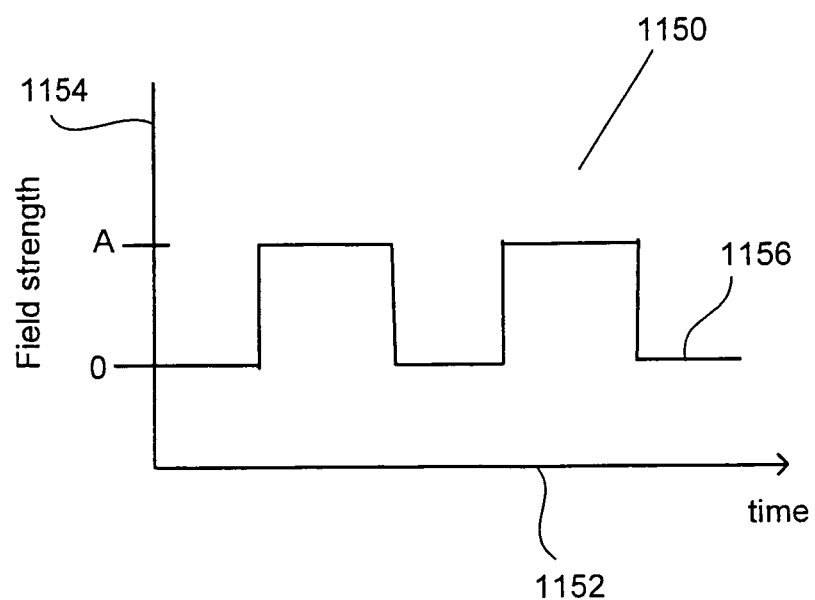
FIG. 29 depicts an exemplary control signal.

FIG. 29 depicts an example of an electromagnetic waveform of a type that may be used to activate and electromagnetically responsive control element. In plot 1150, time is plotted on axis 1152, and electromagnetic field strength is plotted on axis 1154. Trace 1156 has the form of a square wave, switching between zero amplitude and a non-zero amplitude, A.

Figure 30:
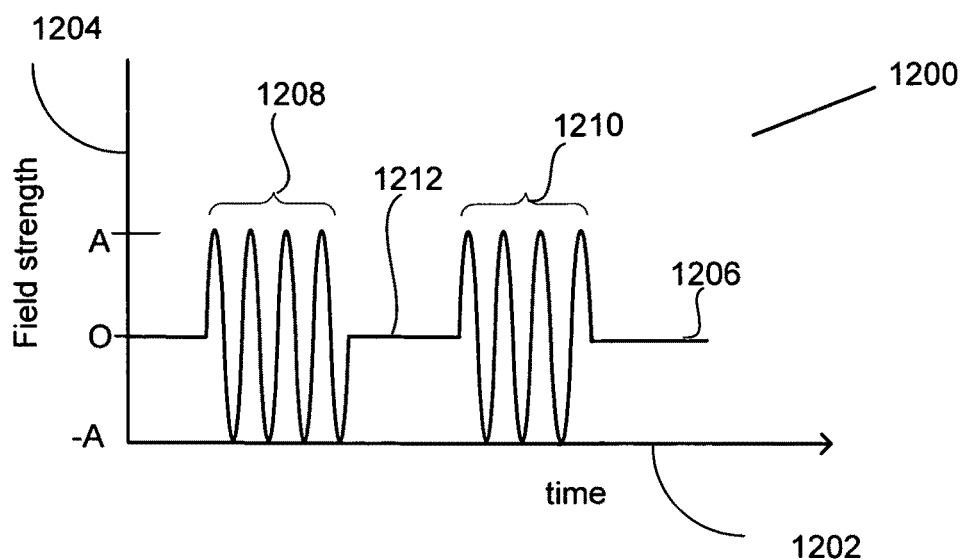
FIG. 30 depicts another exemplary control signal.

FIG. 30 depicts another example of an electromagnetic waveform. In plot 1200, time is plotted on axis 1202, and electromagnetic field strength is plotted on axis 1204. Trace 1206 includes bursts 1208 and 1210, during which the field strength varies between A and −A, at a selected frequency, and interval 1212, during which field strength is zero.

Figure 31:
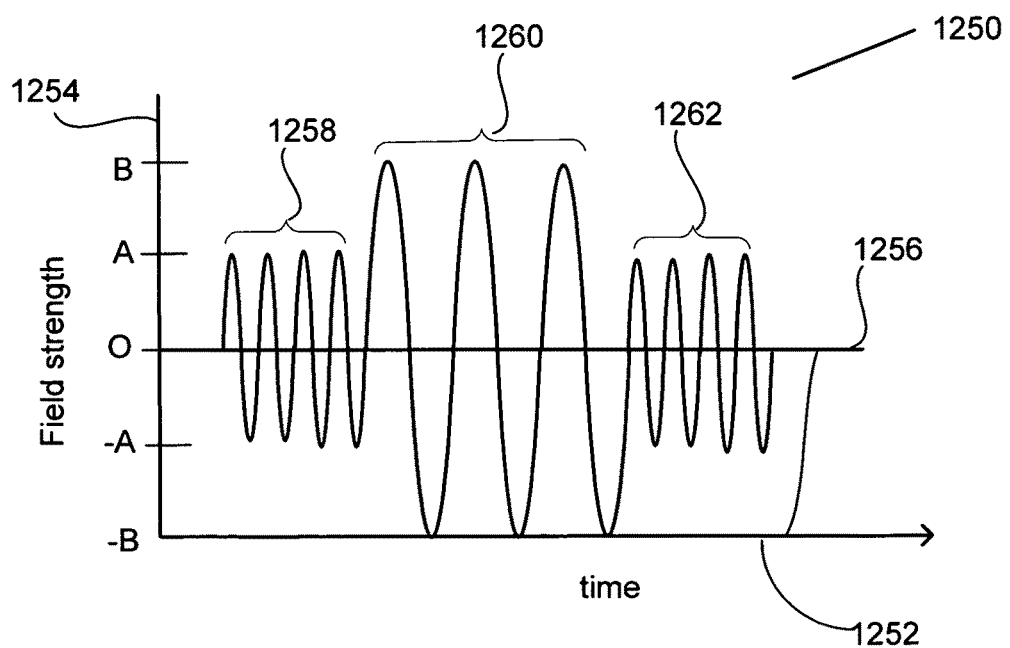
FIG. 31 depicts another exemplary control signal.

FIG. 31 depicts another example of an electromagnetic waveform. In plot 1250, time is plotted on axis 1252, and electromagnetic field strength is plotted on axis 1254. Trace 1256 includes bursts 1258, and 1262, during which the field strength varies between A and −A at a first frequency, and burst 1260, during which the field strength varies between B and −B at a second (lower) frequency. Different frequencies may be selectively received by certain individuals or classes of electromagnetically responsive control elements within a device or system including multiple electromagnetically responsive control elements. An electromagnetic control signal may be characterized by one or more frequencies, phases, amplitudes, or polarizations. An electromagnetic control signal may have a characteristic temporal profile and direction, and characteristic spatial dependencies. Acoustic control signals may be controlled in a similar manner and may include bursts of acoustic energy at various frequencies, intensities, duration, waveforms, etc. In some embodiments, an acoustic control signal may include bursts or pulses of acoustic energy, in which case the signal may also be characterized by a burst/pulse duration and inter-pulse/inter-burst interval. Frequency may be selected to provide desired tissue penetration and absorption properties. Lower frequency acoustic signals will generally penetrate deeper into the body, while higher frequency acoustic signals are more readily absorbed to produce heating. Audible acoustic signals may have frequencies between about 16 Hz and 20 kHz, while ultrasound signals have frequencies greater than about 20 kHz. Frequencies suitable for producing heating may be between about 0.5 and about 3 MHz, for example. Such frequencies are examples and not intended to be limiting; other frequencies may be used, and selection of appropriate frequencies may be determined for specific applications by those of skill in the art. Moreover, the acoustic signal may include more than one frequency and/or a series of frequencies (e.g., a "chirped" signal).

The magnetic or electric field control signal produced by the remote controller may have one or both of a defined magnetic field strength or a defined electric field strength. At low frequencies the electrical and magnetic components of an electromagnetic field are separable when the field enters a medium. Therefore, in static and quasi-static field application, the electromagnetic field control signal may be considered as an electrical field or a magnetic field. A quasi-static field is one that varies slowly, i.e., with a wavelength that is long with respect to the physical scale of interest or a frequency that is low compared to the characteristic response frequency of the object or medium; therefore, the frequency beyond which a field will no longer be considered 'quasi-static' is dependent upon the dimensions or electrodynamic properties of the medium or structure(s) influenced by the field.

Figure 32:
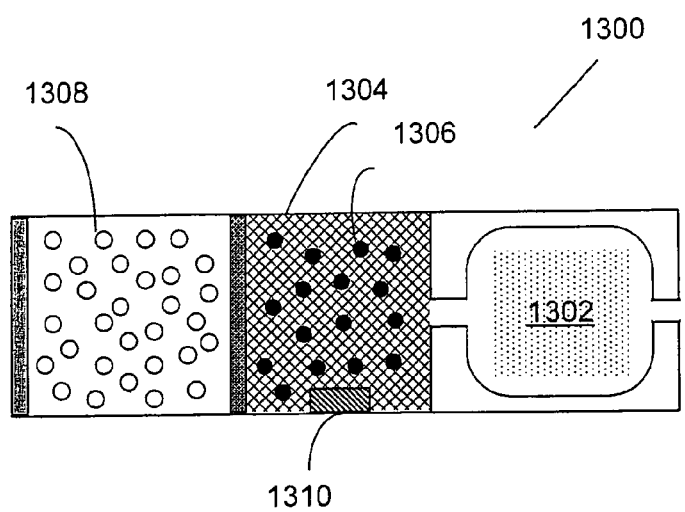
FIG. 32 illustrates an embodiment of a delivery device including a downstream fluid handling structure.

As depicted in various embodiments, e.g., as shown in FIGS. 6A-10B, the delivery reservoir may include an outlet through which the delivery fluid moves into an environment, for example by pumping or diffusion. In other embodiments, as depicted in FIG. 32, a delivery system 1300 may include a downstream fluid handling structure 1302 in fluid communication with the delivery reservoir 1304 and configured to receive fluid 1306 ejected from the delivery reservoir 1304 in response to the change in at least one of pressure or volume in the delivery reservoir 1304. The downstream fluid handling structure 1302 may include a chamber, as depicted in FIG. 32. Delivery device 1300 may also include a pump (e.g., and osmotic pump 1308) and an electromagnetically (or acoustically) responsive control element 1310.

Figure 33:
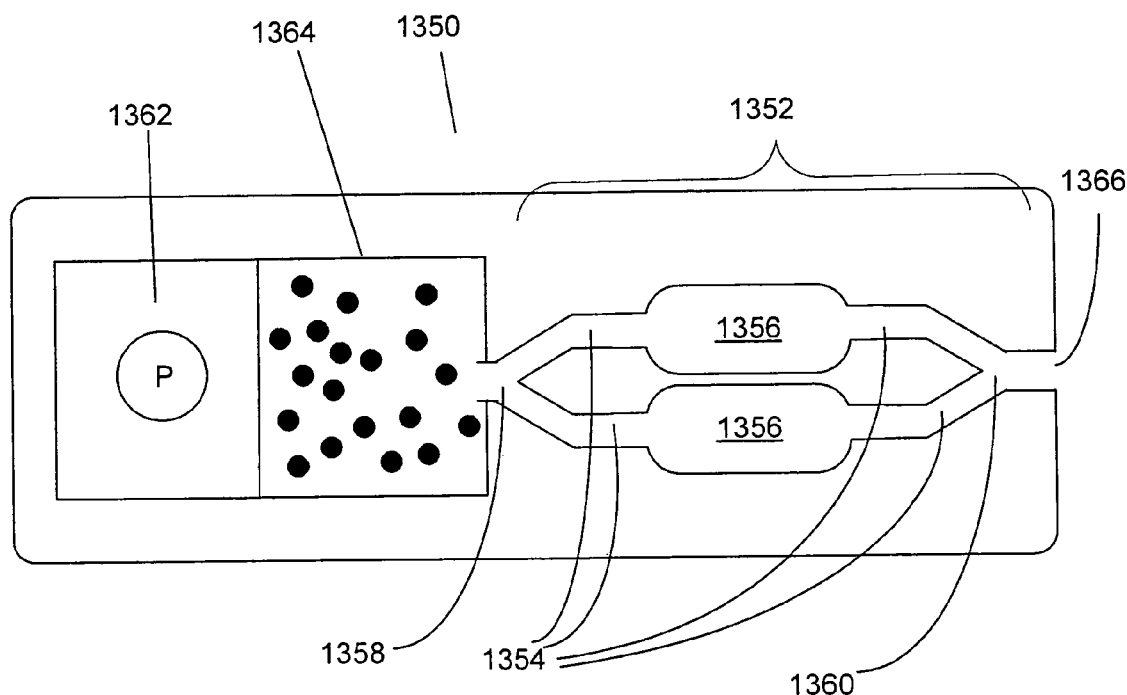
FIG. 33 illustrates another embodiment of a delivery device including a downstream fluid handling structure.

In other embodiments, e.g. delivery device 1350 shown in FIG. 33, a downstream fluid handling structure 1352 may include one or more channels 1354, chambers 1356, splitters 1358, mixers 1360, or other fluid handling structures, or various combinations thereof. Delivery device 1350 also includes pump 1362, delivery reservoir 1364, and outlet 1366. Examples of fluid handling structures suitable for use in selected embodiments are described in U.S. Pat. Nos. 6,146,103 and 6,802,489, and in Krauβ et al., "Fluid pumped by magnetic stress"; Bearing a date of Jul. 1, 2004; pp. 1-3; located at: http://arxiv.org/PS_cache/physics/pdf/0405/0405025.pdf, all of which are incorporated herein by reference. Fluid handling structures may include, but are not limited to, channels, chambers, valves, mixers, splitters, accumulators, pulse-flow generators, and surge-suppressors, among others.

Figure 34:
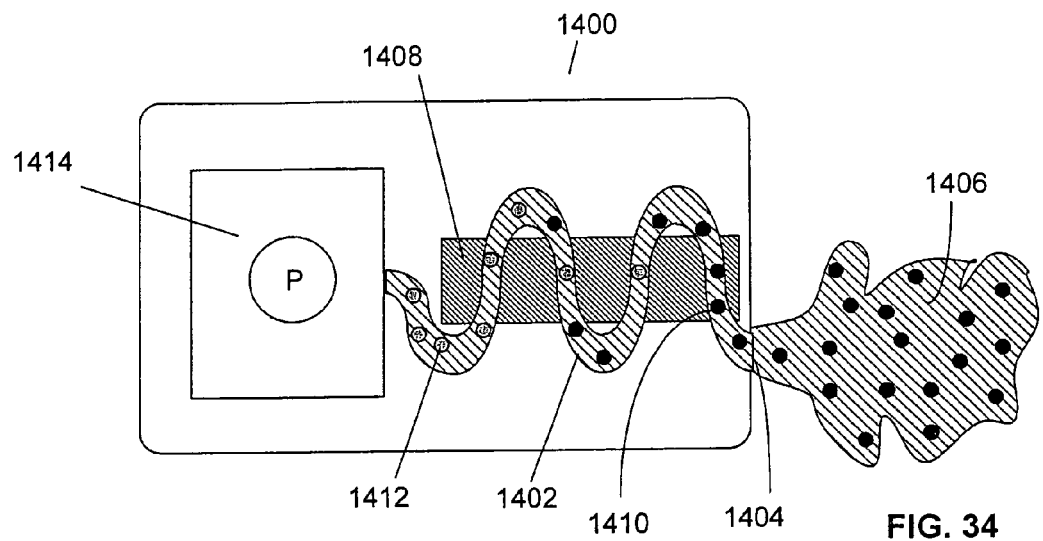
FIG. 34 illustrates an embodiment of a delivery device including a fluid containing structure.

Previously described embodiments of delivery devices have include a delivery reservoir that is substantially chamber-like in shape. However, delivery fluid may be contained in fluid-containing structures having various shapes and configurations. FIG. 34 illustrates a delivery device 1400 that includes a fluid-containing structure 1402 that takes the form of a channel. The fluid-containing structure 1402 may have at least one outlet 1404 through which a fluid may exit the fluid-containing structure 1402 to a downstream location; a delivery fluid 1406 contained within the fluid-containing structure 1402; a primary material contained within the fluid-containing structure and having a controllable effective concentration in the delivery fluid; at least one electromagnetically (or acoustically) responsive control element adapted 1408 for controlling the distribution of the primary material between a first active form 1410 carried in the delivery fluid and a second form 1412 in response to an incident electromagnetic control signal, the effective concentration being the concentration of the first active form in the delivery fluid; and a pump 1414 configured for pumping delivery fluid from the fluid-containing structure to the downstream location.

As noted previously, delivery devices as described herein may include various types of pumps. A pump suitable for use in a delivery device may include a mechanical pump, a displacement pump, a centrifugal pump, or a peristaltic pump. The choice of pump and method of construction thereof may depend upon the intended use of the delivery device, the delivery site, the dimensions of the delivery device, among other factors, as will be apparent to those of skill in the art. In some embodiments, the downstream location may be an environment. In some embodiments, the downstream location may be a downstream fluid handling structure, and in some embodiments, the downstream location may include a downstream environmental interface. An environmental interface may function to facilitate the distribution of a primary material into an environment.

Figure 35:
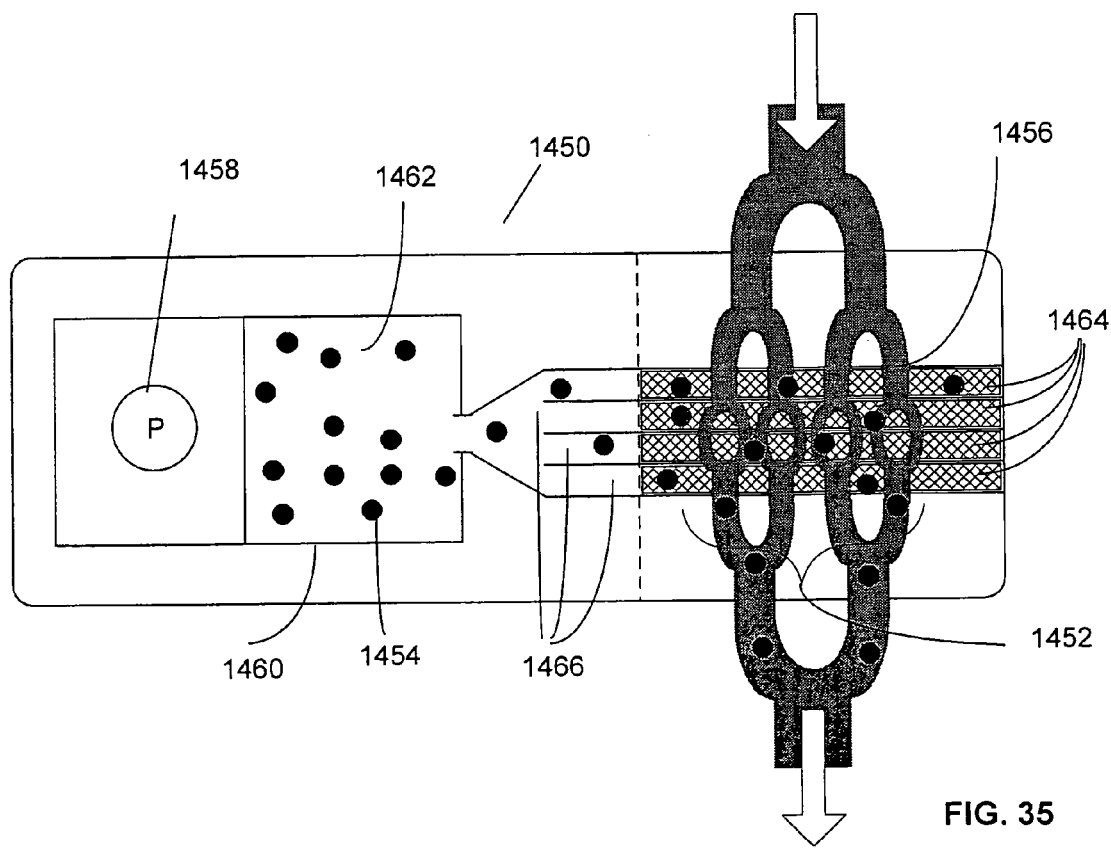
FIG. 35 illustrates an embodiment of a delivery device including an environmental interface.

FIG. 35 depicts an example of a delivery device 1450 including an environmental interface 1452. In the example of FIG. 35, the environmental interface 1452 provides for the delivery of primary material 1454 into blood flowing through capillaries 1456. Delivery device 1450 includes pump 1458 and a fluid-containing structure 1460 (here depicted as a delivery reservoir) containing delivery fluid 1462 carrying primary material 1454. Environmental interface 1452 includes substrate material 1464 capable of supporting growth of capillaries 1456. Distribution channel 1466 distributes delivery fluid 1462 to substrate material 1464, where primary material 1454 may diffuse into capillaries 1456 and be picked up by the blood.

In other embodiments, a delivery device as depicted generally in FIG. 34 may include any of various types of downstream fluid handling structures. The downstream fluid handling structure may include at least one-channel, of the type depicted in FIG. 33, or at least one chamber, for example as depicted in FIG. 32 or 33. The downstream fluid handling structure may include at least one mixer (e.g. 1360 in FIG. 33 or at least one splitter (e.g. 1354 in FIG. 33). In some embodiments, the downstream fluid handling structure may include a filter, for example, of the type depicted in FIG. 6D; it is contemplated that one or more filter may be placed at various downstream locations, not only at the outlet of the fluid-containing structure but potentially further downstream instead, or in addition.

FIG. 36 depicts a method of delivery a fluid through the use of a delivery device as described herein. The basic method includes receiving an electromagnetic control signal from a remote controller at step 1502; and responsive to the electromagnetic control signal, modifying an effective concentration of a primary material in a delivery fluid within a delivery reservoir at step 1504.

Figure 37:
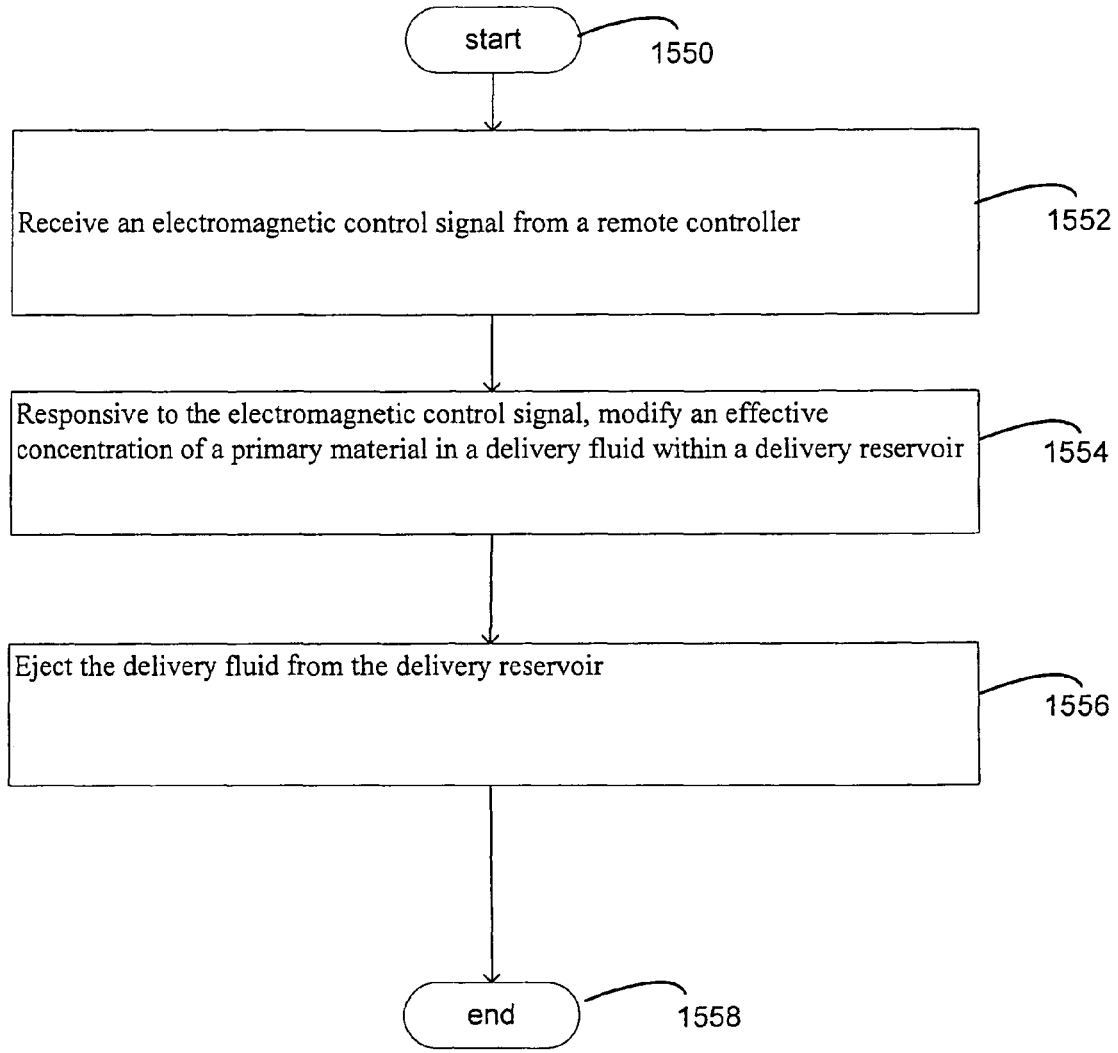
FIG. 37 is a flow diagram of a further method of delivering a fluid.

As shown in FIG. 37, an expanded version of the method may include receiving an electromagnetic control signal from a remote controller at step 1552; and responsive to the electromagnetic control signal, modifying an effective concentration of a primary material in a delivery fluid within a delivery reservoir at step 1554; followed by an additional step of 1556 of ejecting the delivery fluid from the delivery reservoir.

Figure 38:
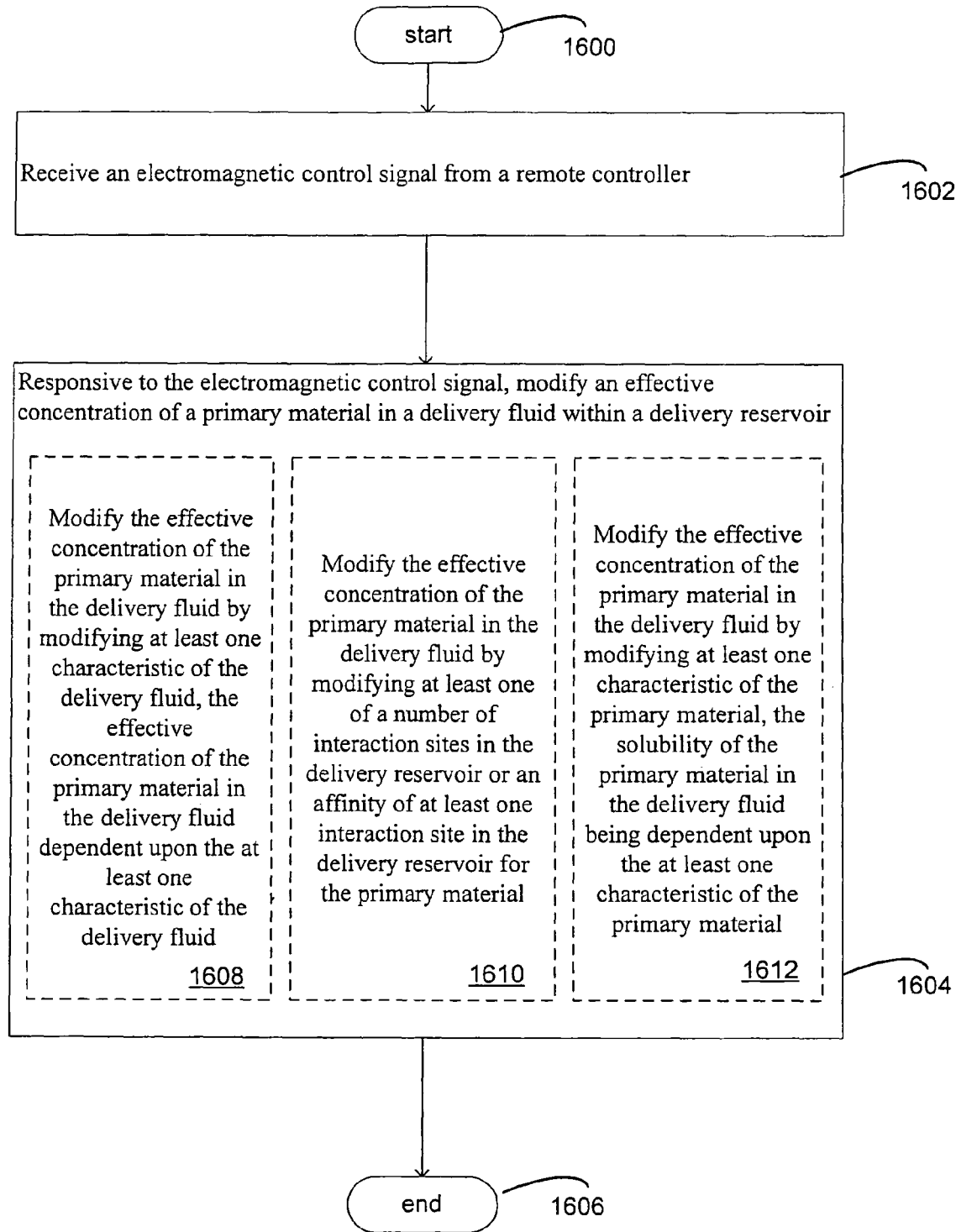
FIG. 38 is a flow diagram of a further method of delivery a fluid.

FIG. 38 provides further detail on a method including receiving an electromagnetic control signal from a remote controller at step 1602; and responsive to the electromagnetic control signal, modifying an effective concentration of a primary material in a delivery fluid within a delivery reservoir at step 1604 (comparable to steps 1502 and 1504 as shown in FIG. 36). The method may include modifying the effective concentration of the primary material in the delivery fluid by modifying at least one characteristic of the delivery fluid, the effective concentration of the primary material in the delivery fluid dependent upon the at least one characteristic of the delivery fluid, as shown in alternative step 1608 in FIG. 38. In this and other figures boxes containing optional or alternative steps are surrounded by a dashed line. The at least one characteristic may include, for example, temperature, pH, polarity, osmolality or chemical activity. As another alternative, as indicated at alternative step 1612 in FIG. 38, the method may include modifying the effective concentration of the primary material in the delivery fluid by modifying at least one characteristic of the primary material, the solubility of the primary material in the delivery fluid being dependent upon the at least one characteristic of the primary material. The at least one characteristic includes temperature, charge, polarity, osmolality, conformation, orientation, or chemical activity. As a further alternative, indicated at 1610 in FIG. 38, the method may include modifying the effective concentration of the primary material in the delivery fluid by modifying at least one of a number of interaction sites in the delivery reservoir or an affinity of at least one interaction site in the delivery reservoir for the primary material. The affinity of the at least one interaction site for the primary material may be modified by modifying the temperature, charge, polarity, osmolality, surface energy, orientation, conformation, chemical activity or chemical composition of the at least one interaction site or in the vicinity of the at least one interaction site. The number of interaction sites may be modified by stretching, compressing, unfolding, or changing a conformation of at least a portion of the delivery reservoir, for example.

A method as shown in FIGS. 36-48 may include receiving the electromagnetic control signal with an electromagnetically responsive material, which may include, for example, a permanently magnetizable material, a ferromagnetic material, a ferrimagnetic material, a ferrous material, a ferric material, a dielectric or ferroelectric or piezoelectric material, a diamagnetic material, a paramagnetic material, and an anti-ferromagnetic material. The method may include a step of ejecting the delivery fluid into an environment, which may include, for example, the body of an organism, a body of water, or a contained fluid volume. Alternative, the method may include ejecting the delivery fluid into a downstream environmental interface or a downstream fluid-handling structure, which may include a channel, a chamber, a mixer, a separator, or combinations thereof.

Figure 39:
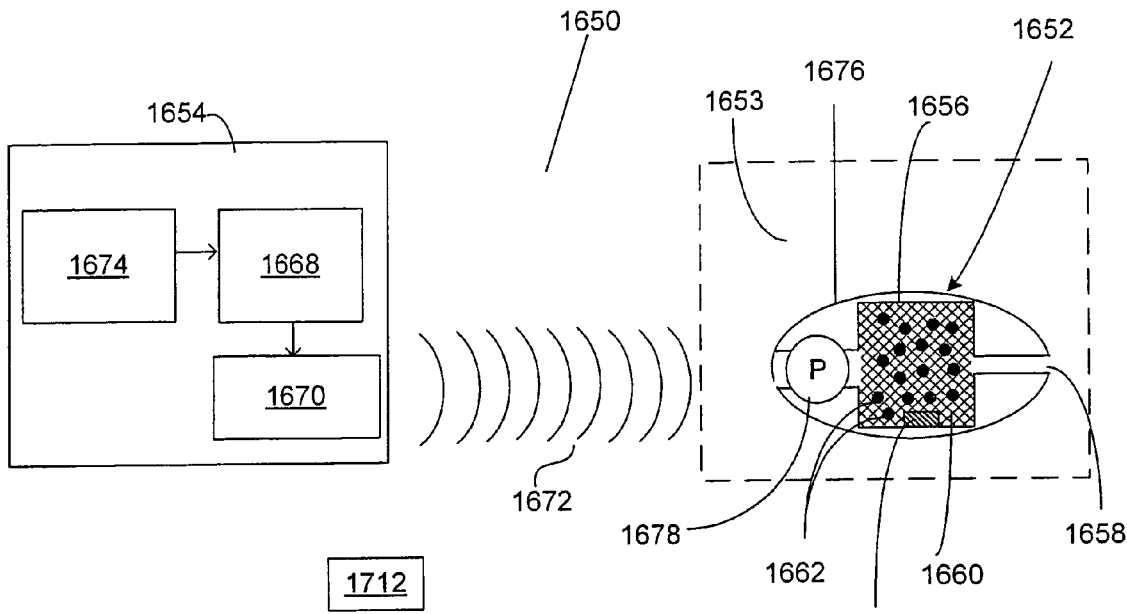
FIG. 39 is a schematic diagram of an embodiment of a system including a remote controller and a delivery device.

FIG. 39 depicts a delivery system 1650 that includes a delivery device 1652 and a remote controller 1654. Delivery device 1652 includes fluid-containing structure 1656 having at least one outlet 1658 through which fluid may exit the fluid-containing structure 1656; a delivery fluid 1660 contained within the fluid-containing structure 1656; a primary material 1662 contained within the fluid-containing structure 1656 and having a controllable effective concentration in the delivery fluid 1660; and at least one electromagnetically responsive control element 1664 adapted for modifying the distribution of the primary material 1662 between a first active form carried in the delivery fluid and a second form in response to an incident electromagnetic control signal to modify the effective concentration of the primary material in the delivery fluid, the effective concentration being the concentration of the first active form in the delivery fluid. Remote controller 1654 includes an electromagnetic signal generator 1668 capable of producing an electromagnetic control signal sufficient to activate the electromagnetically responsive control element 1664 of the delivery device 1652 located in an environment 1653 to change the effective concentration of the primary material in the delivery fluid 1660 within the fluid-containing structure 1656 of the delivery device 1652; and an electromagnetic signal transmitter 1670 capable of wirelessly transmitting the electromagnetic control signal 1672 to the electromagnetically responsive control element of the delivery device in the environment. The remote controller may include electrical circuitry 1674, which may include at least one of hardware, firmware, or software configured to control generation of the electromagnetic control signal. The remote controller 1654 may include an electromagnetic signal generator 1668 configured to generate a static or quasi-static electrical field control signal, a static or quasi-static magnetic field control signal, a radio-frequency electromagnetic control signal sufficient, a microwave electromagnetic control, an infrared electromagnetic control signal, a millimeter wave electromagnetic control signal, an optical electromagnetic control signal, or an ultraviolet electromagnetic control signal sufficient to activate the electromagnetically responsive control element to control the effective concentration of the primary material within the fluid-containing structure. The remote controller may include an electromagnetic signal generator configured to generate a rotating electromagnetic control signal.

Delivery device 1652 may include a body structure 1676 adapted for positioning in an environment 1653 selected from a body of an organism, a body of water, or a contained fluid volume. For example, body structure 1676 may be adapted for positioning in a contained fluid volume selected from an industrial fluid volume, an agricultural fluid volume, a swimming pool, an aquarium, a drinking water supply, a portable water supply, and an HVAC system cooling water supply. Delivery device 1652 may include a pump 1678, as described generally elsewhere herein.

The electromagnetically responsive control element 1664 may include a magnetically or electrically active material including at least one permanently magnetizable material, ferromagnetic material, ferrimagnetic material, ferrous material, ferric material, dielectric material, ferroelectric material, piezoelectric material, diamagnetic material, paramagnetic material, metallic material, or antiferromagnetic material. In some embodiments, the electromagnetically responsive control element may include a polymer, ceramic, dielectric, metal, shape memory material, or a combination of a polymer and a magnetically or electrically active component.

Figure 40:
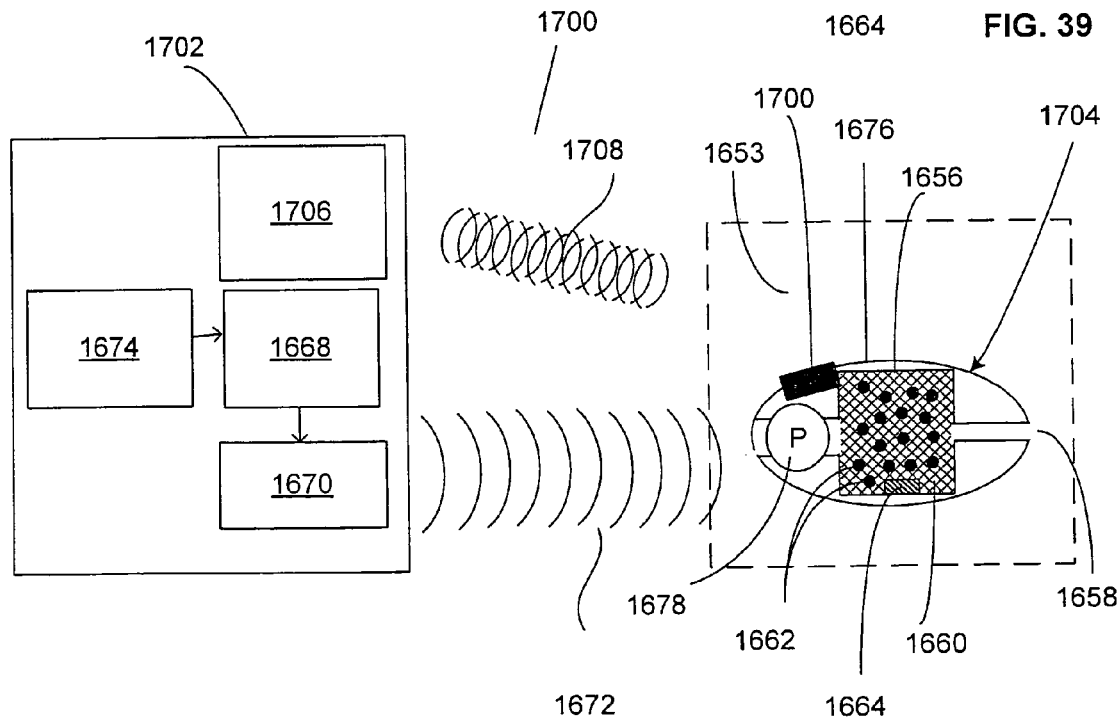
FIG. 40 is a diagram of an embodiment of a delivery system including a delivery device with an RFID.

FIG. 40 depicts a delivery system 1700, including remote controller 1702, and delivery device 1704. Delivery device 1704 includes fluid-containing structure 1656, having outlet 1658 and containing delivery fluid 1660 and primary material 1662. Delivery device 1704 also includes electromagnetically responsive control element 1664 for controlling the effective concentration of primary material 1662 in delivery fluid 1660. Delivery device 1704 may include body structure 1676 adapted for placement in environment 1653, and pump 1678. Delivery device 1704 may also include RFID 1700. Remote controller 1702 includes RF interrogation signal generator 1706 for generating an RF interrogation signal 1708, which may be tuned to the RFID. Remote controller 1702 includes electromagnetic signal generator 1668, electromagnetic signal transmitter 1670, electrical circuitry 1674, which function generally as described in connection with FIG. 39.

Figure 41:
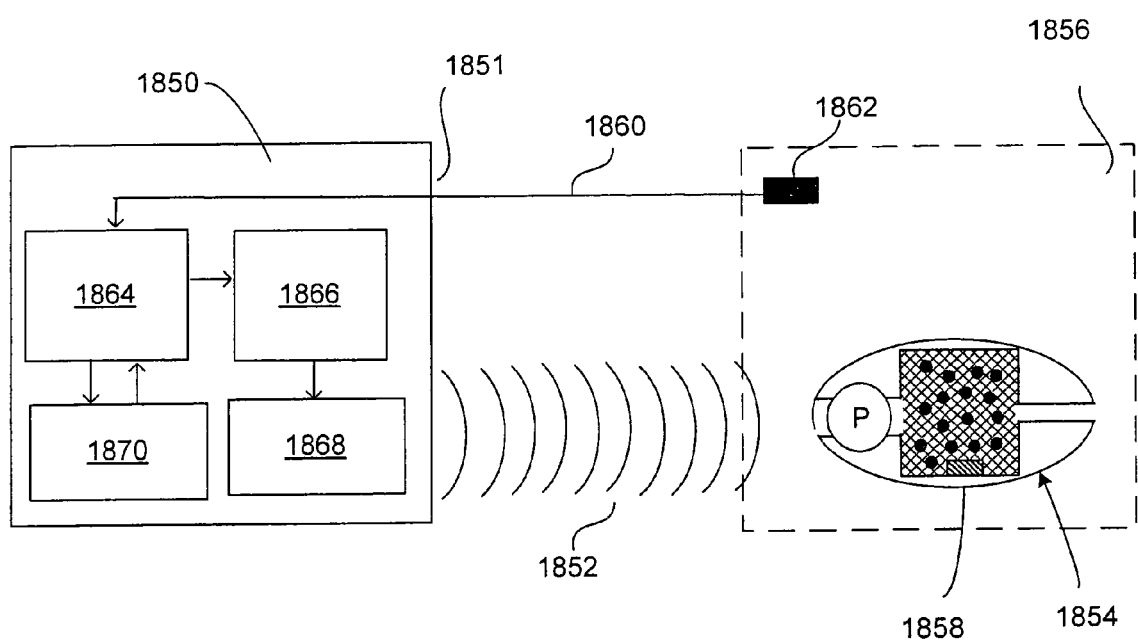
FIG. 41 is a schematic diagram of an embodiment a system including a remote controller, a delivery device, and a sensor.

FIG. 41 illustrates a delivery system including a remote controller 1850 that produces electromagnetic control signal 1852 that is transmitted to delivery device 1854 in environment 1856. Electromagnetic control signal 1852 is received by electromagnetically responsive control element 1858 in delivery device 1854. Remote controller 1850 may include a signal input 1851 adapted for receiving a feedback signal 1860 sensed from an environment 1856 by a sensor 1862, wherein the electromagnetic signal 1852 is produced based at least in part upon the feedback signal 1860 sensed from the environment. For example, the feedback signal 1852 may correspond to the osmolality or the pH of the environment, the concentration or chemical activity of a chemical in the environment, a temperature or pressure of the environment, or some other sensed signal. Remote controller 1850 may include electrical circuitry 1864, signal generator 1866, signal transmitter 1868, and memory 1870. Feedback from sensor 1862 may be sent over a wire connection or, in some embodiments, transmitted wirelessly. Remote controller may include a signal input adapted for receiving a feedback signal corresponding to one or more parameters sensed from the environment, wherein the electromagnetic control signal is produced based at least in part upon the feedback signal sensed from the environment. For example, the feedback signal corresponds to the concentration or chemical activity of a chemical in the environment.

Figure 42:
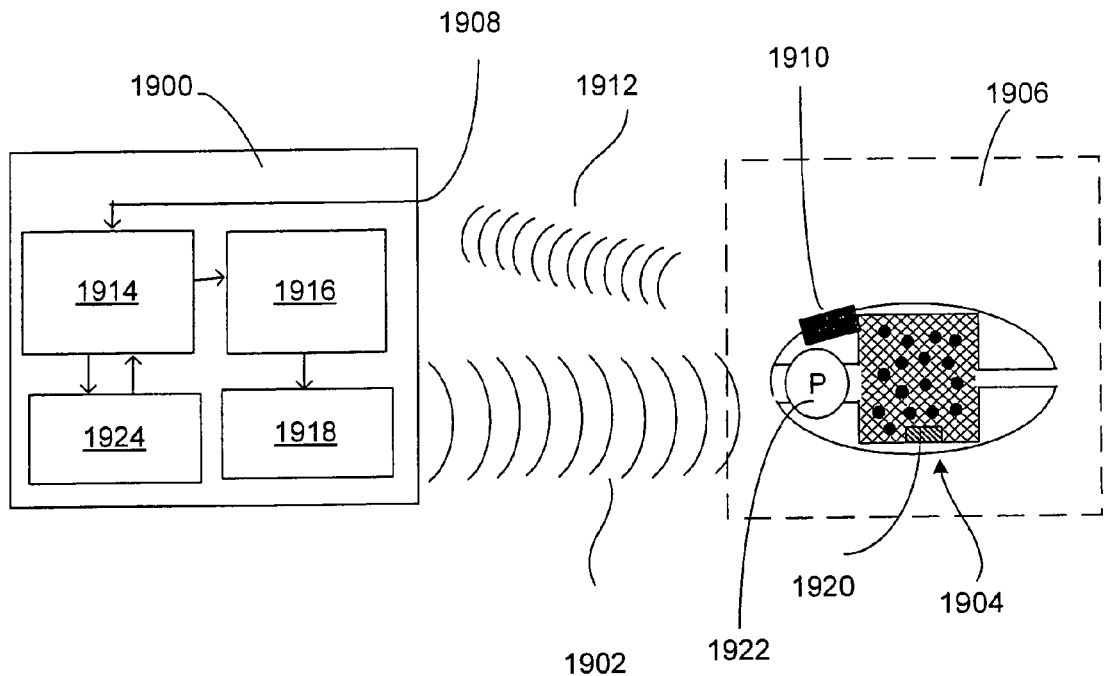
FIG. 42 is a schematic diagram of an embodiment a system including a remote controller and a delivery device including a sensor.

FIG. 42 illustrates another embodiment of a delivery system, including remote controller 1900, which transmits electromagnetic control signal 1902 to delivery device 1904 in environment 1906. Remote controller 1900 may include a signal input 1908 adapted for receiving a feedback signal 1912 from sensor 1910 in delivery device 1904. Electromagnetic control signal 1902 may be produced based at least in part upon the feedback signal 1912 corresponding to one or more parameters sensed from the delivery device. In some embodiments, the feedback signal may correspond to the concentration or chemical activity of a chemical within or around the delivery device. In some embodiments, the feedback signal from the delivery device may correspond to the osmolality or the pH within or around the delivery device, the concentration or chemical activity of a chemical within or around the delivery device, a temperature or pressure within or around the delivery device, the pumping rate of the delivery device, or some other parameter sensed from the delivery device. In others, the feedback signal may correspond to the pumping rate of the delivery device, produced, for example, by pump 1922. In some embodiments, sensor 1910 may be configured for detecting at least one parameter from at least a portion of an environment surrounding the delivery device. The electromagnetic signal 1902 may be determined based at least in part upon the feedback signal 1912. Examples of sensors are described in U.S. Pat. No. 6,935,165, and U.S. Patent Publication 2004/0007051, both of which are incorporated herein by reference. Delivery device 1904 includes electromagnetically responsive control element 1920. Feedback signal 1912 may be transmitted wirelessly back to remote controller 1900. Remote controller 1900 may include processor 1914, signal generator 1916, signal transmitter 1918, and memory 1924.

Figure 43:
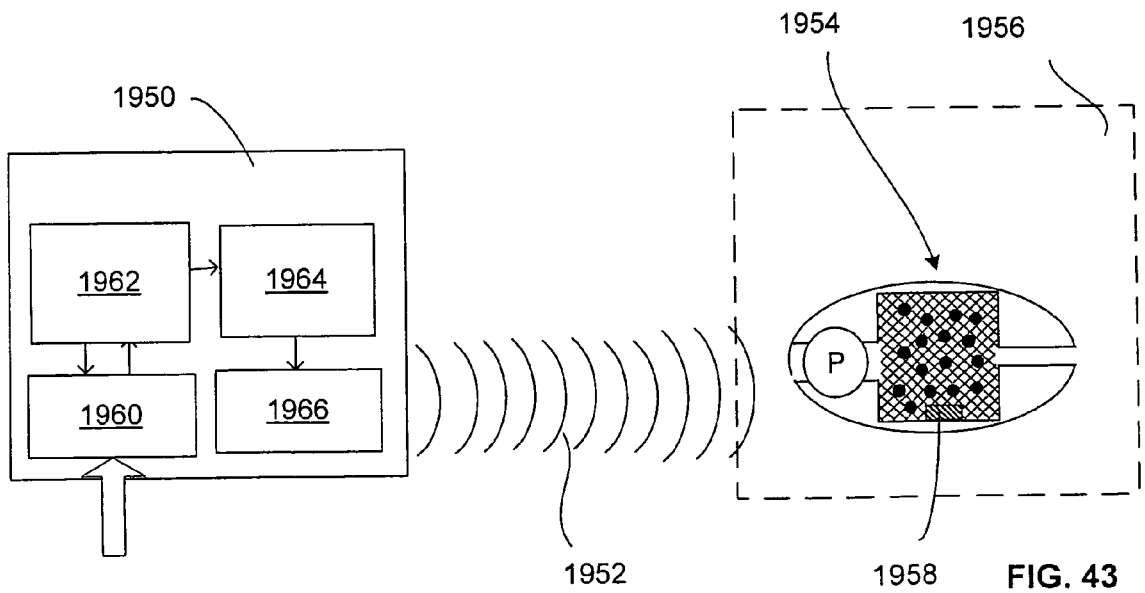
FIG. 43 is a schematic diagram of another embodiment of system including a remote controller and a delivery device.

As illustrated in FIG. 43, in some embodiments, the remote controller may be configured to receive user input of control parameters. Remote controller 1950 includes input 1960 for receiving input of information or instructions from a user such as, for example, commands, variables, durations, amplitudes, frequencies, waveforms, data storage or retrieval instructions, patient data, etc. As in the other embodiments, remote controller 1950 transmits electromagnetic control signal 1952 to delivery device 1954 in environment 1956, where it activates electromagnetically responsive control element 1958. Input 1960 may include one or more input devices such as a keyboard, keypad, microphone, mouse, etc. for direct input of information from a user, or input 1960 may be any of various types of analog or digital data inputs or ports, including data read devices such as disk drives, memory device readers, and so forth in order to receive information or data in digital or electronic form. Data or instructions entered via input 1960 may be used by electrical circuitry 1962 to modify the operation of remote controller 1950 to modulate generation of an electromagnetic control signal 1952 by signal generator 1964 and transmission of the control signal 1952 by transmitter 1966. Any of the systems depicted in FIGS. 39-43 may be implemented using acoustic control signals, in addition to or instead of electromagnetic control and/or feedback signals, and such embodiments are considered to fall within the scope of the present disclosure.

Figure 44:
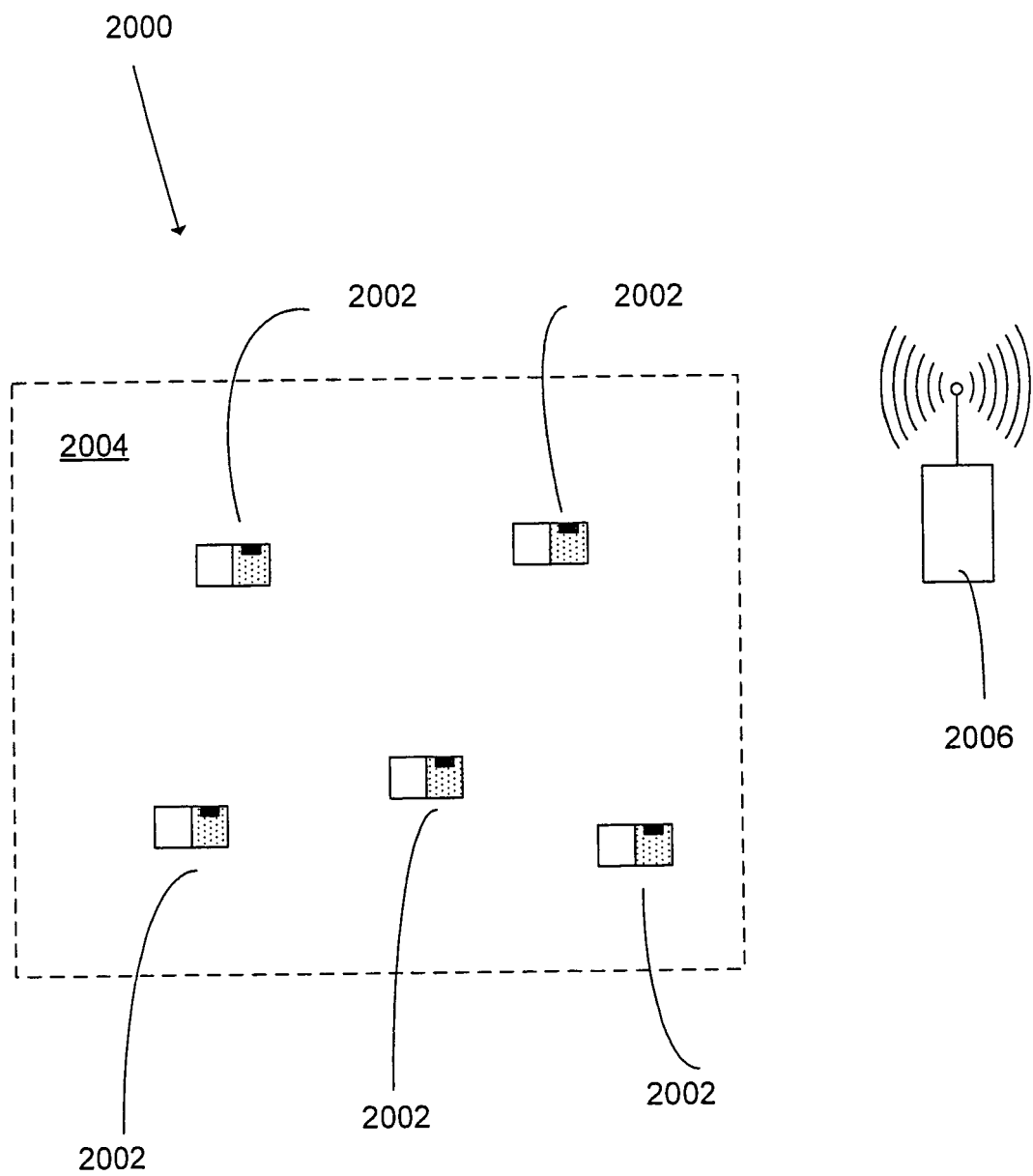
FIG. 44 is an embodiment of a system including a remote controller and a plurality of delivery devices in an environment.

FIG. 44 illustrates a delivery system that includes a plurality of delivery devices, where two or more of the plurality of delivery devices are controlled by the remote controller. A delivery device may include a plurality of selectively activatable control elements, each associated with a particular fluid handling element, which may thus be controlled to perform multiple fluid-handling or reaction steps in a particular sequence. It is also contemplated that a delivery system may include a plurality of delivery devices which may be of the same or different types. As shown in FIG. 44, a delivery system 2000 may include a plurality of identical delivery devices 2002 distributed throughout an environment 2004 in order to perform a particular chemical reaction or process at a plurality of locations within the environment, and controlled by a remote controller 2006. Alternatively, a delivery system may include a plurality of different delivery devices at different locations within an environment, each performing or controlling a reaction suited for the particular location. The invention as described herein is not limited to devices or systems including any specific number or configuration of electromagnetically or acoustically responsive control elements within a delivery device, or specific number or configuration of delivery devices or remote controllers within a delivery system. Depending upon the particular application of a system, electromagnetically responsive control elements and/or delivery devices may be controlled in a particular pattern to producing a desired distribution of a delivery material in an environment. Control of such systems may be performed with the use of suitable hardware, firmware, and/or software, through one or a plurality of remote controllers.

The remote controller used in the system depicted in FIG. 44 may include an electromagnetic signal generator capable of producing an electromagnetic control signal sufficient to activate electromagnetically responsive control elements in a plurality of delivery devices located in an environment to change an effective concentration of primary material in a delivery fluid within a fluid-containing structure of each of the devices. In a related embodiment, the remote controller may include a plurality of signal inputs adapted for receiving signals from the plurality of delivery devices, the plurality of signal inputs coupled to a microprocessor configured to generate the electromagnetic control signal based upon the plurality of signals.

Selective activation or control of electromagnetically responsive control elements may be achieved by configuring electromagnetically responsive control elements to be activated by electromagnetic control signals having particular signal characteristics, which may include, for example, particular frequency, phase, amplitude, temporal profile, polarization, and/or directional characteristics, and spatial variations thereof. For example, different control elements may be responsive to different frequency components of a control signal, thereby allowing selective activation of the different control elements. The remote controller may be configured to produce a rotating electromagnetic signal, the rotating electromagnetic signal capable of activating the two or more delivery devices independently as a function of the orientation of the rotating electromagnetic signal.

Figure 45:
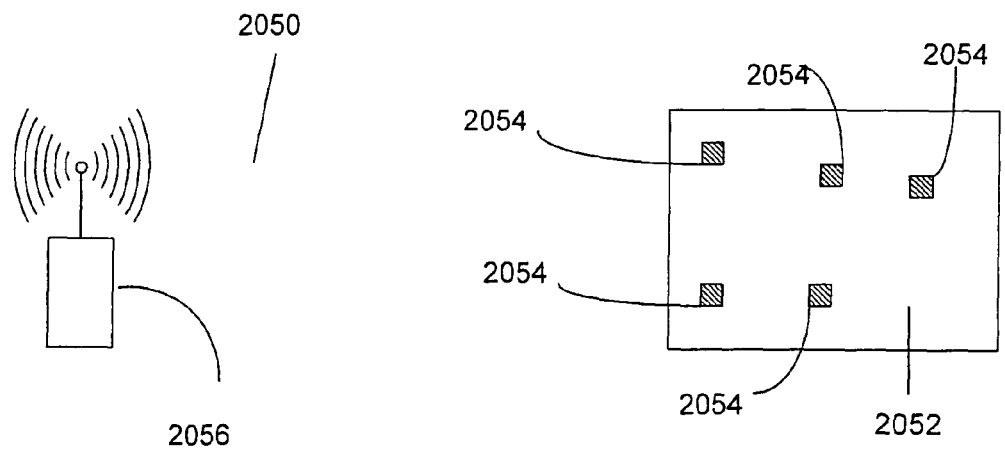
FIG. 45 is a schematic of an embodiment of a delivery system.

As shown in FIG. 45, in still other embodiments, a delivery system 2050 may include a delivery device 2052 that includes a plurality of electromagnetically responsive control elements 2054, responsive to one or more remote controller 2056. A plurality of control elements 2054 may be used, for example, to control a plurality of locations or functions in delivery device 2052.

Figure 46:
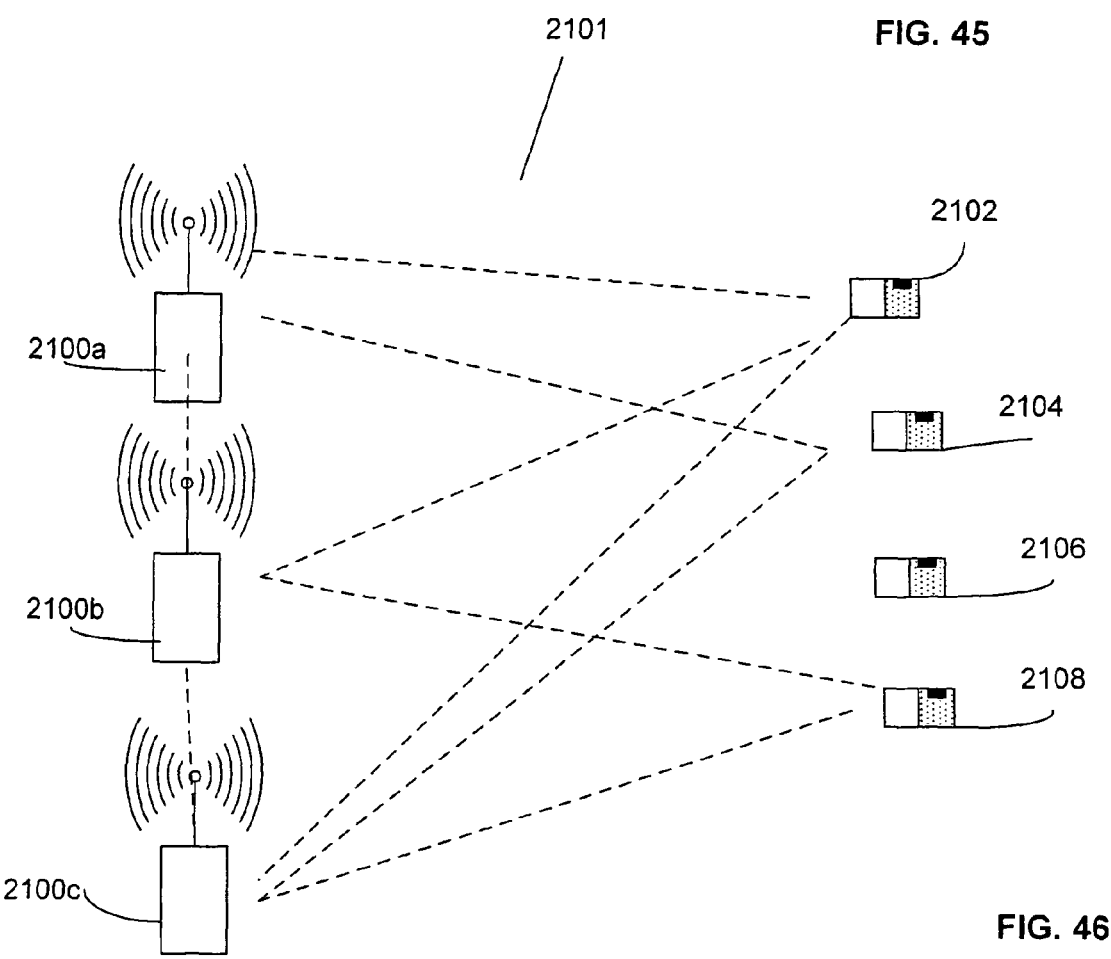
FIG. 46 is a schematic of a further embodiment of a delivery system.

As shown in FIG. 46, in some embodiments, a delivery system 2101 or may include a plurality of delivery devices 2102, 2104, 2106, and 2108, and a plurality of remote controllers 2100*a*, 2100*b*, 2100*c*. As shown in FIG. 46, each delivery device may be controlled by one or more control signals produced in a distributed fashion by two or more of the plurality of remote controllers 2100*a*-2100*c*.

Figure 47:
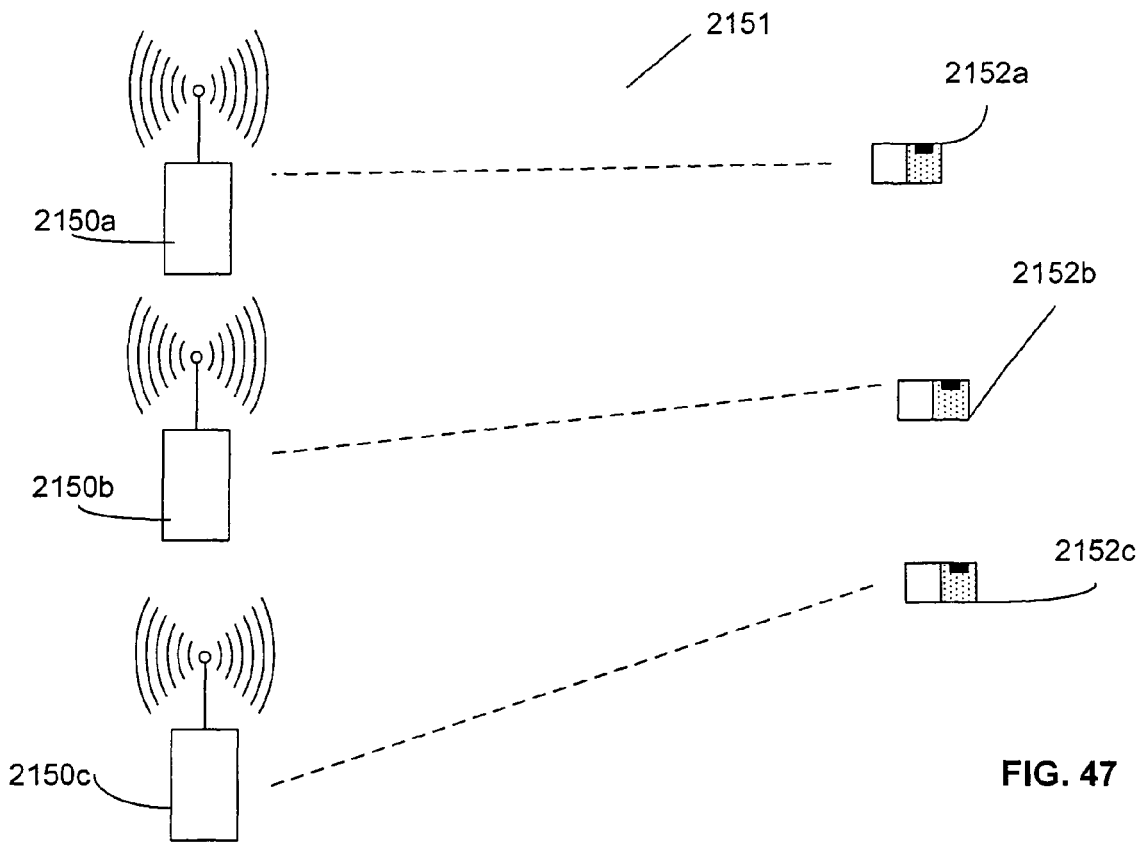
FIG. 47 is a schematic of a further embodiment of a delivery system.

As shown in FIG. 47, in some embodiments a delivery system 2151 may include a plurality of delivery devices 2152*a*, 2152*b*, and 2152*c* and a plurality of remote controllers 2150*a*, 2150*b*, and 2150*c*, each delivery device may be controlled by a separate remote controller, for example delivery device 2152*a* controlled by remote controller 2150*a*, delivery device 2152*b* controlled by remote controller 2150*b*, and delivery device 2152*c* controlled by remote controller 2150*c*.

Figure 48:
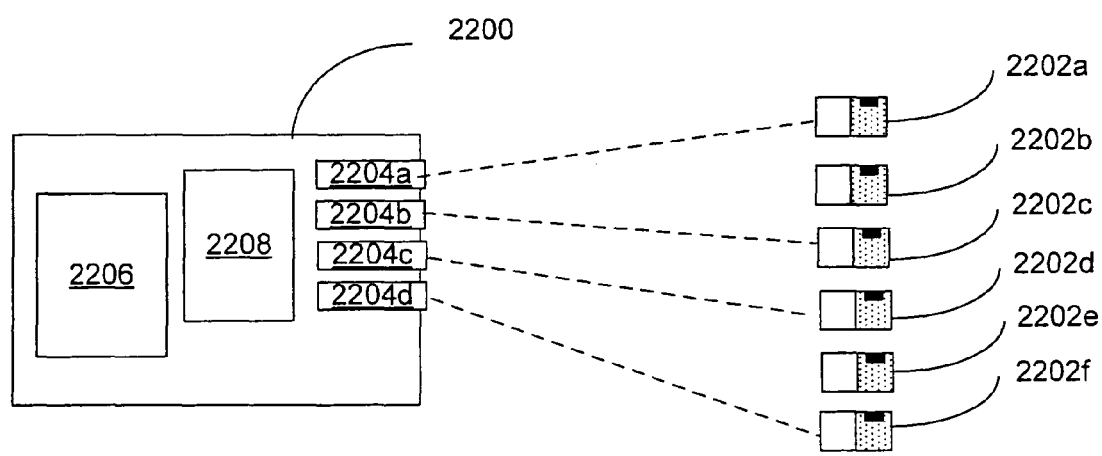
FIG. 48 is a schematic of another embodiment of a delivery system.

In still other embodiments, as shown in FIG. 48, a remote controller 2200 may include a plurality of transmission channels 2204*a*, 2204*b*, 2204*c*, and 2204*d*, for example (more or fewer channels may be used, without limitation). Remote controller 2200 may also include channel allocation hardware or software 2206 configured to allocate usage of the plurality of transmission channels 2204*a*-2204*d* for the transmission of the electromagnetic control signal from signal transmitter 2208 to selected delivery devices of the plurality of delivery devices 2202*a*-2202*f*.

Figure 49:
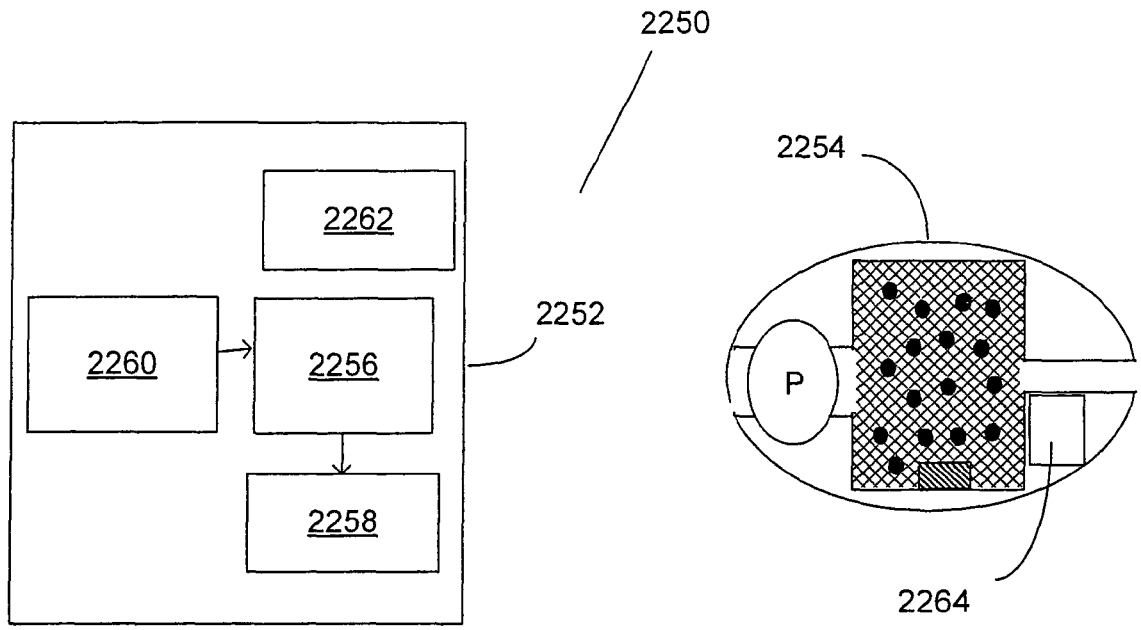
FIG. 49 depicts an embodiment of a delivery system including encryption.

In another embodiment of a delivery system 2250 shown in FIG. 49, the remote controller 2252 may include encryption hardware or software 2262 configured to encrypt one or more control signal components, wherein the encrypted one or more control signal components are receivable by a delivery device 2254 including a corresponding decryption key 2264. Remote controller 2252 may include signal generator 2256, signal transmitter 2258, and electrical circuitry 2260, as described generally elsewhere.

Figure 50:
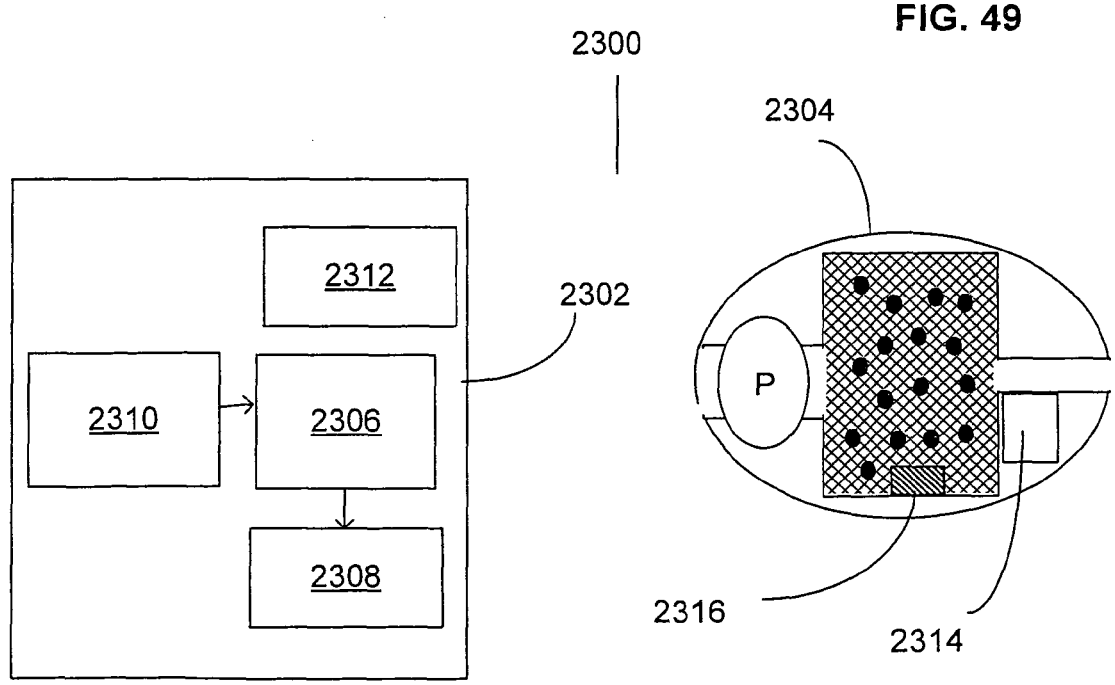
FIG. 50 depicts an embodiment of a delivery system that utilizes an authentication procedure.

In another embodiment of a delivery system 2300 shown in FIG. 50, the remote controller 2302 may include authentication hardware or software 2312 configured to perform an authentication procedure with a delivery device 2304, wherein the remote controller 2302 is configured to produce activation of the electromagnetically responsive control element 2316 of an authenticated delivery device but not the electromagnetically responsive control element of a non-authenticated delivery device. Again, remote controller 2302 may include signal generator 2306, signal transmitter 2308, and electrical circuitry 2310, as described generally elsewhere, and authentication portion 2314, which may include hardware, firmware or software configured for performing an authentication protocol with remote controller 2302.

Referring back to FIG. 40, remote controller 1702 may include an interrogation signal generator 1706 for generating a transmittable RFID interrogation signal. The remote controller may also include an interrogation signal transmitter for transmitting the transmittable RFID interrogation signal; an interrogation signal receiver for receiving a returned RFID interrogation signal from an RFID in a delivery device; and RFID detection circuitry configured to detect the presence of a selected RFID from a returned RFID interrogation signal. Upon detection of the presence of the selected RFID, to remote controller 1702 may generate and transmit a control signal configured for receipt by the delivery device including the selected RFID.

In various embodiments of the remote controller described herein, the generated electromagnetic control signal may have a defined magnetic field strength, or alternatively, or in addition, a defined electric field strength. Depending upon the intended application, the electromagnetic control signal may have signal characteristics sufficient to produce a change in dimension of the electromagnetically responsive control element, a change in temperature of at least a portion of the electromagnetically responsive control element, a change in conformation or configuration of the electromagnetically responsive control element, or a change in orientation or position of the electromagnetically responsive control element. The remote controller may include an electromagnetic signal generator that includes an electromagnet or electrically-polarizable element, or at least one permanent magnet or electret. Systems as depicted in FIGS. 44-50 may utilize acoustic rather than electromagnetic control signals.

FIG. 51 depicts the steps of a method of delivering a material, comprising delivering an electromagnetic distribution control signal to an environment containing a delivery device, the delivery device including an electromagnetically responsive control element and a fluid-containing structure containing a delivery fluid and a quantity of a primary material distributed between a first active form carried in the delivery fluid and a second form according to a first distribution, the primary material distributed according to the first distribution having a first effective concentration in the delivery fluid equal to the concentration of the first active form in the delivery fluid, the electromagnetic distribution control signal having signal characteristics receivable by the electromagnetically responsive control element and sufficient to produce a change in the distribution of the primary material between the first active form and the second form to a second distribution, the primary material distributed according to the second distribution having a second active concentration in the delivery fluid, at step 2352; and delivering an electromagnetic delivery control signal to the environment containing the delivery device, the electromagnetic delivery control signal sufficient to produce pumping of the delivery fluid out of the fluid-containing structure, the delivery fluid containing the primary material at the second effective concentration in the delivery fluid at step 2354.

Figure 52:
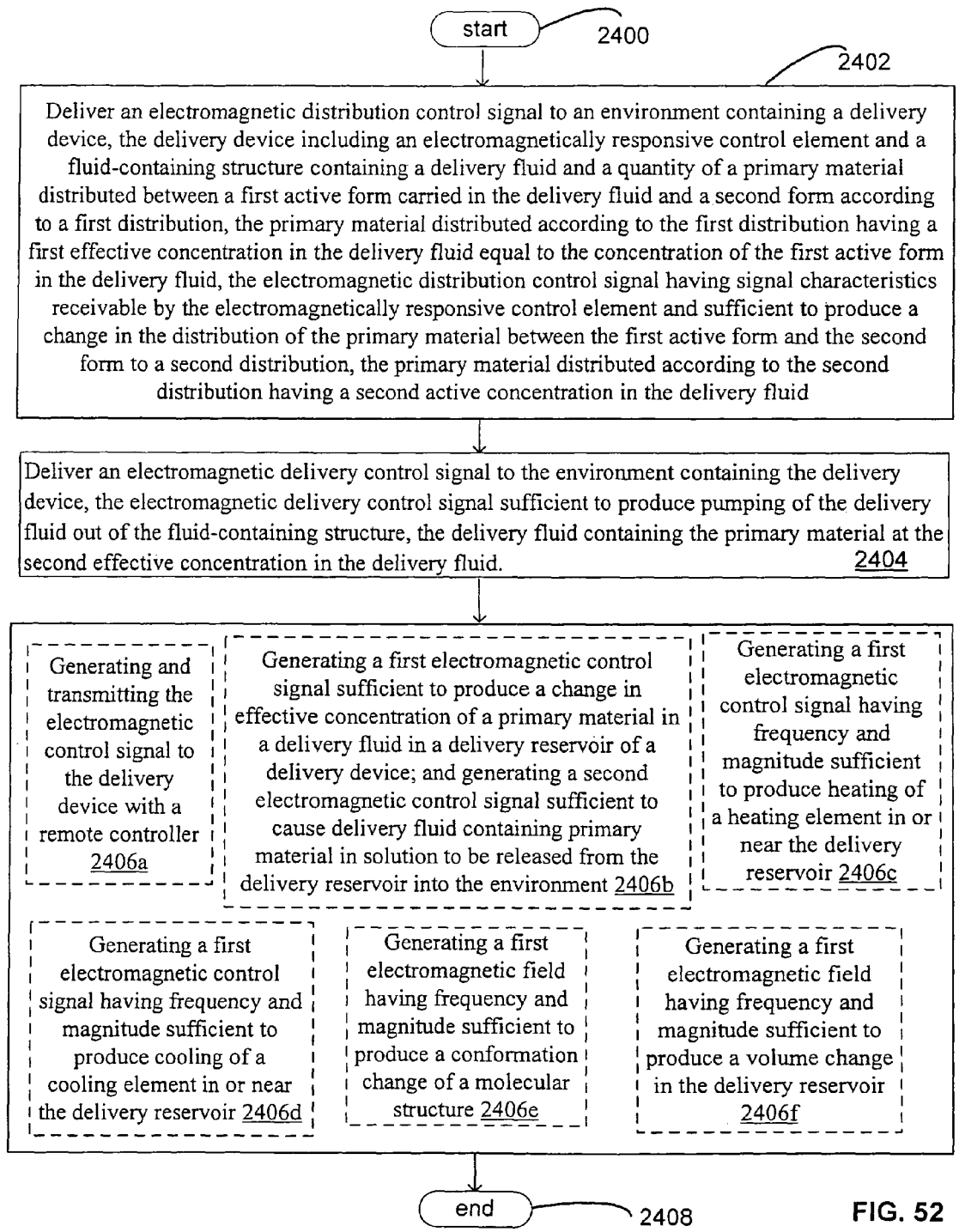
FIG. 52 is a flow diagram of a method of delivering a material.

FIG. 52 shows further variations of the method of FIG. 51. The method of FIG. 52 include steps of delivering and electromagnetic distribution control signal at step 2402 and delivering an electromagnetic delivery control signal at step 2404 (e.g., as in FIG. 51), followed by a step of generating an electromagnetic control signal according to a number of optional steps. For example, the method may include generating and transmitting the electromagnetic control signal to the delivery device with a remote controller, as shown at 2406a. Alternatively, the method may include generating a first electromagnetic control signal sufficient to produce a change in effective concentration of a primary material in a delivery fluid in a delivery reservoir of a delivery device; and generating a second electromagnetic control signal sufficient to cause delivery fluid containing primary material in solution to be released from the delivery reservoir into the environment, as shown at 2406b. Or, the method may include generating a first electromagnetic control signal having frequency and magnitude sufficient to produce heating of a heating element in or near the delivery reservoir, as shown at 2406c. Alternatively, the method may include generating a first electromagnetic control signal having frequency and magnitude sufficient to produce cooling of a cooling element in or near the delivery reservoir, as shown at 2406d, generating a first electromagnetic field having frequency and magnitude sufficient to produce a conformation change of a molecular structure, as shown at 2406e, or generating a first electromagnetic field having frequency and magnitude sufficient to produce a volume change of a material a molecular structure, as shown at 2406f.

Figure 53:
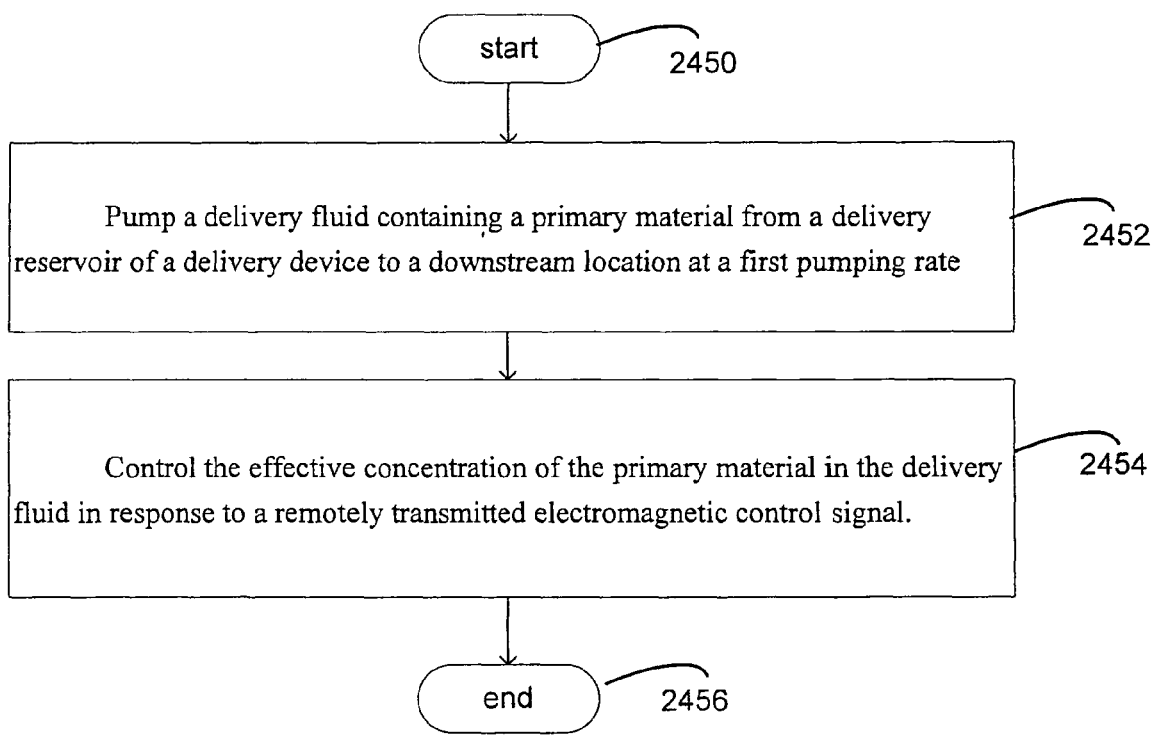
FIG. 53 is a flow diagram of a portion of a method of delivering a material.
Figure 55:
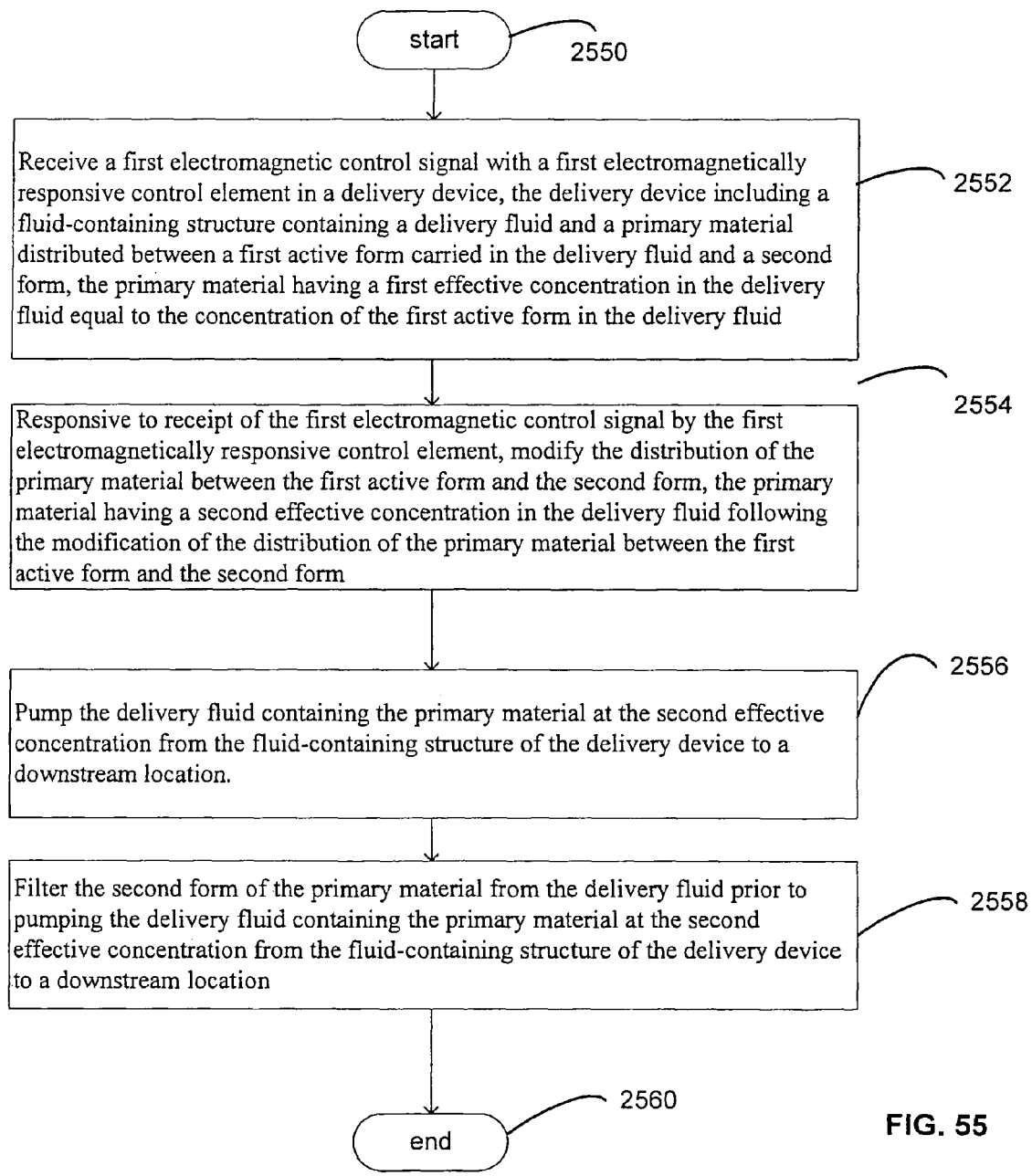
FIG. 55 is a flow diagram of an expansion of the method of FIG. 54.

FIG. 53 shows a method of delivering a material including pumping a delivery fluid containing a primary material from a delivery reservoir of a delivery device to a downstream location at a first pumping rate at step 2452; and controlling the effective concentration of the primary material in the delivery fluid in response to a remotely transmitted electromagnetic control signal at step 2454. In some embodiments, the first pumping rate may be a constant pumping rate. In some embodiment, the method may include varying the rate of delivery of the primary material to the downstream location by varying the effective concentration of the primary material in the delivery fluid in response to the remotely transmitted electromagnetic control signal. In other embodiments, the first pumping rate may be a time-varying pumping rate. In such embodiments, the method may include controlling the rate of delivery of the primary material to the downstream location by controlling both the effective concentration of the primary material in the delivery fluid and the pumping rate. The first pumping rate is modifiable in response to a remotely transmitted electromagnetic control signal, for example. The method may include controlling the effective concentration of the primary material in the delivery fluid through activation of an electromagnetically responsive control element in the delivery device by the remotely transmitted electromagnetic control signal, for example by heating of the electromagnetically responsive control element, cooling of the electromagnetically responsive control element. In some variants of the method, activation of the electromagnetically responsive control element may include a change in at least one dimension of the electromagnetically responsive control element, a change in orientation of the electromagnetically responsive control element, or a change in conformation of the electromagnetically responsive control element.

FIG. 54 shows a method of delivering a material, including receiving a first electromagnetic control signal with a first electromagnetically responsive control element in a delivery device, the delivery device including a fluid-containing structure containing a delivery fluid and a primary material distributed between a first active form carried in the delivery fluid and a second form, the primary material having a first effective concentration in the delivery fluid equal to the concentration of the first active form in the delivery fluid at step 2502; responsive to receipt of the first electromagnetic control signal by the first electromagnetically responsive control element, modifying the distribution of the primary material between the first active form and the second form, the primary material having a second effective concentration in the delivery fluid following the modification of the distribution of the primary material between the first active form and the second form at step 2504; and pumping the delivery fluid containing the primary material at the second effective concentration from the fluid-containing structure of the delivery device to a downstream location at step 2506. In the method of FIG. 54, the primary material has a different stability in the first active form than in the second form, a different immunogenicity in the first active form than in the second form, a different reactivity in the first active form than in the second form, or a different activity in the first active form than in the second form.

In a variant of the method of FIG. 54, shown in FIG. 55 (with steps 2552-2556 the same as steps 2502-2506), the method may include the additional step of filtering the second form of the primary material from the delivery fluid prior to pumping the delivery fluid containing the primary material at the second effective concentration from the fluid-containing structure of the delivery device to a downstream location 2558.

In the method of FIG. 54, in some embodiments the first effective concentration may be lower than the second effective concentration, and some embodiments first effective concentration may be higher than the second effective concentration. The method may include modifying the rate of pumping of the delivery fluid to the downstream location responsive to receipt of a second electromagnetic control signal by a second electromagnetically responsive control element. In some embodiments, the first electromagnetic control signal and the second electromagnetic control signal may be the same electromagnetic control signal. In other embodiments, the first electromagnetic control signal may be different than the second electromagnetic control signal. In some embodiments, the first electromagnetically responsive control element and the second electromagnetically responsive control element may be the same electromagnetically responsive control element, while in other embodiments, the first electromagnetically responsive control element may be a different control element than the second electromagnetically responsive control element. "Different" control elements may be control elements of different types, or distinct control elements that are of the same type.

FIG. 56 depicts further variants on the method of FIG. 54. Steps 2602 through 2606 are the same as steps 2502-2506 in FIG. 54. Steps 2608a-2608f alternative steps for modifying the distribution of primary material between the first active form and the second form. Step 2608a includes modifying the distribution of primary material in response to receipt of the first electromagnetic control signal by modifying a pressure within the fluid containing structure, step 2608b includes modifying the distribution of primary material in response to receipt of the first electromagnetic control signal by modifying a temperature within the fluid containing structure, step 2608c includes modifying the distribution of primary material in response to receipt of the first electromagnetic control signal by modifying a volume of the fluid containing structure, step 2608d includes modifying the distribution of primary material in response to receipt of the first electromagnetic control signal by producing vibration within the fluid containing structure, step 2608e includes modifying the distribution of primary material in response to receipt of the first electromagnetic control signal by producing fluid mixing within the fluid containing structure, and step 2608f includes modifying the distribution of primary material in response to receipt of the first electromagnetic control signal by modifying a number of available interaction sites within the fluid containing structure, the available interaction sites capable of interacting with the primary material to produce the second form of the primary material.

Figure 57:
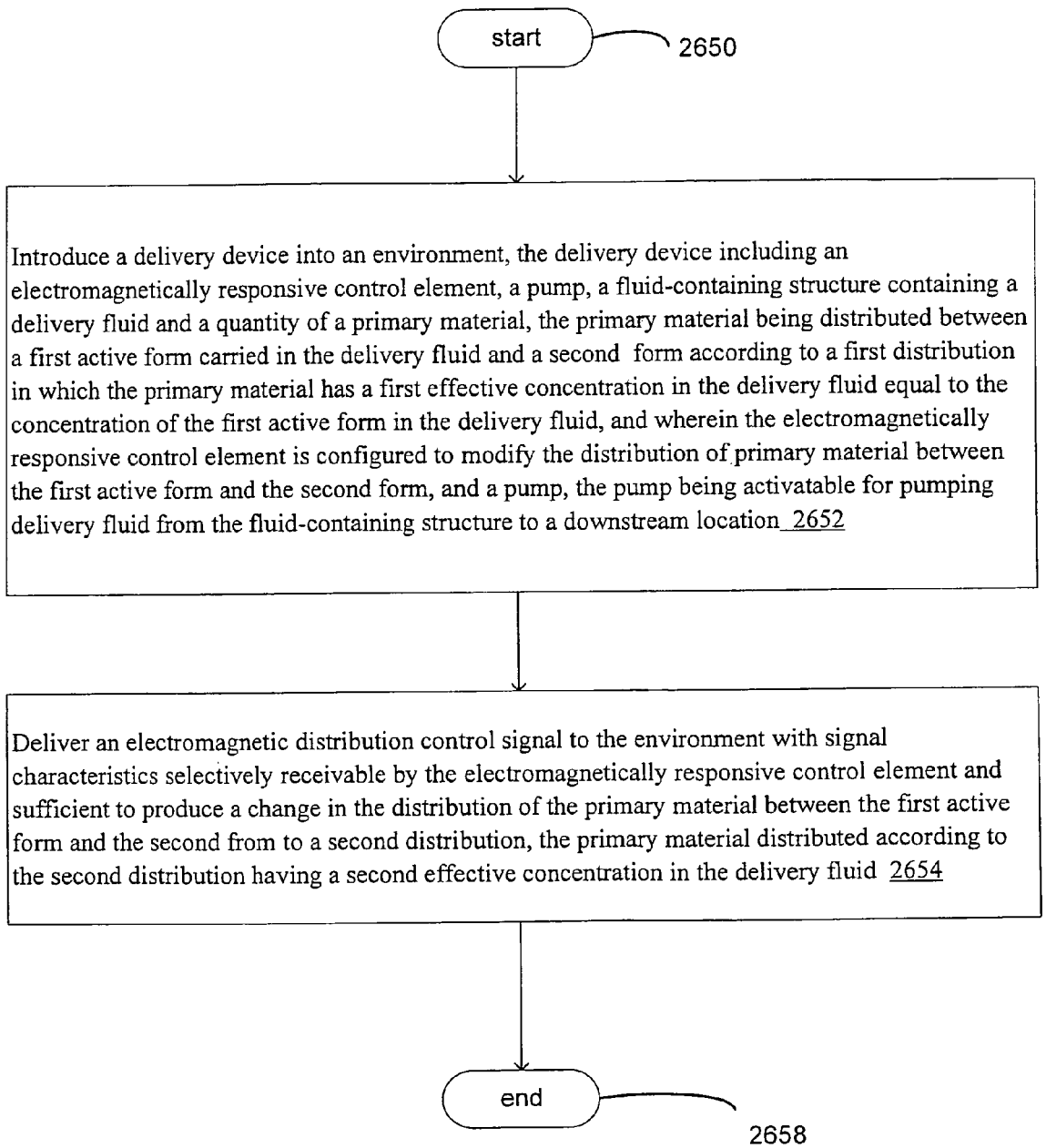
FIG. 57 is a flow diagram of a further method of delivering a material.

FIG. 57 illustrates a method of delivering a material, including, at step 2652, introducing a delivery device into an environment, the delivery device including an electromagnetically responsive control element, a pump, a fluid-containing structure containing a delivery fluid and a quantity of a primary material, the primary material being distributed between a first active form carried in the delivery fluid and a second form according to a first distribution in which the primary material has a first effective concentration in the delivery fluid equal to the concentration of the first active form in the delivery fluid, and wherein the electromagnetically responsive control element is configured to modify the distribution of primary material between the first active form and the second form, and a pump, the pump being activatable for pumping delivery fluid from the fluid-containing structure to a downstream location. At step 2654, the method includes a step of delivering an electromagnetic-distribution control signal to the environment with signal characteristics selectively receivable by the electromagnetically responsive control element and sufficient to produce a change in the distribution of the primary material between the first active form and the second from to a second distribution, the primary material distributed according to the second distribution having a second effective concentration in the delivery fluid. The pump may be activated to pump delivery fluid containing the primary material at the second effective concentration out of the fluid containing structure. In one variant, the pump may be activated prior to introducing the delivery device into the environment. In another variant, the pump may be activated upon introduction of the delivery device into the environment. In still another variant, the pump may be activated subsequent to introducing the delivery device into the environment. The method as depicted in FIG. 57 may also include delivering an electromagnetic delivery control signal having signal characteristics selectively receivable by a second electromagnetically responsive control element in the delivery device to produce the pumping of the delivery fluid containing the primary material at the second effective concentration out of the fluid-containing structure. The primary material may have a different immunogenicity, reactivity, or stability when it is in the first active form than when it is in the second form.

FIG. 58 illustrates a method of controlling a delivery device, which includes the steps of generating an electromagnetic control signal including frequency components absorbable by an electromagnetically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the electromagnetically responsive control element at 2702; and remotely transmitting the electromagnetic control signal to the delivery device with signal characteristics sufficient to activate the electromagnetically responsive control element in the delivery device to control the effective concentration of primary material in the delivery fluid in the delivery device at 2704.

FIG. 59 illustrates an expansion of the method shown in FIG. 58, with steps 2752 and 2754 being the same as steps 2702 and 2704, respectively, in FIG. 58, with a number of alternative steps relating to generation of the electromagnetic control signal. Step 2756a includes generating the electromagnetic control signal and transmitting the electromagnetic control signal to the delivery device with a remote controller. Step 2756b includes generating the electromagnetic control signal and transmitting the electromagnetic control signal to the delivery device with two or more remote controllers. Step 2756c includes generating the electromagnetic control signal from a model-based calculation. Step 2756d includes generating the electromagnetic control signal based on a stored pattern. As yet another alternative, step 2756e includes generating the electromagnetic control signal based upon a feedback control scheme. A feedback control scheme may be, for example, a variable feedback control scheme.

Figure 60:
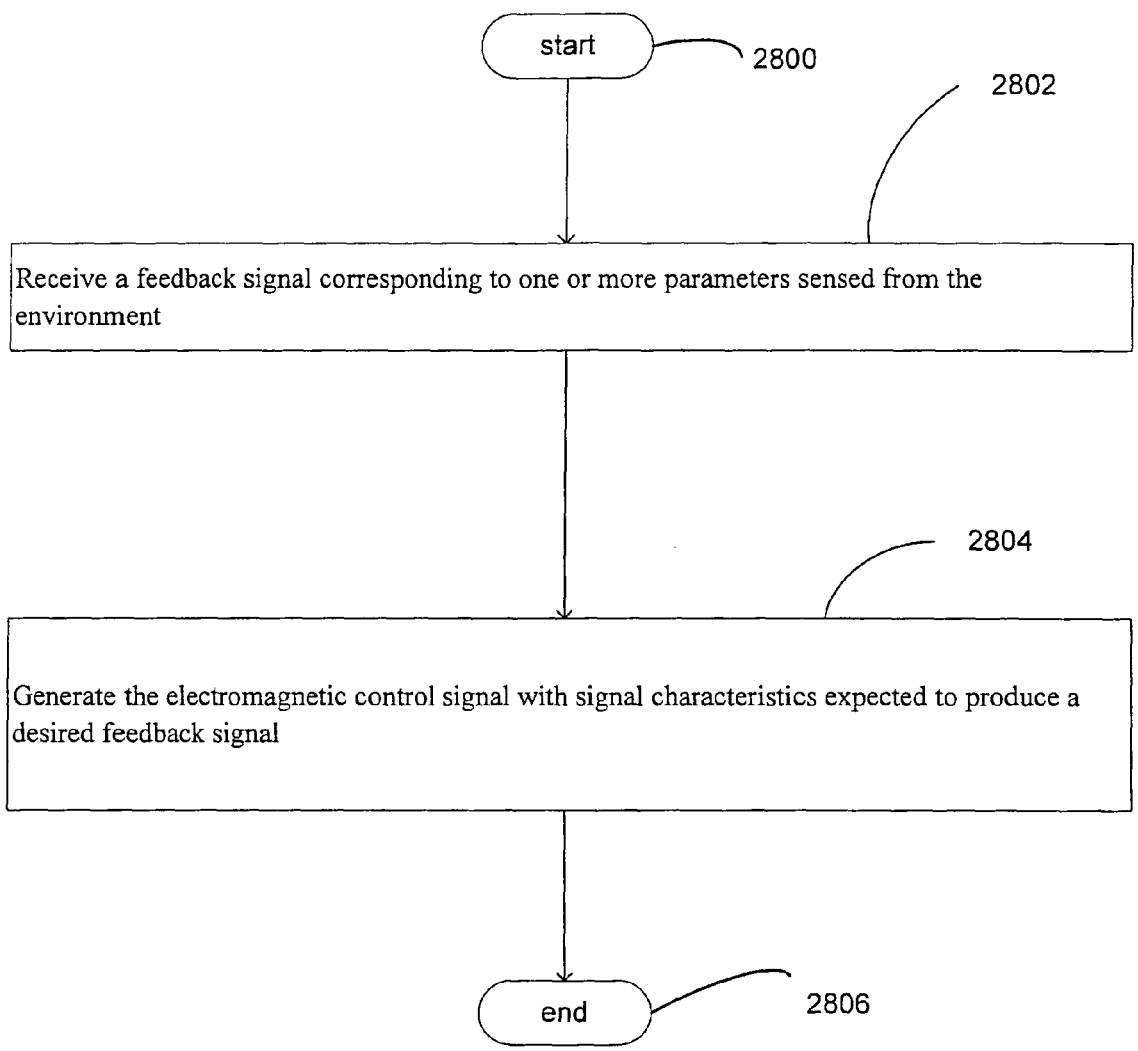
FIG. 60 is a flow diagram of additional steps for controlling a delivery device.

A further expansion the method shown in FIG. 58 may include the additional steps depicted in FIG. 60, namely receiving a feedback signal corresponding to one or more parameters sensed from the environment at 2802; and based upon the feedback signal, generating the electromagnetic control signal with signal characteristics expected to produce a desired feedback signal, at 2804. In some embodiments, receiving the feedback signal from the environment may include receiving signals from at least one sensor in the environment, while in other embodiments it may include receiving the feedback signal from the environment includes receiving signals from two or more sensors in the environment. Receiving the feedback signal from the environment may include receiving a measure of the concentration or chemical activity of a chemical within at least a portion of the environment.

Figure 61:
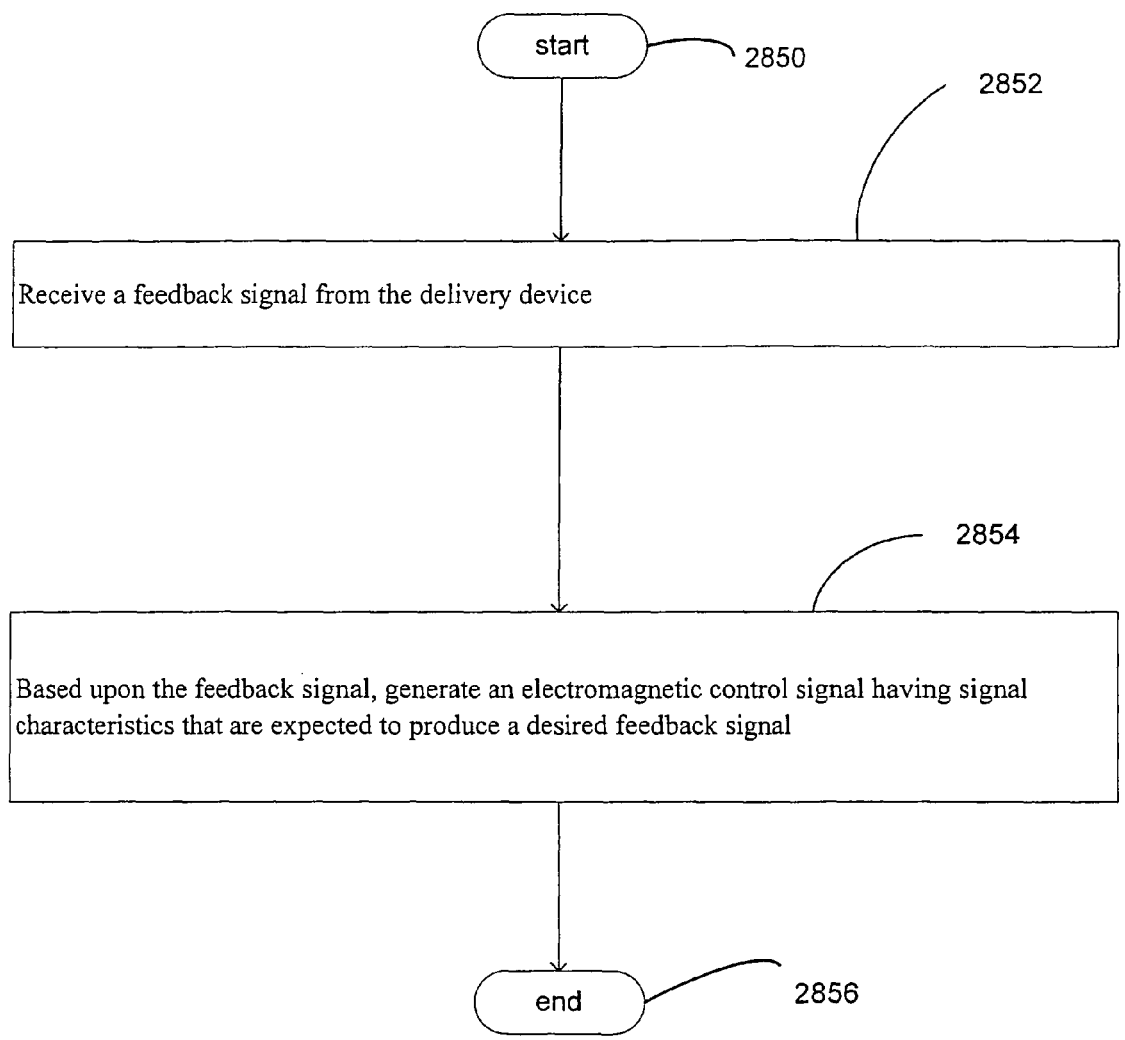
FIG. 61 is a flow diagram of alternative additional steps for controlling a delivery device.

In another variation of the method shown in FIG. 58, shown in FIG. 61, the method may include the additional steps of receiving a feedback signal from the delivery device at 2852; and based upon the feedback signal, generating an electromagnetic control signal having signal characteristics that are expected to produce a desired feedback signal at 2854. Receiving a feedback signal from the delivery device may include receiving signals from at least one sensor in the delivery device, or alternatively, receiving a feedback signal from the delivery device may include receiving signals from two or more sensors in the delivery device. For example, receiving the feedback signal from the delivery device may include receiving a signal representing a concentration or chemical activity of a chemical within or around the delivery device.

Another variation of the method depicted in FIG. 58, shown in FIG. 62, may include the additional steps of receiving user input of one or more control parameters at 2892; and based upon the one or more control parameters, generating an electromagnetic control signal having signal characteristics expected to produce a desired effective concentration of primary material in the delivery fluid, as 2894. The desired effective concentration of primary material in the delivery fluid may be an effective concentration sufficient to produce a desired rate of delivery of the first active form of the primary material to the environment by the delivery device.

Further additions to the method depicted in FIG. 58 include steps of activating the electromagnetically responsive control element to produce heating or cooling, or activating the electromagnetically responsive control element to produce a change in configuration of the electromagnetically responsive control element. Steps of generating an electromagnetic control signal and remotely transmitting the electromagnetic control signal to the delivery device, as shown in FIG. 58, may be performed according to instructions provided in the form of software, hardware or firmware. In some method embodiments, the steps of generating an electromagnetic control signal and remotely transmitting the electromagnetic control signal to the delivery device may be performed according to instructions distributed among a plurality of controllers or transmitters.

Generating the electromagnetic control signal includes generating a static or quasi-static magnetic field, static or quasi-static electrical field, radio-frequency electromagnetic signal, microwave electromagnetic signal, millimeter wave electromagnetic signal, optical electromagnetic signal, which may be an optical electromagnetic signal is an infrared electromagnetic signal, or generating an ultraviolet electromagnetic signal. Generating the electromagnetic control signal may be performed under software control.

FIG. 63 depicts a further variation of the method shown in FIG. 58, with steps 2902 and 2904 corresponding to steps 2702 and 2704, respectively. The method includes the additional step of modifying the concentration of the primary material within the delivery fluid in the fluid-containing structure of the delivery device by modifying the area of an interaction region within the fluid containing structure of the delivery device at 2906. Modifying the area of the interaction region includes increasing the area of the interaction region, as at 2906a, or alternatively, decreasing the area of the interaction region, as 2906b. In the case that the area is increased, and the interaction region includes interaction sites, and increasing the area of the interaction region may include increasing the distances between interaction sites in the interaction region, as at 2908a, or increasing the area of the interaction region includes increasing a number of interaction sites in the reaction area, as at 2908b. In the case that the area is decreased, as at 2906b, and the interaction region includes interaction sites, decreasing the area of the interaction region may include decreasing distances between one or more interaction sites in the interaction region, as at 2910a, or decreasing a number of interaction sites in the reaction area as at 2910b.

Figure 64:
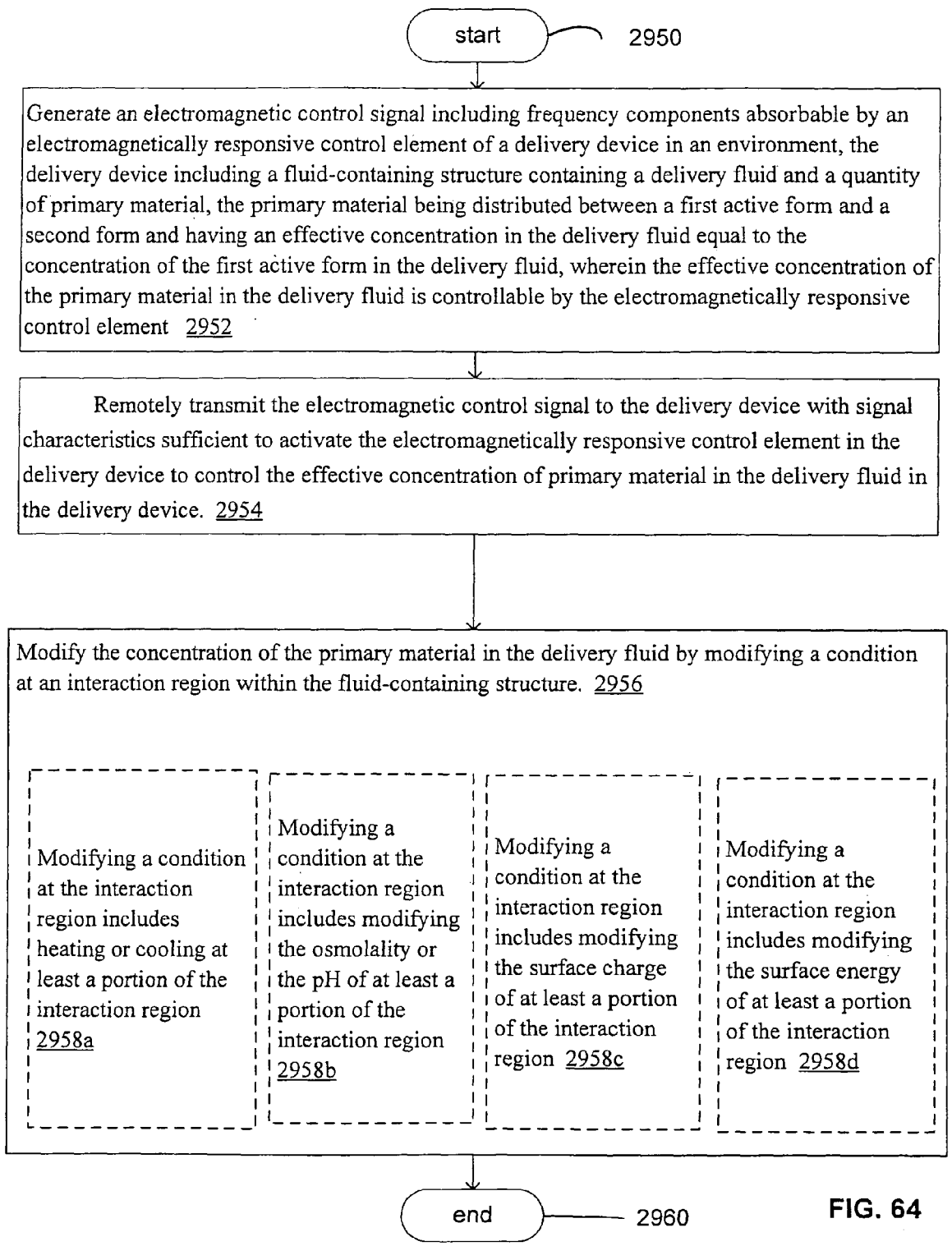
FIG. 64 is another expansion of the method of FIG. 58.

FIG. 64 depicts a further variation of the method shown in FIG. 58, with steps 2952 and 2954 corresponding to steps 2702 and 2704, respectively. The method further includes a further step of modifying the concentration of the primary material in the delivery fluid by modifying a condition at an interaction region within the fluid-containing structure, at 2956. Modifying a condition at the interaction region may include heating or cooling at least a portion of the interaction region, as shown at 2958a, modifying the osmolality or the pH of at least a portion of the interaction region, at 2958b, modifying the surface charge of at least a portion of the interaction region, at 2958c, or modifying the surface energy of at least a portion of the interaction region, as 1958d.

In another variation, shown in FIG. 65, the method includes a further step of modifying a condition at the interaction region by modifying a condition within the fluid-containing structure, as indicated at step 3006 (steps 3002 and 3004 correspond to steps 2702 and 2704 in FIG. 58). Modifying a condition within the fluid-containing structure may include modifying the volume of the fluid-containing structure, as shown at 3008a, heating or cooling at least a portion of the fluid-containing structure, as shown at 3008b, or modifying the osmolality or the pH within at least a portion of the fluid-containing structure, as shown at 3008c.

FIG. 67 is a flow diagram of a method of controlling a delivery device. At step 3102, the method includes generating an acoustic control signal including frequency components absorbable by an acoustically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the acoustically responsive control element. At step 3104, the method include remotely transmitting the acoustic control signal to the delivery device with signal characteristics sufficient to activate the acoustically responsive control element in the delivery device to control the effective concentration of primary material in the delivery fluid in the delivery device.

FIG. 68 provides further detail on the method steps depicted in FIG. 67. As before, the method includes generating an acoustic control signal including frequency components absorbable by an acoustically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the acoustically responsive control element, at step 3152, and remotely transmitting the acoustic control signal to the delivery device with signal characteristics sufficient to activate the acoustically responsive control element in the delivery device to control the effective concentration of primary material in the delivery fluid in the delivery device, at step 3154. Step 3152 can be carried out in a number of different ways (with different options indicated in dashed boxes), including generating the acoustic control signal from a model-based calculation, as indicated at 3158, generating the acoustic control signal based on a stored pattern, as indicated at 3160, or generating the acoustic control signal based upon a feedback control scheme, as indicated at 3162.

FIG. 69 details further alternative embodiments of the method of controlling a delivery device shown in FIG. 67. As before, the method includes generating an acoustic control signal including frequency components absorbable by an acoustically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the acoustically responsive control element, at step 3202, and remotely transmitting the acoustic control signal to the delivery device with signal characteristics sufficient to activate the acoustically responsive control element in the delivery device to control the effective concentration of primary material in the delivery fluid in the delivery device, at step 3204. As indicated in the dashed boxes, the method may also include additional steps such as receiving a feedback signal corresponding to one or more parameters sensed from the environment, and, based upon the feedback signal, generating the acoustic control signal with signal characteristics expected to produce a desired feedback signal, as shown at 3208. Alternatively, the method may include receiving a feedback signal from the delivery device and, based upon the feedback signal, generating the acoustic control signal with signal characteristics expected to produce a desired feedback signal, as shown at 3210. In still other embodiments, the method may include receiving user input of one or more control parameters, and based upon the one or more control parameters, generating the acoustic control signal with signal characteristics expected to produce a desired effective concentration of primary material in the delivery fluid.

In methods as illustrated in FIGS. 67-69, some or all of the steps of generating an acoustic control signal and remotely transmitting the acoustic control signal to the delivery device may be performed according to instructions provided in the form of software, hardware or firmware. Some or all of the steps of generating an acoustic control signal and remotely transmitting the acoustic control signal to the delivery device may be performed according to instructions distributed among a plurality of controllers or transmitters. The acoustic control signal may be generated under software control in some embodiments.

Software may be used in performing various of the methods as described herein. Such software includes software for controlling delivery of a material from a delivery device, including instructions for generating an electromagnetic control signal including frequency components absorbable by an electromagnetically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the electromagnetically responsive control element; and instructions for controlling the transmission of the electromagnetic control signal to the delivery device with signal characteristics sufficient to activate the electromagnetically responsive control element in the delivery device to control the effective concentration of primary material in the delivery fluid in the delivery device.

The software may include instructions for generating the electromagnetic control signal include instructions for calculating the electromagnetic control signal based on a model. The instructions for generating the electromagnetic control signal may include instructions for generating the electromagnetic control signal based on a pattern stored in a data storage location, or instructions for generating the electromagnetic control signal based upon a feedback control algorithm. For example, the instructions for generating the electromagnetic control signal may include instructions for generating the electromagnetic control signal based upon a variable feedback control algorithm. The software may include instructions for receiving a feedback signal corresponding to one or more parameters sensed from the environment; and instructions for generating the electromagnetic control signal based at least in part upon the received feedback signal, the electromagnetic control signal having signal characteristics expected to produce a desired feedback signal. Some embodiments of the software may include instructions for receiving a feedback signal from the delivery device; and instructions for generating the electromagnetic control signal based at least in part on the received feedback signal, the electromagnetic control signal having frequency composition and amplitude expected to produce a desired feedback signal. In some embodiments, the software may include instructions for receiving user input of one or more control parameters; and instructions for generating the electromagnetic control signal based at least in part upon the one or more control parameters. In some embodiments, the software may include instructions for performing encryption of the electromagnetic control signal. Instruction may be included for performing an authentication procedure between a remote controller transmitting the electromagnetic control signal and a delivery device including the electromagnetically responsive control element intended to be activated by the electromagnetic control signal. At least a portion of the instructions generating the electromagnetic control signal and the instruction for controlling the transmission of the electromagnetic control signal are executable in distributed fashion on a plurality of microprocessors. Some embodiments of the software may include channel allocation instructions configured to control the allocation of control signal transmission channels for transmission of a plurality of control signals to a corresponding plurality of delivery devices.

With regard to the hardware and/or software used in the control of devices and systems according to the present embodiments, and particularly to the sensing, analysis, and control aspects of such systems, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and related processes or methods via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that certain mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for detection or sensing, signal processing, and device control in the fashion set forth herein, and thereafter use standard engineering practices to integrate such described devices and/or processes into fluid handling and/or delivery systems as exemplified herein. That is, at least a portion of the devices and/or processes described herein can be integrated into a fluid handling and/or delivery system via a reasonable amount of experimentation.

Those having skill in the art will recognize that systems as described herein may include one or more of a memory such as volatile and non-volatile memory, processors such as microprocessors and digital signal processors, computational-supporting or—associated entities such as operating systems, user interfaces, drivers, sensors, actuators, applications programs, one or more interaction devices, such as data ports, control systems including feedback loops and control implementing actuators (e.g., devices for sensing osmolality, pH, pressure, temperature, or chemical concentration, signal generators for generating electromagnetic control signals). A system may be implemented utilizing any suitable available components, combined with standard engineering practices.

The foregoing-described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. In particular, while selected examples of systems, devices, components and methods employing acoustic signal generation, transmission, and reception are specifically described, it will be appreciated that various other systems, devices, components and methods described herein in connection with the use of electromagnetic, electrical, or magnetic control signals may be modified to instead employ acoustic control signals, and that such modification will be apparent to those of skill in the art, and such modifications are considered to fall within the scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of remote controller, system configuration and fluid handling/delivery device may be within the scope of the invention. As has been discussed, the choice of system configuration may depend on the intended application of the system, the environment in which the system is used, cost, personal preference or other factors. System design, manufacture, and control processes may be modified to take into account choices of use environment and intended application, and such modifications, as known to those of skill in the arts of device design and construction, may fall within the scope of the invention. Therefore, the full spirit or scope of the invention is defined by the appended claims and is not to be limited to the specific embodiments described herein.

While various aspects and embodiments have been disclosed herein, other aspects and embodiments will be apparent to those skilled in the art. It is intended that the various aspects and embodiments disclosed herein are for purposes of illustration and are not intended to be limiting, with the true scope and spirit being indicated by the following claims.

What is claimed is:

1. A method of controlling a delivery device, comprising:
generating an acoustic control signal including frequency components absorbable by an acoustically responsive control element of a delivery device in an environment, the delivery device including a fluid-containing structure containing a delivery fluid and a quantity of primary material, the primary material being distributed between a first active form and a second form and having an effective concentration in the delivery fluid equal to the concentration of the first active form in the delivery fluid, wherein the effective concentration of the primary material in the delivery fluid is controllable by the acoustically responsive control element by modifying a condition at an interaction region within the fluid-containing structure upon activation of the acoustically responsive control element by the acoustic control signal, wherein modifying the condition at the interaction region modifies interaction between an interaction site of the interaction region and the primary material, and wherein modifying the condition at the interaction region includes heating or cooling at least a portion of the interaction region; and remotely transmitting the acoustic control signal to the delivery device with signal characteristics sufficient to activate the acoustically responsive control element in the delivery device to control the effective concentration of primary material in the delivery fluid in the delivery device.

2. The method of claim 1, including generating the acoustic control signal and transmitting the acoustic control signal to the delivery device with a remote controller.

3. The method of claim 1, including generating the acoustic control signal and transmitting the acoustic control signal to the delivery device with two or more remote controllers.

4. The method of claim 1, including generating the acoustic control signal from a model-based calculation.

5. The method of claim 1, including generating the acoustic control signal based on a stored pattern.

6. The method of claim 1, including generating the acoustic control signal based upon a feedback control scheme.

7. The method of claim 6, including generating the acoustic control signal based upon a variable feedback control scheme.

8. The method of claim 1, including:

receiving a feedback signal corresponding to one or more parameters sensed from the environment; and based upon the feedback signal, generating the acoustic control signal with signal characteristics expected to produce a desired feedback signal.

9. The method of claim 8, wherein receiving the feedback signal from the environment includes receiving signals from at least one sensor in the environment.

10. The method of claim 8, wherein receiving the feedback signal from the environment includes receiving signals from two or more sensors in the environment.

11. The method of claim 8, wherein receiving the feedback signal from the environment includes receiving a measure of the concentration or chemical activity of a chemical within at least a portion of the environment.

12. The method of claim 1, including:
receiving a feedback signal from the delivery device; and
based upon the feedback signal, generating the acoustic control signal with signal characteristics expected to produce a desired feedback signal.

13. The method of claim 12, wherein receiving a feedback signal from the delivery device includes receiving signals from at least one sensor in the delivery device.

14. The method of claim 12, wherein receiving a feedback signal from the delivery device includes receiving signals from two or more sensors in the delivery device.

15. The method of claim 12, wherein receiving the feedback signal from the delivery device includes receiving a signal representing a concentration or chemical activity of a chemical within or around the delivery device.

16. The method of claim 1, including:
receiving user input of one or more control parameters; and
based upon the one or more control parameters, generating the acoustic control signal with signal characteristics expected to produce a desired effective concentration of primary material in the delivery fluid.

17. The method of claim 16, wherein the desired effective concentration of primary material in the delivery fluid is an